(12) United States Patent
Bernate et al.

(10) Patent No.: US 12,427,518 B2
(45) Date of Patent: Sep. 30, 2025

(54) MICROFLUIDIC ON-CHIP FILTERS

(71) Applicant: 10X GENOMICS, INC., Pleasanton, CA (US)

(72) Inventors: Jorge Bernate, Pleasanton, CA (US); Rajiv Bharadwaj, Pleansanton, CA (US); Donald A. Masquelier, Pleasanton, CA (US); Tobias Daniel Wheeler, Alameda, CA (US)

(73) Assignee: 10x Genomics, Inc., Pleasanton, CA (US)

( * ) Notice: Subject to any disclaimer, the term of this patent is extended or adjusted under 35 U.S.C. 154(b) by 78 days.

(21) Appl. No.: 16/180,378

(22) Filed: Nov. 5, 2018

(65) Prior Publication Data

US 2019/0134629 A1 May 9, 2019

Related U.S. Application Data

(63) Continuation of application No. PCT/US2017/032525, filed on May 12, 2017.

(Continued)

(51) Int. Cl.
*B01L 3/00* (2006.01)
*C12M 1/12* (2006.01)
(Continued)

(52) U.S. Cl.
CPC ... *B01L 3/502753* (2013.01); *B01L 3/502761* (2013.01); *C12M 23/16* (2013.01);
(Continued)

(58) Field of Classification Search
CPC ......... B01L 3/502753; B01L 3/502761; B01L 2200/0631; B01L 2200/0647;
(Continued)

(56) References Cited

U.S. PATENT DOCUMENTS 2,797,149 A 6/1957 Skeggs
3,047,367 A 7/1962 Kessler
(Continued)

FOREIGN PATENT DOCUMENTS

CN 102292455 A 12/2011
CN 103202812 A 7/2013
(Continued)

OTHER PUBLICATIONS

Groisman et al (A Microfluidic Rectifier: Anisotropic Flow Resistance at Low Reynolds Numbers, Physical Review Letters, 2004, vol. 92, No. 9, pp. 094501-1 to 094501-4, see attached document) (Year: 2004).*

(Continued)

*Primary Examiner* — Dennis White
(74) *Attorney, Agent, or Firm* — Clark & Elbing LLP

(57) ABSTRACT

A microfluidic system for manipulating particles in a fluid is provided. The system includes a microfluidic chip having at least one channel and at least one filter feature, wherein the filter feature includes a field of physical obstacles configured and arranged to remove physical contaminants associated with the particles. The filter features are particularly suited to remove contaminants associated with gel beads manipulated by microfluidic handling.

22 Claims, 15 Drawing Sheets

Related U.S. Application Data

(60) Provisional application No. 62/335,216, filed on May 12, 2016.

(51) Int. Cl.
  *C12M 3/06* (2006.01)
  *C12N 1/02* (2006.01)
  *C12N 11/04* (2006.01)

(52) U.S. Cl.
  CPC .............. *C12M 25/04* (2013.01); *C12N 1/02* (2013.01); *C12N 11/04* (2013.01); *B01L 2200/0631* (2013.01); *B01L 2200/0647* (2013.01); *B01L 2300/021* (2013.01); *B01L 2300/0681* (2013.01); *B01L 2300/0816* (2013.01)

(58) Field of Classification Search
  CPC ....... B01L 2300/021; B01L 2300/0681; B01L 2300/0816; C12M 23/16; C12M 25/04; C12N 11/04; C12N 1/02
  See application file for complete search history.

(56) References Cited

U.S. PATENT DOCUMENTS

| | | |
|---|---|---|
| 3,479,141 A | 11/1969 | William et al. |
| 4,124,638 A | 11/1978 | Hansen |
| 4,253,846 A | 3/1981 | Smythe et al. |
| 4,582,802 A | 4/1986 | Zimmerman et al. |
| 5,137,829 A | 8/1992 | Nag et al. |
| 5,149,625 A | 9/1992 | Church et al. |
| 5,185,099 A | 2/1993 | Delpuech et al. |
| 5,202,231 A | 4/1993 | Drmanac et al. |
| 5,270,183 A | 12/1993 | Corbett et al. |
| 5,413,924 A | 5/1995 | Kosak et al. |
| 5,418,149 A | 5/1995 | Gelfand et al. |
| 5,436,130 A | 7/1995 | Mathies et al. |
| 5,478,893 A | 12/1995 | Ghosh et al. |
| 5,489,523 A | 2/1996 | Mathur |
| 5,512,131 A | 4/1996 | Kumar et al. |
| 5,558,071 A | 9/1996 | Ward et al. |
| 5,585,069 A | 12/1996 | Zanzucchi et al. |
| 5,587,128 A | 12/1996 | Wilding et al. |
| 5,605,793 A | 2/1997 | Stemmer et al. |
| 5,618,711 A | 4/1997 | Gelfand et al. |
| 5,658,548 A | 8/1997 | Padhye et al. |
| 5,695,940 A | 12/1997 | Drmanac et al. |
| 5,700,642 A | 12/1997 | Monforte et al. |
| 5,705,628 A | 1/1998 | Hawkins et al. |
| 5,708,153 A | 1/1998 | Dower et al. |
| 5,736,330 A | 4/1998 | Fulton |
| 5,739,036 A | 4/1998 | Parris |
| 5,744,311 A | 4/1998 | Fraiser et al. |
| 5,756,334 A | 5/1998 | Perler et al. |
| 5,834,197 A | 11/1998 | Parton |
| 5,842,787 A | 12/1998 | Kopf-Sill et al. |
| 5,846,719 A | 12/1998 | Brenner et al. |
| 5,846,727 A | 12/1998 | Soper et al. |
| 5,851,769 A | 12/1998 | Gray et al. |
| 5,856,174 A | 1/1999 | Lipshutz et al. |
| 5,872,010 A | 2/1999 | Karger et al. |
| 5,897,783 A | 4/1999 | Howe et al. |
| 5,900,481 A | 5/1999 | Lough et al. |
| 5,942,609 A | 8/1999 | Hunkapiller et al. |
| 5,958,703 A | 9/1999 | Dower et al. |
| 5,965,443 A | 10/1999 | Reznikoff et al. |
| 5,989,402 A | 11/1999 | Chow et al. |
| 5,994,056 A | 11/1999 | Higuchi |
| 5,997,636 A | 12/1999 | Gamarnik et al. |
| 6,033,880 A | 3/2000 | Haff et al. |
| 6,046,003 A | 4/2000 | Mandecki |
| 6,051,377 A | 4/2000 | Mandecki |
| 6,057,107 A | 5/2000 | Fulton |
| 6,057,149 A | 5/2000 | Burns et al. |
| 6,103,537 A | 8/2000 | Ullman et al. |
| 6,133,436 A | 10/2000 | Koester et al. |
| 6,143,496 A | 11/2000 | Brown et al. |
| 6,159,717 A | 12/2000 | Savakis et al. |
| 6,171,850 B1 | 1/2001 | Nagle et al. |
| 6,172,218 B1 | 1/2001 | Brenner |
| 6,207,384 B1 | 3/2001 | Mekalanos et al. |
| 6,258,571 B1 | 7/2001 | Chumakov et al. |
| 6,265,552 B1 | 7/2001 | Schatz |
| 6,281,254 B1 | 8/2001 | Nakajima et al. |
| 6,291,243 B1 | 9/2001 | Fogarty et al. |
| 6,294,385 B1 | 9/2001 | Goryshin et al. |
| 6,296,020 B1 | 10/2001 | McNeely et al. |
| 6,297,006 B1 | 10/2001 | Drmanac et al. |
| 6,297,017 B1 | 10/2001 | Schmidt et al. |
| 6,303,343 B1 | 10/2001 | Kopf-Sill |
| 6,306,590 B1 | 10/2001 | Mehta et al. |
| 6,327,410 B1 | 12/2001 | Walt et al. |
| 6,355,198 B1 | 3/2002 | Kim et al. |
| 6,361,950 B1 | 3/2002 | Mandecki |
| 6,372,813 B1 | 4/2002 | Johnson et al. |
| 6,379,929 B1 | 4/2002 | Burns et al. |
| 6,406,848 B1 | 6/2002 | Bridgham et al. |
| 6,409,832 B2 | 6/2002 | Weigl et al. |
| 6,432,290 B1 | 8/2002 | Harrison et al. |
| 6,432,360 B1 | 8/2002 | Church |
| 6,481,453 B1 | 11/2002 | O'Connor et al. |
| 6,485,944 B1 | 11/2002 | Church et al. |
| 6,492,118 B1 | 12/2002 | Abrams et al. |
| 6,503,757 B1 | 1/2003 | Chow et al. |
| 6,511,803 B1 | 1/2003 | Church et al. |
| 6,524,456 B1 | 2/2003 | Ramsey et al. |
| 6,569,631 B1 | 5/2003 | Pantoliano et al. |
| 6,579,851 B2 | 6/2003 | Goeke et al. |
| 6,586,176 B1 | 7/2003 | Trnovsky et al. |
| 6,593,113 B1 | 7/2003 | Tenkanen et al. |
| 6,613,752 B2 | 9/2003 | Kay et al. |
| 6,632,606 B1 | 10/2003 | Ullman et al. |
| 6,632,655 B1 | 10/2003 | Mehta et al. |
| 6,670,133 B2 | 12/2003 | Knapp et al. |
| 6,723,513 B2 | 4/2004 | Lexow |
| 6,767,731 B2 | 7/2004 | Hannah |
| 6,800,298 B1 | 10/2004 | Burdick et al. |
| 6,806,052 B2 | 10/2004 | Bridgham et al. |
| 6,806,058 B2 | 10/2004 | Jesperson et al. |
| 6,859,570 B2 | 2/2005 | Walt et al. |
| 6,880,576 B2 | 4/2005 | Karp et al. |
| 6,884,788 B2 | 4/2005 | Bulpitt et al. |
| 6,913,935 B1 | 7/2005 | Thomas |
| 6,929,859 B2 | 8/2005 | Chandler et al. |
| 6,969,488 B2 | 11/2005 | Bridgham et al. |
| 6,974,669 B2 | 12/2005 | Mirkin et al. |
| 7,041,481 B2 | 5/2006 | Anderson et al. |
| 7,115,400 B1 | 10/2006 | Adessi et al. |
| 7,129,091 B2 | 10/2006 | Ismagilov et al. |
| 7,138,267 B1 | 11/2006 | Jendrisak et al. |
| 7,211,654 B2 | 5/2007 | Gao et al. |
| 7,268,167 B2 | 9/2007 | Higuchi et al. |
| 7,282,370 B2 | 10/2007 | Bridgham et al. |
| 7,294,503 B2 | 11/2007 | Quake et al. |
| 7,297,485 B2 | 11/2007 | Bornarth et al. |
| 7,316,903 B2 | 1/2008 | Yanagihara et al. |
| 7,323,305 B2 | 1/2008 | Leamon et al. |
| 7,329,493 B2 | 2/2008 | Chou et al. |
| 7,425,431 B2 | 9/2008 | Church et al. |
| 7,536,928 B2 | 5/2009 | Kazuno |
| 7,544,473 B2 | 6/2009 | Brenner |
| 7,604,938 B2 | 10/2009 | Takahashi et al. |
| 7,608,434 B2 | 10/2009 | Reznikoff et al. |
| 7,608,451 B2 | 10/2009 | Cooper et al. |
| 7,622,280 B2 | 11/2009 | Holliger et al. |
| 7,638,276 B2 | 12/2009 | Griffiths et al. |
| 7,645,596 B2 | 1/2010 | Williams et al. |
| 7,666,664 B2 | 2/2010 | Sarofim et al. |
| 7,700,325 B2 | 4/2010 | Cantor et al. |
| 7,708,949 B2 | 5/2010 | Stone et al. |
| 7,709,197 B2 | 5/2010 | Drmanac |
| 7,745,178 B2 | 6/2010 | Dong |
| 7,745,218 B2 | 6/2010 | Kim et al. |

(56) References Cited

U.S. PATENT DOCUMENTS

| | | |
|---|---|---|
| 7,776,927 B2 | 8/2010 | Chu et al. |
| RE41,780 E | 9/2010 | Anderson et al. |
| 7,799,553 B2 | 9/2010 | Mathies et al. |
| 7,842,457 B2 | 11/2010 | Berka et al. |
| 7,901,891 B2 | 3/2011 | Drmanac |
| 7,910,354 B2 | 3/2011 | Drmanac et al. |
| 7,943,671 B2 | 5/2011 | Herminghaus et al. |
| 7,947,477 B2 | 5/2011 | Schroeder et al. |
| 7,960,104 B2 | 6/2011 | Drmanac et al. |
| 7,968,287 B2 | 6/2011 | Griffiths et al. |
| 7,972,778 B2 | 7/2011 | Brown et al. |
| 8,003,312 B2 | 8/2011 | Krutzik et al. |
| 8,008,018 B2 | 8/2011 | Quake et al. |
| 8,053,192 B2 | 11/2011 | Bignell et al. |
| 8,067,159 B2 | 11/2011 | Brown et al. |
| 8,101,346 B2 | 1/2012 | Takahama |
| 8,124,404 B2 | 2/2012 | Alphey et al. |
| 8,133,719 B2 | 3/2012 | Drmanac et al. |
| 8,137,563 B2 | 3/2012 | Ma et al. |
| 8,168,385 B2 | 5/2012 | Brenner et al. |
| 8,252,539 B2 | 8/2012 | Quake et al. |
| 8,268,564 B2 | 9/2012 | Roth et al. |
| 8,273,573 B2 | 9/2012 | Ismagilov et al. |
| 8,278,071 B2 | 10/2012 | Brown et al. |
| 8,298,767 B2 | 10/2012 | Brenner et al. |
| 8,304,193 B2 | 11/2012 | Ismagilov et al. |
| 8,318,433 B2 | 11/2012 | Brenner |
| 8,318,460 B2 | 11/2012 | Cantor et al. |
| 8,329,407 B2 | 12/2012 | Ismagilov et al. |
| 8,337,778 B2 | 12/2012 | Stone et al. |
| 8,361,299 B2 | 1/2013 | Sabin et al. |
| 8,420,386 B2 | 4/2013 | Ivics et al. |
| 8,461,129 B2 | 6/2013 | Bolduc et al. |
| 8,518,705 B2 * | 8/2013 | Chan ................ B01F 33/30 422/503 |
| 8,563,274 B2 | 10/2013 | Brenner et al. |
| 8,592,150 B2 | 11/2013 | Drmanac et al. |
| 8,598,328 B2 | 12/2013 | Koga et al. |
| 8,603,749 B2 | 12/2013 | Gillevet et al. |
| 8,679,756 B1 | 3/2014 | Brenner et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,822,148 B2 | 9/2014 | Ismagliov et al. |
| 8,829,171 B2 | 9/2014 | Steemers et al. |
| 8,835,358 B2 | 9/2014 | Fodor et al. |
| 8,871,444 B2 | 10/2014 | Griffiths et al. |
| 8,889,083 B2 | 11/2014 | Ismagilov et al. |
| 8,927,218 B2 | 1/2015 | Forsyth |
| 8,975,302 B2 | 3/2015 | Light et al. |
| 8,986,286 B2 | 3/2015 | Tanghoj et al. |
| 9,005,935 B2 | 4/2015 | Belyaev |
| 9,012,390 B2 | 4/2015 | Holtze et al. |
| 9,017,948 B2 | 4/2015 | Agresti et al. |
| 9,029,083 B2 | 5/2015 | Griffiths et al. |
| 9,029,085 B2 | 5/2015 | Agresti et al. |
| 9,068,210 B2 | 6/2015 | Agresti et al. |
| 9,074,251 B2 | 7/2015 | Steemers et al. |
| 9,080,211 B2 | 7/2015 | Grunenwald et al. |
| 9,089,844 B2 | 7/2015 | Hiddessen et al. |
| 9,102,980 B2 | 8/2015 | Brenner et al. |
| 9,126,160 B2 | 9/2015 | Colston, Jr. et al. |
| 9,133,009 B2 | 9/2015 | Baroud et al. |
| 9,150,916 B2 | 10/2015 | Christen et al. |
| 9,175,295 B2 | 11/2015 | Kaminaka et al. |
| 9,238,671 B2 | 1/2016 | Goryshin et al. |
| 9,249,460 B2 | 2/2016 | Pushkarev et al. |
| 9,273,349 B2 | 3/2016 | Nguyen et al. |
| 9,290,808 B2 | 3/2016 | Fodor et al. |
| 9,328,382 B2 | 5/2016 | Drmanac et al. |
| 9,347,059 B2 | 5/2016 | Saxonov |
| 9,388,465 B2 | 7/2016 | Hindson et al. |
| 9,410,201 B2 | 8/2016 | Hindson et al. |
| 9,500,664 B2 | 11/2016 | Ness et al. |
| 9,567,631 B2 | 2/2017 | Hindson et al. |
| 9,574,226 B2 | 2/2017 | Gormley et al. |
| 9,636,682 B2 | 5/2017 | Hiddessen et al. |
| 9,637,799 B2 | 5/2017 | Fan et al. |
| 9,644,204 B2 | 5/2017 | Hindson et al. |
| 9,649,635 B2 | 5/2017 | Hiddessen et al. |
| 9,689,024 B2 | 6/2017 | Hindson et al. |
| 9,694,361 B2 | 7/2017 | Bharadwaj et al. |
| 9,695,468 B2 | 7/2017 | Hindson et al. |
| 9,701,998 B2 | 7/2017 | Hindson et al. |
| 9,856,530 B2 | 1/2018 | Hindson et al. |
| 9,951,386 B2 | 4/2018 | Hindson et al. |
| 9,957,558 B2 | 5/2018 | Leamon et al. |
| 9,975,122 B2 | 5/2018 | Masquelier et al. |
| 10,011,872 B1 | 7/2018 | Belgrader et al. |
| 10,030,267 B2 | 7/2018 | Hindson et al. |
| 10,041,116 B2 | 8/2018 | Hindson et al. |
| 10,053,723 B2 | 8/2018 | Hindson et al. |
| 10,059,989 B2 | 8/2018 | Giresi et al. |
| 10,071,377 B2 | 9/2018 | Bharadwaj et al. |
| 10,137,449 B2 | 11/2018 | Bharadwaj et al. |
| 10,150,117 B2 | 12/2018 | Bharadwaj et al. |
| 10,221,442 B2 | 3/2019 | Hindson et al. |
| 10,245,587 B2 | 4/2019 | Masquelier et al. |
| 2001/0020588 A1 | 9/2001 | Adourian et al. |
| 2001/0036669 A1 | 11/2001 | Jedrzejewski et al. |
| 2001/0041357 A1 | 11/2001 | Fouillet et al. |
| 2001/0044109 A1 | 11/2001 | Mandecki |
| 2001/0048900 A1 | 12/2001 | Bardell et al. |
| 2001/0052460 A1 | 12/2001 | Chien et al. |
| 2001/0053519 A1 | 12/2001 | Fodor et al. |
| 2002/0001856 A1 | 1/2002 | Chow et al. |
| 2002/0003001 A1 | 1/2002 | Weigl et al. |
| 2002/0005354 A1 | 1/2002 | Spence et al. |
| 2002/0034737 A1 | 3/2002 | Drmanac |
| 2002/0043463 A1 | 4/2002 | Shenderov |
| 2002/0051971 A1 | 5/2002 | Stuelpnagel et al. |
| 2002/0051992 A1 | 5/2002 | Bridgham et al. |
| 2002/0058332 A1 | 5/2002 | Quake et al. |
| 2002/0065609 A1 | 5/2002 | Ashby et al. |
| 2002/0068278 A1 | 6/2002 | Giese et al. |
| 2002/0081744 A1 * | 6/2002 | Chan ................ B01L 3/502761 436/164 |
| 2002/0089100 A1 | 7/2002 | Kawasaki |
| 2002/0092767 A1 | 7/2002 | Bjornson et al. |
| 2002/0113009 A1 | 8/2002 | O'Connor et al. |
| 2002/0119455 A1 | 8/2002 | Chan et al. |
| 2002/0119536 A1 | 8/2002 | Stern |
| 2002/0131147 A1 | 9/2002 | Paolini et al. |
| 2002/0160518 A1 | 10/2002 | Hayenga et al. |
| 2002/0164820 A1 | 11/2002 | Brown |
| 2002/0166582 A1 | 11/2002 | O'Connor et al. |
| 2002/0172965 A1 | 11/2002 | Kamb et al. |
| 2002/0175079 A1 | 11/2002 | Christel et al. |
| 2002/0179849 A1 | 12/2002 | Maher et al. |
| 2002/0182118 A1 | 12/2002 | Perry |
| 2003/0005967 A1 | 1/2003 | Karp |
| 2003/0007898 A1 | 1/2003 | Bohm et al. |
| 2003/0008285 A1 | 1/2003 | Fischer |
| 2003/0008323 A1 | 1/2003 | Ravkin et al. |
| 2003/0022231 A1 | 1/2003 | Wangh et al. |
| 2003/0027203 A1 | 2/2003 | Fields |
| 2003/0027214 A1 | 2/2003 | Kamb |
| 2003/0027221 A1 | 2/2003 | Scott et al. |
| 2003/0028981 A1 | 2/2003 | Chandler et al. |
| 2003/0032141 A1 | 2/2003 | Nguyen et al. |
| 2003/0036206 A1 | 2/2003 | Chien et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0075446 A1 | 4/2003 | Culbertson et al. |
| 2003/0082587 A1 | 5/2003 | Seul et al. |
| 2003/0089605 A1 | 5/2003 | Timperman |
| 2003/0104466 A1 | 6/2003 | Knapp et al. |
| 2003/0108897 A1 | 6/2003 | Drmanac |
| 2003/0124509 A1 | 7/2003 | Kenis et al. |
| 2003/0149307 A1 | 8/2003 | Hai et al. |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |

(56) References Cited

U.S. PATENT DOCUMENTS

| | | |
|---|---|---|
| 2003/0215862 A1 | 11/2003 | Parce et al. |
| 2004/0021068 A1 | 2/2004 | Staats |
| 2004/0040851 A1 | 3/2004 | Karger et al. |
| 2004/0063138 A1 | 4/2004 | Mcginnis et al. |
| 2004/0081962 A1 | 4/2004 | Chen et al. |
| 2004/0101680 A1 | 5/2004 | Barber et al. |
| 2004/0101880 A1 | 5/2004 | Rozwadowski et al. |
| 2004/0132122 A1 | 7/2004 | Banerjee et al. |
| 2004/0195728 A1 | 10/2004 | Slomski et al. |
| 2004/0214175 A9 | 10/2004 | McKernan et al. |
| 2004/0224331 A1 | 11/2004 | Cantor et al. |
| 2004/0228770 A1 | 11/2004 | Gandhi et al. |
| 2004/0258701 A1 | 12/2004 | Dominowski et al. |
| 2005/0019839 A1 | 1/2005 | Jespersen et al. |
| 2005/0042625 A1 | 2/2005 | Schmidt et al. |
| 2005/0079510 A1 | 4/2005 | Berka et al. |
| 2005/0130188 A1 | 6/2005 | Walt et al. |
| 2005/0172476 A1 | 8/2005 | Stone et al. |
| 2005/0181379 A1 | 8/2005 | Su et al. |
| 2005/0202429 A1 | 9/2005 | Trau et al. |
| 2005/0202489 A1 | 9/2005 | Cho et al. |
| 2005/0221339 A1 | 10/2005 | Griffiths et al. |
| 2005/0244850 A1 | 11/2005 | Huang et al. |
| 2005/0266582 A1 | 12/2005 | Modlin et al. |
| 2005/0272159 A1 | 12/2005 | Ismagilov et al. |
| 2005/0287572 A1 | 12/2005 | Mathies et al. |
| 2006/0002890 A1 | 1/2006 | Hersel et al. |
| 2006/0008799 A1 | 1/2006 | Cai et al. |
| 2006/0020371 A1 | 1/2006 | Ham et al. |
| 2006/0040382 A1 | 2/2006 | Heffron et al. |
| 2006/0073487 A1 | 4/2006 | Oliver et al. |
| 2006/0078888 A1 | 4/2006 | Griffiths et al. |
| 2006/0094108 A1 | 5/2006 | Yoder et al. |
| 2006/0153924 A1 | 7/2006 | Griffiths et al. |
| 2006/0163070 A1 | 7/2006 | Boronkay et al. |
| 2006/0163385 A1 | 7/2006 | Link et al. |
| 2006/0177832 A1 | 8/2006 | Brenner |
| 2006/0177833 A1 | 8/2006 | Brenner |
| 2006/0199193 A1 | 9/2006 | Koo et al. |
| 2006/0240506 A1 | 10/2006 | Kushmaro et al. |
| 2006/0257893 A1 | 11/2006 | Takahashi et al. |
| 2006/0263888 A1 | 11/2006 | Fritz et al. |
| 2006/0275782 A1 | 12/2006 | Gunderson et al. |
| 2006/0286570 A1 | 12/2006 | Rowlen et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0020640 A1 | 1/2007 | McCloskey et al. |
| 2007/0031829 A1 | 2/2007 | Yasuno et al. |
| 2007/0039866 A1 | 2/2007 | Schroeder et al. |
| 2007/0042400 A1 | 2/2007 | Choi et al. |
| 2007/0042419 A1 | 2/2007 | Barany et al. |
| 2007/0054119 A1 | 3/2007 | Garstecki et al. |
| 2007/0072208 A1 | 3/2007 | Drmanac |
| 2007/0077572 A1 | 4/2007 | Tawfik et al. |
| 2007/0092914 A1 | 4/2007 | Griffiths et al. |
| 2007/0099208 A1 | 5/2007 | Drmanac et al. |
| 2007/0134277 A1 | 6/2007 | Chen et al. |
| 2007/0154903 A1 | 7/2007 | Marla et al. |
| 2007/0160503 A1 | 7/2007 | Sethu et al. |
| 2007/0172873 A1 | 7/2007 | Brenner et al. |
| 2007/0190543 A1 | 8/2007 | Livak |
| 2007/0195127 A1 | 8/2007 | Ahn et al. |
| 2007/0207060 A1 | 9/2007 | Zou et al. |
| 2007/0228588 A1 | 10/2007 | Noritomi et al. |
| 2007/0231823 A1 | 10/2007 | McKernan et al. |
| 2007/0238113 A1 | 10/2007 | Kanda et al. |
| 2007/0242111 A1 | 10/2007 | Pamula et al. |
| 2007/0259357 A1 | 11/2007 | Brenner |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2008/0056948 A1 | 3/2008 | Dale et al. |
| 2008/0124726 A1 | 5/2008 | Monforte |
| 2008/0138878 A1 | 6/2008 | Kubu et al. |
| 2008/0166720 A1 | 7/2008 | Hsieh et al. |
| 2008/0213766 A1 | 9/2008 | Brown et al. |
| 2008/0228268 A1 | 9/2008 | Shannon et al. |
| 2008/0230386 A1 | 9/2008 | Srinivasan et al. |
| 2008/0241820 A1 | 10/2008 | Krutzik et al. |
| 2008/0242560 A1 | 10/2008 | Gunderson et al. |
| 2008/0268450 A1 | 10/2008 | Nam et al. |
| 2009/0005252 A1 | 1/2009 | Drmanac et al. |
| 2009/0011943 A1 | 1/2009 | Drmanac et al. |
| 2009/0012187 A1 | 1/2009 | Chu et al. |
| 2009/0025277 A1 | 1/2009 | Takanashi |
| 2009/0035770 A1 | 2/2009 | Mathies et al. |
| 2009/0047713 A1 | 2/2009 | Handique |
| 2009/0048124 A1 | 2/2009 | Leamon et al. |
| 2009/0053169 A1 | 2/2009 | Castillo et al. |
| 2009/0068170 A1 | 3/2009 | Weitz et al. |
| 2009/0098555 A1 | 4/2009 | Roth et al. |
| 2009/0099041 A1 | 4/2009 | Church et al. |
| 2009/0105959 A1 | 4/2009 | Braverman et al. |
| 2009/0118488 A1 | 5/2009 | Drmanac et al. |
| 2009/0134027 A1 | 5/2009 | Jary |
| 2009/0137404 A1 | 5/2009 | Drmanac et al. |
| 2009/0137414 A1 | 5/2009 | Drmanac et al. |
| 2009/0143244 A1 | 6/2009 | Bridgham et al. |
| 2009/0148961 A1 | 6/2009 | Luchini et al. |
| 2009/0155780 A1 | 6/2009 | Xiao et al. |
| 2009/0155781 A1 | 6/2009 | Drmanac et al. |
| 2009/0197248 A1 | 8/2009 | Griffiths et al. |
| 2009/0197772 A1 | 8/2009 | Griffiths et al. |
| 2009/0202984 A1 | 8/2009 | Cantor |
| 2009/0203531 A1 | 8/2009 | Kurn |
| 2009/0208548 A1 | 8/2009 | Mason et al. |
| 2009/0264299 A1 | 10/2009 | Drmanac et al. |
| 2009/0269248 A1 | 10/2009 | Falb et al. |
| 2009/0286687 A1 | 11/2009 | Dressman et al. |
| 2009/0311713 A1 | 12/2009 | Pollack et al. |
| 2009/0320930 A1 | 12/2009 | Zeng et al. |
| 2010/0021973 A1 | 1/2010 | Makarov et al. |
| 2010/0021984 A1 | 1/2010 | Edd et al. |
| 2010/0022414 A1 | 1/2010 | Link et al. |
| 2010/0029014 A1 | 2/2010 | Wang |
| 2010/0035254 A1 | 2/2010 | Williams |
| 2010/0062494 A1 | 3/2010 | Church et al. |
| 2010/0069263 A1 | 3/2010 | Shendure et al. |
| 2010/0086914 A1 | 4/2010 | Bentley et al. |
| 2010/0105112 A1 | 4/2010 | Holtze et al. |
| 2010/0113296 A1 | 5/2010 | Myerson |
| 2010/0120098 A1 | 5/2010 | Grunenwald et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0184928 A1 | 7/2010 | Kumacheva |
| 2010/0187705 A1 | 7/2010 | Lee et al. |
| 2010/0210479 A1 | 8/2010 | Griffiths et al. |
| 2010/0248237 A1 | 9/2010 | Froehlich et al. |
| 2010/0248991 A1 | 9/2010 | Roesler et al. |
| 2010/0304982 A1 | 12/2010 | Hinz et al. |
| 2011/0000560 A1 | 1/2011 | Miller et al. |
| 2011/0008775 A1 | 1/2011 | Gao et al. |
| 2011/0028412 A1 | 2/2011 | Cappello et al. |
| 2011/0033548 A1 | 2/2011 | Lai et al. |
| 2011/0033854 A1 | 2/2011 | Drmanac et al. |
| 2011/0046243 A1 | 2/2011 | Ito et al. |
| 2011/0053798 A1 | 3/2011 | Hindson et al. |
| 2011/0059556 A1 | 3/2011 | Strey et al. |
| 2011/0071053 A1 | 3/2011 | Drmanac et al. |
| 2011/0086780 A1 | 4/2011 | Colston, Jr. et al. |
| 2011/0092376 A1 | 4/2011 | Colston, Jr. et al. |
| 2011/0092392 A1 | 4/2011 | Colston, Jr. et al. |
| 2011/0160078 A1 | 6/2011 | Fodor et al. |
| 2011/0195496 A1 | 8/2011 | Muraguchi et al. |
| 2011/0201526 A1 | 8/2011 | Berka et al. |
| 2011/0217736 A1 | 9/2011 | Hindson |
| 2011/0218123 A1 | 9/2011 | Weitz et al. |
| 2011/0263457 A1 | 10/2011 | Krutzik et al. |
| 2011/0267457 A1 | 11/2011 | Weitz et al. |
| 2011/0281736 A1 | 11/2011 | Drmanac et al. |

(56) References Cited

U.S. PATENT DOCUMENTS

| | | |
|---|---|---|
| 2011/0281738 A1 | 11/2011 | Drmanac et al. |
| 2011/0287435 A1 | 11/2011 | Grunenwald et al. |
| 2011/0305761 A1 | 12/2011 | Shum et al. |
| 2011/0306141 A1 | 12/2011 | Bronchetti et al. |
| 2011/0319281 A1 | 12/2011 | Drmanac |
| 2012/0000777 A1 | 1/2012 | Garrell et al. |
| 2012/0003657 A1 | 1/2012 | Myllykangas et al. |
| 2012/0010098 A1 | 1/2012 | Griffiths et al. |
| 2012/0010107 A1 | 1/2012 | Griffiths et al. |
| 2012/0014977 A1 | 1/2012 | Furihata et al. |
| 2012/0015382 A1 | 1/2012 | Weitz et al. |
| 2012/0015822 A1 | 1/2012 | Weitz et al. |
| 2012/0071331 A1 | 3/2012 | Casbon et al. |
| 2012/0121481 A1 | 5/2012 | Romanowsky et al. |
| 2012/0132288 A1 | 5/2012 | Weitz et al. |
| 2012/0135893 A1 | 5/2012 | Drmanac et al. |
| 2012/0165219 A1 | 6/2012 | Van et al. |
| 2012/0172259 A1 | 7/2012 | Rigatti et al. |
| 2012/0190032 A1 | 7/2012 | Ness et al. |
| 2012/0190037 A1 | 7/2012 | Durin et al. |
| 2012/0196288 A1 | 8/2012 | Beer et al. |
| 2012/0208705 A1 | 8/2012 | Steemers et al. |
| 2012/0208724 A1 | 8/2012 | Steemers et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2012/0231972 A1 | 9/2012 | Golyshin et al. |
| 2012/0252012 A1 | 10/2012 | Armougom et al. |
| 2012/0253689 A1 | 10/2012 | Rogan et al. |
| 2012/0297493 A1 | 11/2012 | Cooper et al. |
| 2012/0309002 A1 | 12/2012 | Link |
| 2012/0316074 A1 | 12/2012 | Saxonov et al. |
| 2012/0328488 A1 | 12/2012 | Puntambekar et al. |
| 2013/0017978 A1 | 1/2013 | Kavanagh et al. |
| 2013/0018970 A1 | 1/2013 | Woundy et al. |
| 2013/0022682 A1 | 1/2013 | Lee et al. |
| 2013/0028812 A1 | 1/2013 | Prieto et al. |
| 2013/0041004 A1 | 2/2013 | Drager et al. |
| 2013/0046030 A1 | 2/2013 | Rotem et al. |
| 2013/0059310 A1 | 3/2013 | Brenner et al. |
| 2013/0078638 A1 | 3/2013 | Berka et al. |
| 2013/0079231 A1 | 3/2013 | Pushkarev et al. |
| 2013/0084243 A1 | 4/2013 | Goetsch et al. |
| 2013/0096073 A1 | 4/2013 | Sidelman |
| 2013/0109575 A1 | 5/2013 | Kleinschmidt et al. |
| 2013/0109576 A1 | 5/2013 | Shuber et al. |
| 2013/0121893 A1 | 5/2013 | Delamarche et al. |
| 2013/0130919 A1 | 5/2013 | Chen et al. |
| 2013/0157870 A1 | 6/2013 | Pushkarev et al. |
| 2013/0157899 A1 | 6/2013 | Adler, Jr. et al. |
| 2013/0178368 A1 | 7/2013 | Griffiths et al. |
| 2013/0189700 A1 | 7/2013 | So et al. |
| 2013/0203605 A1 | 8/2013 | Shendure et al. |
| 2013/0203675 A1 | 8/2013 | Desimone et al. |
| 2013/0210639 A1 | 8/2013 | Link et al. |
| 2013/0210991 A1 | 8/2013 | Fonnum et al. |
| 2013/0211055 A1 | 8/2013 | Raines et al. |
| 2013/0225418 A1 | 8/2013 | Watson |
| 2013/0225623 A1 | 8/2013 | Buxbaum et al. |
| 2013/0274117 A1 | 10/2013 | Church et al. |
| 2013/0293246 A1 | 11/2013 | Pollack et al. |
| 2013/0296173 A1 | 11/2013 | Callow et al. |
| 2013/0343317 A1 | 12/2013 | Etemad et al. |
| 2014/0030350 A1 | 1/2014 | Ashrafi et al. |
| 2014/0037514 A1 | 2/2014 | Stone et al. |
| 2014/0038178 A1 | 2/2014 | Otto et al. |
| 2014/0057799 A1 | 2/2014 | Johnson et al. |
| 2014/0065234 A1 | 3/2014 | Shum et al. |
| 2014/0093916 A1 | 4/2014 | Belyaev et al. |
| 2014/0120529 A1 | 5/2014 | Andersen et al. |
| 2014/0155274 A1 | 6/2014 | Xie et al. |
| 2014/0155295 A1 | 6/2014 | Hindson et al. |
| 2014/0194323 A1 | 7/2014 | Gillevet et al. |
| 2014/0199730 A1 | 7/2014 | Agresti et al. |
| 2014/0199731 A1 | 7/2014 | Agresti et al. |
| 2014/0206554 A1 | 7/2014 | Hindson et al. |
| 2014/0227684 A1 | 8/2014 | Hindson et al. |
| 2014/0227706 A1 | 8/2014 | Kato et al. |
| 2014/0228255 A1 | 8/2014 | Hindson et al. |
| 2014/0235506 A1 | 8/2014 | Hindson et al. |
| 2014/0242664 A1 | 8/2014 | Zhang et al. |
| 2014/0248621 A1* | 9/2014 | Collins ............... G01N 15/1056 435/6.12 |
| 2014/0272958 A1* | 9/2014 | Ramsey ............ B01L 3/502715 435/6.11 |
| 2014/0274740 A1 | 9/2014 | Srinivasan et al. |
| 2014/0287963 A1 | 9/2014 | Hindson et al. |
| 2014/0302503 A1 | 10/2014 | Lowe et al. |
| 2014/0315725 A1 | 10/2014 | Faham et al. |
| 2014/0315755 A1 | 10/2014 | Chen et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005188 A1 | 1/2015 | Levner et al. |
| 2015/0005199 A1 | 1/2015 | Hindson et al. |
| 2015/0005200 A1 | 1/2015 | Hindson et al. |
| 2015/0011430 A1 | 1/2015 | Saxonov |
| 2015/0011432 A1 | 1/2015 | Saxonov et al. |
| 2015/0057163 A1 | 2/2015 | Rotem et al. |
| 2015/0072899 A1 | 3/2015 | Ward et al. |
| 2015/0111256 A1 | 4/2015 | Church et al. |
| 2015/0111788 A1 | 4/2015 | Fernandez et al. |
| 2015/0114093 A1* | 4/2015 | Appleyard ........ B01L 3/502761 73/61.59 |
| 2015/0119280 A1 | 4/2015 | Srinivas et al. |
| 2015/0196909 A1* | 7/2015 | Jones ................ B01L 3/502738 137/613 |
| 2015/0218633 A1 | 8/2015 | Hindson et al. |
| 2015/0224466 A1 | 8/2015 | Hindson et al. |
| 2015/0225777 A1 | 8/2015 | Hindson et al. |
| 2015/0258543 A1 | 9/2015 | Baroud et al. |
| 2015/0259736 A1 | 9/2015 | Steemers et al. |
| 2015/0267191 A1 | 9/2015 | Steelman et al. |
| 2015/0267246 A1 | 9/2015 | Baroud et al. |
| 2015/0291942 A1 | 10/2015 | Gloeckner et al. |
| 2015/0298091 A1 | 10/2015 | Weitz et al. |
| 2015/0299772 A1 | 10/2015 | Zhang |
| 2015/0299784 A1 | 10/2015 | Fan et al. |
| 2015/0329891 A1 | 11/2015 | Tan et al. |
| 2015/0337298 A1 | 11/2015 | Xi et al. |
| 2015/0353999 A1 | 12/2015 | Agresti et al. |
| 2015/0361418 A1 | 12/2015 | Reed et al. |
| 2015/0367344 A1* | 12/2015 | Kumaran ............ B01F 11/0051 422/502 |
| 2015/0368638 A1 | 12/2015 | Steemers et al. |
| 2015/0376605 A1 | 12/2015 | Jarosz et al. |
| 2015/0376608 A1 | 12/2015 | Kaper et al. |
| 2015/0376609 A1 | 12/2015 | Hindson et al. |
| 2015/0376700 A1 | 12/2015 | Schnall-Levin et al. |
| 2015/0379196 A1 | 12/2015 | Schnall-Levin et al. |
| 2016/0024558 A1 | 1/2016 | Hardenbol |
| 2016/0032282 A1 | 2/2016 | Vigneault et al. |
| 2016/0053253 A1 | 2/2016 | Salathia et al. |
| 2016/0060621 A1 | 3/2016 | Agresti et al. |
| 2016/0115474 A1 | 4/2016 | Jelinek et al. |
| 2016/0121331 A1* | 5/2016 | Kapur ................... A61K 35/28 435/309.1 |
| 2016/0122753 A1 | 5/2016 | Mikkelsen et al. |
| 2016/0122817 A1 | 5/2016 | Jarosz et al. |
| 2016/0123857 A1* | 5/2016 | Kapur ............ B01L 3/502753 435/2 |
| 2016/0123858 A1 | 5/2016 | Kapur et al. |
| 2016/0153005 A1 | 6/2016 | Zhang et al. |
| 2016/0160235 A1 | 6/2016 | Solodushko et al. |
| 2016/0177359 A1 | 6/2016 | Ukanis et al. |
| 2016/0208323 A1 | 7/2016 | Bernstein et al. |
| 2016/0231324 A1 | 8/2016 | Zhao et al. |
| 2016/0244742 A1 | 8/2016 | Linnarsson et al. |
| 2016/0244809 A1 | 8/2016 | Belgrader et al. |
| 2016/0244825 A1 | 8/2016 | Vigneault et al. |
| 2016/0257984 A1 | 9/2016 | Hardenbol et al. |

(56) References Cited

U.S. PATENT DOCUMENTS

| | | |
|---|---|---|
| 2016/0281160 A1 | 9/2016 | Jarosz et al. |
| 2016/0304860 A1 | 10/2016 | Hindson et al. |
| 2016/0326583 A1 | 11/2016 | Johnson et al. |
| 2016/0348093 A1 | 12/2016 | Price et al. |
| 2016/0376663 A1 | 12/2016 | Brown |
| 2017/0009274 A1 | 1/2017 | Abate et al. |
| 2017/0016041 A1 | 1/2017 | Greenfield et al. |
| 2017/0114390 A1 | 4/2017 | Hindson et al. |
| 2017/0145476 A1 | 5/2017 | Ryvkin et al. |
| 2017/0183701 A1 | 6/2017 | Agresti et al. |
| 2017/0247757 A1 | 8/2017 | Hindson et al. |
| 2017/0260584 A1 | 9/2017 | Zheng et al. |
| 2017/0268056 A1 | 9/2017 | Vigneault et al. |
| 2017/0321252 A1 | 11/2017 | Hindson et al. |
| 2017/0348691 A1 | 12/2017 | Bharadwaj et al. |
| 2017/0356027 A1 | 12/2017 | Hindson et al. |
| 2018/0008984 A1 | 1/2018 | Bharadwaj et al. |
| 2018/0015472 A1 | 1/2018 | Bharadwaj et al. |
| 2018/0015473 A1 | 1/2018 | Bharadwaj et al. |
| 2018/0016634 A1 | 1/2018 | Hindson et al. |
| 2018/0030512 A1 | 2/2018 | Hindson et al. |
| 2018/0030515 A1 | 2/2018 | Regev et al. |
| 2018/0051321 A1 | 2/2018 | Hindson et al. |
| 2018/0057868 A1 | 3/2018 | Walder et al. |
| 2018/0087050 A1 | 3/2018 | Zheng et al. |
| 2018/0094298 A1 | 4/2018 | Hindson et al. |
| 2018/0094313 A1 | 4/2018 | Hindson |
| 2018/0094315 A1 | 4/2018 | Hindson et al. |
| 2018/0105808 A1 | 4/2018 | Mikkelsen et al. |
| 2018/0112253 A1 | 4/2018 | Hindson et al. |
| 2018/0112266 A1 | 4/2018 | Hindson et al. |
| 2018/0179580 A1 | 6/2018 | Hindson et al. |
| 2018/0195112 A1 | 7/2018 | Lebofsky et al. |
| 2018/0216162 A1 | 8/2018 | Belhocine et al. |
| 2018/0236443 A1 | 8/2018 | Masquelier et al. |
| 2018/0258466 A1 | 9/2018 | Hindson et al. |
| 2018/0258482 A1 | 9/2018 | Hindson et al. |
| 2018/0265928 A1 | 9/2018 | Schnall-Levin et al. |
| 2018/0273933 A1 | 9/2018 | Gunderson et al. |
| 2018/0274027 A1 | 9/2018 | Hindson et al. |
| 2018/0282804 A1 | 10/2018 | Hindson et al. |
| 2018/0327839 A1 | 11/2018 | Hindson et al. |
| 2018/0340939 A1 | 11/2018 | Gaublomme et al. |
| 2019/0134633 A1 | 5/2019 | Bharadwaj et al. |
| 2022/0080424 A1 | 3/2022 | Akhremichev et al. |

FOREIGN PATENT DOCUMENTS

| | | |
|---|---|---|
| EP | 0249007 A2 | 12/1987 |
| EP | 0271281 A2 | 6/1988 |
| EP | 0637996 B1 | 7/1997 |
| EP | 1019496 B1 | 9/2004 |
| EP | 1672064 A1 | 6/2006 |
| EP | 1482036 B1 | 10/2007 |
| EP | 1841879 A2 | 10/2007 |
| EP | 1594980 B1 | 11/2009 |
| EP | 1967592 B1 | 4/2010 |
| EP | 2258846 A2 | 12/2010 |
| EP | 2145955 B1 | 2/2012 |
| EP | 1905828 B1 | 8/2012 |
| EP | 2136786 B1 | 10/2012 |
| EP | 1908832 B1 | 12/2012 |
| EP | 2540389 A1 | 1/2013 |
| EP | 2635679 A1 | 9/2013 |
| EP | 2752664 A1 | 7/2014 |
| GB | 2097692 B | 5/1985 |
| GB | 2485850 A | 5/2012 |
| JP | S5949832 A | 3/1984 |
| JP | S60227826 A | 11/1985 |
| JP | 2006507921 A | 3/2006 |
| JP | 2006289250 A | 10/2006 |
| JP | 2007015990 A | 1/2007 |
| JP | 2007268350 A | 10/2007 |
| JP | 2009513948 A | 4/2009 |
| JP | 2009208074 A | 9/2009 |
| JP | 2012131798 A | 7/2012 |
| WO | WO-8402000 A1 | 5/1984 |
| WO | WO-9418218 A1 | 8/1994 |
| WO | WO-9419101 A1 | 9/1994 |
| WO | WO-9423699 A1 | 10/1994 |
| WO | WO-9530782 A1 | 11/1995 |
| WO | WO-9629629 A2 | 9/1996 |
| WO | WO-9641011 A1 | 12/1996 |
| WO | WO-9802237 A1 | 1/1998 |
| WO | WO-9852691 A1 | 11/1998 |
| WO | WO-9909217 A1 | 2/1999 |
| WO | WO-9952708 A1 | 10/1999 |
| WO | WO-0008212 A1 | 2/2000 |
| WO | WO-0023181 A1 | 4/2000 |
| WO | WO-0026412 A1 | 5/2000 |
| WO | WO-0043766 A1 | 7/2000 |
| WO | WO-0070095 A2 | 11/2000 |
| WO | WO-0102850 A1 | 1/2001 |
| WO | WO-0114589 A2 | 3/2001 |
| WO | WO-0189787 A2 | 11/2001 |
| WO | WO-0190418 A1 | 11/2001 |
| WO | WO-0127610 A3 | 3/2002 |
| WO | WO-0231203 A2 | 4/2002 |
| WO | WO-02086148 A1 | 10/2002 |
| WO | WO-0218949 A3 | 1/2003 |
| WO | WO-03062462 A2 | 7/2003 |
| WO | WO-2004002627 A2 | 1/2004 |
| WO | WO-2004010106 A2 | 1/2004 |
| WO | WO-2004061083 A2 | 7/2004 |
| WO | WO-2004065617 A2 | 8/2004 |
| WO | WO-2004069849 A2 | 8/2004 |
| WO | WO-2004091763 A2 | 10/2004 |
| WO | WO-2004102204 A1 | 11/2004 |
| WO | WO-2004103565 A2 | 12/2004 |
| WO | WO-2004105734 A1 | 12/2004 |
| WO | WO-2005002730 A1 | 1/2005 |
| WO | WO-2005021151 A1 | 3/2005 |
| WO | WO-2005023331 A2 | 3/2005 |
| WO | WO-2005040406 A1 | 5/2005 |
| WO | WO-2005049787 A2 | 6/2005 |
| WO | WO-2005082098 A2 | 9/2005 |
| WO | WO-2006030993 A1 | 3/2006 |
| WO | WO-2006078841 A1 | 7/2006 |
| WO | WO-2006096571 A2 | 9/2006 |
| WO | WO-2007001448 A2 | 1/2007 |
| WO | WO-2007002490 A2 | 1/2007 |
| WO | WO-2007012638 A1 | 2/2007 |
| WO | WO-2007018601 A1 | 2/2007 |
| WO | WO-2007024840 A2 | 3/2007 |
| WO | WO-2007081385 A2 | 7/2007 |
| WO | WO-2007081387 A1 | 7/2007 |
| WO | WO-2007084192 A2 | 7/2007 |
| WO | WO-2007089541 A2 | 8/2007 |
| WO | WO-2007093819 A2 | 8/2007 |
| WO | WO-2007111937 A1 | 10/2007 |
| WO | WO-2007114794 A1 | 10/2007 |
| WO | WO-2007121489 A2 | 10/2007 |
| WO | WO-2007133710 A2 | 11/2007 |
| WO | WO-2007138178 A2 | 12/2007 |
| WO | WO-2007139766 A2 | 12/2007 |
| WO | WO-2007140015 A2 | 12/2007 |
| WO | WO-2007147079 A2 | 12/2007 |
| WO | WO-2007149432 A2 | 12/2007 |
| WO | WO-2008021123 A1 | 2/2008 |
| WO | WO-2008091792 A2 | 7/2008 |
| WO | WO-2008102057 A1 | 8/2008 |
| WO | WO-2008109176 A2 | 9/2008 |
| WO | WO-2008121342 A2 | 10/2008 |
| WO | WO-2008061193 A3 | 11/2008 |
| WO | WO-2008134153 A1 | 11/2008 |
| WO | WO-2008150432 A1 | 12/2008 |
| WO | WO-2009005680 A1 | 1/2009 |
| WO | WO-2009011808 A1 | 1/2009 |
| WO | WO-2009015296 A1 | 1/2009 |
| WO | WO-2009048532 A2 | 4/2009 |
| WO | WO-2009061372 A1 | 5/2009 |
| WO | WO-2009085215 A1 | 7/2009 |
| WO | WO-2009147386 A1 | 12/2009 |
| WO | WO-2010004018 A2 | 1/2010 |

(56) References Cited

FOREIGN PATENT DOCUMENTS

| | | |
|---|---|---|
| WO | WO-2010014604 A1 | 2/2010 |
| WO | WO-2010033200 A2 | 3/2010 |
| WO | WO-2010048605 A1 | 4/2010 |
| WO | WO-2010104604 A1 | 9/2010 |
| WO | WO-2010115154 A1 | 10/2010 |
| WO | WO-2010148039 A2 | 12/2010 |
| WO | WO-2010151776 A2 | 12/2010 |
| WO | WO-2010117620 A3 | 2/2011 |
| WO | WO-2011028539 A1 | 3/2011 |
| WO | WO-2011047870 A1 | 4/2011 |
| WO | WO-2011056546 A1 | 5/2011 |
| WO | WO-2011066476 A1 | 6/2011 |
| WO | WO-2011074960 A1 | 6/2011 |
| WO | WO-2011140627 A1 | 11/2011 |
| WO | WO-2012012037 A1 | 1/2012 |
| WO | WO-2012019765 A1 | 2/2012 |
| WO | WO-2012047889 A2 | 4/2012 |
| WO | WO-2012048340 A2 | 4/2012 |
| WO | WO-2012048341 A1 | 4/2012 |
| WO | WO-2012061832 A1 | 5/2012 |
| WO | WO-2012083225 A2 | 6/2012 |
| WO | WO-2012106546 A2 | 8/2012 |
| WO | WO-2012112804 A1 | 8/2012 |
| WO | WO-2012112970 A2 | 8/2012 |
| WO | WO-2012136734 A1 | 10/2012 |
| WO | WO-2012142611 A2 | 10/2012 |
| WO | WO-2012148497 A2 | 11/2012 |
| WO | WO-2012149042 A2 | 11/2012 |
| WO | WO-2012166425 A2 | 12/2012 |
| WO | WO-2013019751 A1 | 2/2013 |
| WO | WO-2013036929 A1 | 3/2013 |
| WO | WO-2013055955 A1 | 4/2013 |
| WO | WO-2013062485 A1 * 5/2013 ............ C12M 23/16 |
| WO | WO-2013096643 A1 | 6/2013 |
| WO | WO-2013122996 A1 | 8/2013 |
| WO | WO-2013123125 A1 | 8/2013 |
| WO | WO-2013126741 A1 | 8/2013 |
| WO | WO-2013134261 A1 | 9/2013 |
| WO | WO-2013150083 A1 | 10/2013 |
| WO | WO-2013177220 A1 | 11/2013 |
| WO | WO-2013188872 A1 | 12/2013 |
| WO | WO-2014028537 A1 | 2/2014 |
| WO | WO-2014053854 A1 | 4/2014 |
| WO | WO-2014071361 A1 | 5/2014 |
| WO | WO-2014074611 A1 | 5/2014 |
| WO | WO-2014093676 A1 | 6/2014 |
| WO | WO-2014108810 A2 | 7/2014 |
| WO | WO-2014140309 A1 | 9/2014 |
| WO | WO-2014144495 A1 | 9/2014 |
| WO | WO-2014150931 A1 | 9/2014 |
| WO | WO-2014182835 A1 | 11/2014 |
| WO | WO-2014189957 A2 | 11/2014 |
| WO | WO-2014210353 A2 | 12/2014 |
| WO | WO-2015031691 A1 | 3/2015 |
| WO | WO-2015044428 A1 | 4/2015 |
| WO | WO-2015061458 A1 * 4/2015 ............ B01L 3/5027 |
| WO | WO-2015164212 A1 | 10/2015 |
| WO | WO-2016019393 A1 * 2/2016 ........ B01L 3/502746 |
| WO | WO-2016040476 A1 | 3/2016 |
| WO | WO-2016061517 A2 | 4/2016 |
| WO | WO-2016126871 A2 | 8/2016 |
| WO | WO-2016170126 A1 | 10/2016 |
| WO | WO-2016176322 A1 | 11/2016 |
| WO | WO-2016187717 A1 | 12/2016 |
| WO | WO-2016191618 A1 | 12/2016 |
| WO | WO-2016207647 A1 | 12/2016 |
| WO | WO-2016207653 A1 | 12/2016 |
| WO | WO-2016207661 A1 | 12/2016 |
| WO | WO-2017015075 A1 | 1/2017 |
| WO | WO-2017025594 A1 | 2/2017 |
| WO | WO-2017053902 A1 | 3/2017 |
| WO | WO-2017053903 A1 | 3/2017 |
| WO | WO-2017053905 A1 | 3/2017 |
| WO | WO-2017075265 A1 | 5/2017 |
| WO | WO-2017156336 A1 | 9/2017 |
| WO | WO-2018045186 A1 | 3/2018 |
| WO | WO-2018119301 A1 | 6/2018 |
| WO | WO-2018191701 A1 | 10/2018 |
| WO | WO-2019028166 A1 | 2/2019 |

OTHER PUBLICATIONS

Sousa et al. (High performance microfluidic rectifiers for viscoelastic fluid flow, RSC Advances, 2012, vol. 2, pp. 920-929, see attached document) (Year: 2012).*
Abate, et al. Beating Poisson encapsulation statistics using close-packed ordering. Lab Chip. Sep. 21, 2009;9(18):2628-31. doi: 10.1039/b909386a. Epub Jul. 28, 2009.
Abate, et al. High-throughput injection with microfluidics using picoinjectors. Proc Natl Acad Sci U S A. Nov. 9, 2010;107(45):19163-6. doi: 10.1073/pNas.1006888107. Epub Oct. 20, 2010.
Abate et al., Valve-based flow focusing for drop formation. Appl Phys Lett. 2009;94. 3 pages.
Abate et al., Syringe-vacuum microfluidics: A portable technique to create monodisperse emulsions, Biomicrofluidics 5, 014107 (2011).
Adamson et al., "Production of arrays of chemically distinct nanolitre plugs via repeated splitting in microfluidic devices", Lab Chip 6(9): 1178-1186 (Sep. 2006).
Agresti, et al. Selection of ribozymes that catalyse multiple-turnover Diels-Alder cycloadditions by using in vitro compartmentalization. Proc Natl Acad Sci U S A. Nov. 8, 2005;102(45):16170-5. Epub Oct. 31, 2005.
Agresti, et al., "Ultra-high-throughput screening in drop-based microfluidics for directed evolution", vol. 107, No. 9 (Mar. 2, 2010).
Ahn et al., "Dielectrophoretic manipulation of drops for high-speed microfluidic sorting devices", Applied Physics Letter, 88 (2006).
"Ahn K, et al.; Electrocoalescence of drops synchronized by size-dependent flow in microfluidic channels. Appl Phys Lett 88; (2006); pp. 264105-1-264105-3."
Akselband, "Enrichment of slow-growing marine microorganisms from mixed cultures using gel microdrop (GMD) growth assay and fluorescence-activated cell sorting", J. Exp. Marine Bioi., 329: 196-205 (2006).
Akselband, "Rapid mycobacteria drug susceptibility testing using gel microdrop (GMD) growth assay and flow cytometry", J. Microbiol. Methods, 62:181-197 (2005).
Ali-Cherif et al., "Programmable Magnetic Tweezers and Droplet Microfluidic Device for High-Throughput Nanoliter Multi-Step Assays", Angew. Chem. Int. Ed. 51, 10765-10769 (2012).
Anna, S.L., et al., "Formation of dispersions using "flow focusing" in microchannels," Applied Physics Letters, vol. 82, No. 3, pp. 364-366 (2003).
Attia, et al. Micro-injection moulding of polymer microfluidic devices. Microfluidics and nanofluidics. 2009; 7(1):1-28.
Bardin et al., "High-speed, clinical-scale microfluidic generation of stable phase-change droplets for gas embolotherapy", Lab Chip, Vo.11, 3990-3998 (2011).
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
Baret et al., Kinetic aspects of emulsion stabilization by surfactants: a microfluidic analysis, Langmuir 25:6088-6093 (2009).
Becker et al., "Polymer Microfabrication Technologies for Microfluidic", vol. 390, Issue 1, pp. 89-111 (Jan. 2008).
Belder "Microfluidics with Droplets", Angew. Chem. Int. Ed., 44, 3521-3522, (2005).
Bilotkach et al., "Fabrication of PDMS Membranes with Aqueous Molds for Microfluidic Systems", 12th Int'l Conference Miniaturized Sys. for Chemistry and Life Scis. (2008).
Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al., Scanning the Code. Modern Drug Discovery. 2003:28-32.

(56) References Cited

OTHER PUBLICATIONS

Bransky, et al. A microfluidic droplet generator based on a piezoelectric actuator. Lab Chip. Feb. 21, 2009;9(4):516-20. doi: 10.1039/b814810d. Epub Nov. 20, 2008.
Brenner, et al., "Injection Molding of Microfluidic Chips by Epoxy-Based Master Tools" (Oct. 9, 2005).
Brody, et al. Biotechnology at Low Reynolds Nos. Biophys J. 1996; 71:3430-3441.
Brouzes, et al. Droplet microfluidic technology for single-cell high-throughput screening. Proc Natl Acad Sci U S A. Aug. 25, 2009;106(34):14195-200. doi: 10.1073/pnas.0903542106. Epub Jul. 15, 2009.
Burns, et al. An Integrated Nanoliter DNA Analysis Device. Science. Oct. 16, 1998;282(5388):484-7.
Burns, et al. Microfabricated structures for integrated DNA analysis. Proc Natl Acad Sci U S A. May 28, 1996; 93(11): 5556-5561.
Burns, et al. The intensification of rapid reactions in multiphase systems using slug flow in capillaries. Lab Chip. Sep. 2001;1(1):10-5. Epub Aug. 9, 2001.
Carroll, "The selection of high-producing cell lines using flow cytometry and cell sorting", Exp. Op. Bioi. Therp., 4:11 1821-1829 (2004).
Chan et al., "High-Temperature Microfluidic Synthesis of CdSe Nanocrystals in Nanoliter Droplets", J. Am. Soc., 127, 13854-13861 (Oct. 12, 2005).
Chang et al. Droplet-based microfluidic platform for heterogeneous enzymatic assays, 2013, Lab Chip, 13, 1817-1822 (Year: 2013).
Chaudhary "A rapid method of cloning functional variable-region antibody genes in Escherichia coli as single-chain immunotoxins" Proc. Natl. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101.
Chen, et al. Chemical transfection of cells in picoliter aqueous droplets in fluorocarbon oil. Anal Chem. Nov. 1, 20115;83(22):8816-20. doi: 10.1021/ac2022794. Epub Oct. 17, 2011.
Chien et al. "Multiport flow-control system for lab-on-a-chip microfluidic devices", Fresenius J. Anal Chem, 371:106-111 (Jul. 27, 2001).
Chokkalingam, et al. Probing cellular heterogeneity in cytokine-secreting immune cells using droplet-based microfluidics. Lab Chip. Dec. 21, 2013;13(24):4740-4. doi: 10.1039/c3lc50945a.
Chou, et al. Disposable Microdevices for DNA Analysis and Cell Sorting. Proc. Solid-State Sensor and Actuator Workshop, Hilton Head, SC. Jun. 8-11, 1998; 11-14.
Christopher et al., "Microfluidic methods for generating continuous droplet streams", J. Phys. D: Appl. Phys. 40, R319-R336 (2007).
Chu, et al. Controllable monodisperse multiple emulsions. Angew Chem Int Ed Engl. 2007;46(47):8970-4.
Clausell-Tormos et al., "Droplet-based microfluidic platforms for the encapsulation and screening of mammalian cells and multicellular organisms", Chem. Biol. 15:427-437 (2008).
Co-pending U.S. Appl. No. 16/180,356, filed Nov. 5, 2018.
Curcio. Improved Techniques for High-Throughput Molecular Diagnostics. PHD Thesis. 2002.
Damean, et al. Simultaneous measurement of reactions in microdroplets filled by concentration gradients. Lab Chip. Jun. 21, 2009;9(12):1707-13. doi: 10.1039/b821021g. Epub Mar. 19, 2009.
Dangla, et al. Droplet microfluidics driven by gradients of confinement. Proc Natl Acad Sci U S A. Jan. 15, 2013; 110(3): 853-858. Published online Jan. 2, 2013. doi: 10.1073/pnas.1209186110.
De Bruin et al., UBS Investment Research. Q-Series®: DNA Sequencing. UBS Securities LLC. Jul. 12, 2007. 15 pages.
Demirci, et al. Single cell epitaxy by acoustic picolitre droplets. Lab Chip. Sep. 2007;7(9):1139-45. Epub Jul. 10, 2007.
Dendukuri et al., "Controlled synthesis of nonspherical microparticles Using Microfluidics", Langmuir, 21, 2113-2116 (Feb. 11, 2005).
Doerr, "The smallest bioreactor", Nature Methods, 2:5 326 (2005).

Dowding, et al. Oil core/polymer shell microcapsules by internal phase separation from emulsion droplets. II: controlling the release profile of active molecules. Langmuir. Jun. 7, 2005;21(12):5278-84.
Draper, et al. Compartmentalization of electrophoretically separated analytes in a multiphase microfluidic platform. Anal Chem. Jul. 3, 2012;84(13):5801-8. doi: 10.1021/ac301141x. Epub Jun. 13, 2012.
Dressler, et al. Droplet-based microfluidics enabling impact on drug discovery. J Biomol Screen. Apr. 2014;19(4):483-96. doi: 10.1177/1087057113510401. Epub Nov. 15, 2013.
Drmanac et al., Sequencing by hybridization (SBH): advantages, achievements, and opportunities. Adv Biochem Eng Biotechnol. 2002;77 :75-101.
Droplet Based Sequencing (slides) dated (Mar. 12, 2008).
Duffy, et al. Rapid Prototyping of Microfluidic Systems in Poly(dimethylsiloxane). Anal Chem. Dec. 1, 1998;70(23):4974-84. doi: 10.1021/ac980656z.
Eastburn, et al. Ultrahigh-throughput mammalian single-cell reverse-transcriptase polymerase chain reaction in microfluidic droplets. Anal Chem. Aug. 20, 2013;85(16):8016-21. doi: 10.1021/ac402057q. Epub Aug. 8, 2013.
Engl, et al., "Controlled production of emulsions and particles by milli- and microfluidic techniques", Current Opinion in Colloid and Interface Science, vol. 13, 206-216 (Sep. 26, 2007).
Erbacher et al., "Towards Integrated Continuous-Flow Chemical Reactors", Mikrochimica Acta, 131, pp. 19-24 (1999).
Esser-Kahn, et al. Triggered release from polymer capsules. Macromolecules. 2011; 44:5539-5553.
Ferraro et al., Microfluidic platform combining droplets and magnetic tweezers: application to HER2 expression in cancer diagnosis, Scientific Reports 6:25540 (May 9, 2016).
Fisher, et al. A scalable, fully automated process for construction of sequence-ready human exome targeted capture libraries. Genome Biol. 2011;12(1):R1. doi: 10.1186/GB-2011-12-1-r1. Epub Jan. 4, 2011.
Fredrickson, et al. Macro-to-micro interfaces for microfluidic devices. Lab Chip. Dec. 2004;4(6):526-33. Epub Nov. 10, 2004.
Freiberg, et al. Polymer microspheres for controlled drug release. Int J Pharm. Sep. 10, 2004;282(1-2):1-18.
Fu, et al. A Microfabricated Fluorescence-Activated Cell Sorter. Nature Biotechnology. 1999; 17:1109-1111.
Fulton, et al. Advanced multiplexed analysis with the FlowMetrix system. Clin Chem. Sep. 1997;43(9):1749-56.
Garstecki, et al. Formation of monodisperse bubbles in a microfluidic flow-focusing device. Applied Physics Letters. 2004; 85(13):2649-2651. DOI: 10.1063/1.1796526.
Garstecki et al., "Mechanism for Flow-Rate Controlled Breakup in Confined Geometries: A Route to Monodisperse Emulsions", PRL 94, 164501 (Apr. 27, 2005).
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Ghadessy, et al. Directed evolution of polymerase function by compartmentalized self-replication. Proc Natl Acad Sci USA. 2001;98:4552-4557.
Granieri, Lucia. Droplet-based microfluidics and engineering of tissue plasminogen activator for biomedical applications. Ph.D. Thesis, Nov. 13, 2009 (131 pages).
Grasland-Mongrain, et al. Droplet coalescence in microfluidic devices. Jan.-Jul. 2003. 31 pages. http://www.eleves.ens.fr/home/grasland/rapports/stage4.pdf.
Guo, et al. Droplet microfluidics for high-throughput biological assays. Lab Chip. Jun. 21, 2012;12(12):2146-55. doi: 10.1039/c2lc21147e. Epub Feb. 9, 2012.
Gyarmati, et al. Reversible disulphide formation in polymer networks: a versatile functional group from synthesis to applications. European Polymer Journal. 2013; 49:1268-1286.
Hashimshony, et al. CEL-Seq: Single-Cell RNA-Seq by Multiplexed Linear Amplification. Cell Rep. Sep. 27, 2012;2(3):666-73. doi: 10.1016/j.celrep.2012.08.003. Epub Aug. 30, 2012.
He, "Selective Encapsulation of Single Cells and Subcellular Organelles into Picoliter- and Femtoliter-Volume Droplets" Anal. Chem 77: 1539-1544 (2005).

(56) References Cited

OTHER PUBLICATIONS

Hettiarachchi et al., "Controllable microfluidic synthesis of multiphase drug-carrying liposheres for site-targeted therapy", American Inst. of Chem. Engineers (May 19, 2009).
Holtze, et al. Biocompatible surfactants for water-in-fluorocarbon emulsions. Lab Chip. Oct. 2008;8(10):1632-9. doi: 10.1039/b806706f. Epub Sep. 2, 2008.
Hosokawa, et al. Massively parallel whole genome amplification for single-cell sequencing using droplet microfluidics. Scientific Reports 7, Article No. 5199 (2017).
"Huebner et al., "Microdroplets: A sea of applications?"; Lab on a Chip, 8; (2008); pp. 1244-1254, 2008".
Huebner, "Quantitative detection of protein expression in single cells using droplet microfluidics", Chem. Commun. 1218-1220 (2007).
Hug, et al. Measurement of the number of molecules of a single mRNA species in a complex mRNA preparation. J Theor Biol. Apr. 21, 2003;221(4):615-24.
Hung, et al., "Alternating droplet generation and controlled dynamic droplet fusion in microfluidic device for Cds nanoparticle synthesis" (Jan. 5, 2006).
Hung et al., "PLGA micro/nanosphere synthesis by droplet microfluidic solvent evaporation and extraction approaches", Lab chip, vol. 10, 1820-1825 (May 14, 2010).
Ivanova et al., "Droplet Formation in a Thin Layer of a Two-Component Solution under the Thermal Action of Laser Radiation", Colloid Journal, vol. 69, No. 6, pp. 735-740 (Feb. 19, 2007).
Jeffries et al., "Controlled Shrinkage and Re-expansion of a Single Aqueous Droplet inside an Optical Vortex Trap", , J. Phys. Chem. B, 2007, 111 (11), pp. 2806-2812.
Jeffries et al., "Dynamic modulation of chemical concentration in an aqueous droplet", Angew. Chem. Int. Ed., 1326-1328 (2007).
Jena, et al. Cyclic olefin copolymer based microfluidic devices for biochip applications: Ultraviolet surface grafting using 2-methacryloyloxyethyl phosphorylcholine. Biomicrofluidics. Mar. 2012;6(1):12822-1282212. doi: 10.1063/1.3682098. Epub Mar. 15, 2012.
Joanicot et al., "Droplet Control For Microfluidics", Science 309:887-888 (Aug. 2005).
Johnson, "Rapid microfluidic mixing", Analytical Chemistry, vol. 74, No. 1, pp. 45-51, (Jan. 1, 2002).
Jung, et al. Micro machining of injection mold inserts for fluidic channel of polymeric biochips. Sensors. 2007; 7(8):1643-1654.
Katsura, et al. Indirect micromanipulation of single molecules in water-in-oil emulsion. Electrophoresis. Jan. 2001;22(2):289-93.
Kawari et al., Mass-Production System of Nearly Monodisperse Diameter Gel Particles Using Droplets Formation in a Microchannel, Micro Total Analysis Systems, vol. I, 368-370, Springer (2002).
Kenis, et al. Microfabrication Inside Capillaries Using Multiphase Laminar Flow Patterning. Science. 1999; 285:83-85.
Khomiakova et al., Analysis of perfect and mismatched DNA duplexes by a generic hexanucleotide microchip. Mol Biol(Mosk). Jul.-Aug. 2003;37(4):726-41. Russian. Abstract only.
Kim et al., Albumin loaded microsphere of amphiphilic poly(ethylene glycol)/poly(a-ester) multiblock copolymer. Eu. J. Pharm. Sci. 2004;23:245-51. Available online Sep. 27, 2004.
Kim, et al. Fabrication of monodisperse gel shells and functional microgels in microfluidic devices. Angew Chem Int Ed Engl. 2007;46(11):1819-22.
Kim, et al. Rapid prototyping of microfluidic systems using a PDMS/polymer tape composite. Lab Chip. May 7, 2009;9(9):1290-3. doi: 10.1039/b818389a. Epub Feb. 10, 2009.
"Kiss MM, et al. "High-Throughput Quantitative Polymerase Chain Reaction in Picoliter Droplets"; Anal Chem 80(23); (2008); pp. 8975-8981."
Klein, et al. Droplet barcoding for single-cell transcriptomics applied to embryonic stem cells. Cell. May 21, 2015;161(5):1187-201. doi: 10.1016/j.cell.2015.04.044.
Kobayashi, et al. Effect of slot aspect ratio on droplet formation from silicon straight-through microchannels. J Colloid Interface Sci. Nov. 1, 2004;279(1):277-80.
Kobayashi et al., "Straight-Through Microchannel Devices For Generating Monodisperse Emulsion Droplets Several Microns in Size", Microfluid Nanofluid 4:167-177, (Mar. 30, 2008).
Kohler et al., "Nanoliter Segment Formation in Micro Fluid Devices for Chemical and Biological Micro Serial Flow Processes in Dependence on Flow Rate and Viscosity", Sensors and Actuators A 119, 19-27 (Nov. 2, 2005).
Kolodeziejczyk et al., "The technology and biology of single-cell RNA sequencing", Molecular Cell, vol. 58 (May 21, 2015).
Koster et al., "Drop-based microfluidic devices for encapsulation of single cells", Lab on a Chip The Royal Soc. of Chern. 8: 1110-1115 (2008).
Kutyavin, et al. Oligonucleotides containing 2-aminoadenine and 2-thiothymine act as selectively binding complementary agents. Biochemistry. Aug. 27, 1996;35(34):11170-6.
Lagally, et al. Single-Molecular DNA Amplification and Analysis in an Integrated Microfluidic Device. Anal Chem. Feb. 1, 2001;73(3):565-70.
Lagus, et al. A review of the theory, methods and recent applications of high-throughput single-cell droplet microfluidics. J. Phys. D: Appl. Phys. (2013) 46:114005. (21 pages).
Lander, et al. Initial sequencing and analysis of the human genome. Nature, 409 (Feb. 15, 2001): 860-921.
Laulicht et al., Evaluation of continuous flow nanosphere formation by controlled microfluidic transport, American Chem. Society (Aug. 6, 2008).
Lee et al., "A tunable microflow focusing device utilizing controllable moving walls and its applications for formation of microdroplets in liquids", J. Micromech. Microeng. 17 1121-1129 (Jun. 2007).
Lee et al., Double emulsion-templated nanoparticle colloidosomes with selective permeability. Adv Mater. 2008;20:3498-503. Month not cited on publication.
Lee, et al., "Microfluidic air-liquid cavity acoustic transducers for on-chip integration of sample preparation and sample detection" (Dec. 2010).
Li, et al. Step-emulsification in a microfluidic device. Lab Chip. Feb. 21, 2015;15(4):1023-31. doi: 10.1039/c4lc01289e.
Li, Y., et al., "PEGylated PLGA Nanoparticles as protein carriers: synthesis, preparation and biodistribution in rats," Journal of Controlled Release, vol. 71, pp. 203-211 (2001).
Liu et. al., "Droplet formation in a T-shaped microfluidic junction", Journal of Applied Physics vol. 106, 034906 (Aug. 7, 2009).
Liu et al., "Droplet-based synthetic method using microflow focusing and droplet fusion", Microfluid Nanofluid, vol. 3, 239-24 (2007).
Liu et al., Dynamics of coalescence of plugs with a hydrophilic wetting layer induced by flow in a microfluidic chemistrode (Dec. 9, 2008).
Liu, et al. Preparation of uniform-sized PLA microcapsules by combining Shirasu porous glass membrane emulsification technique and multiple emulsion-solvent evaporation method. J Control Release. Mar. 2, 2005;103(1):31-43. Epub Dec. 21, 2004.
Liu, et al. Smart thermo-triggered squirting capsules for Nanoparticle delivery. Soft Matter. 2010; 6(16):3759-3763.
Lorenceau, E., et al., "Generation of Polymerosomes from Double-Emulsions," Langmuir, vol. 21, pp. 9183-9186 (2005).
Loscertales, I.G., et al., "Micro/Nano Encapsulation via Electrified Coaxial Liquid Jets," Science, vol. 295, pp. 1695-1698 (2002).
Love, "A microengraving method for rapid selection of single cells producing antigen-specific antibodies", Nature Biotech, 24:6 703 (Jun. 2006).
Lowe, Adam J. Norbornenes and [n]polynorbornanes as molecular scaffolds for anion recognition. Ph.D. Thesis (May 2010). (361 pages).
Maan, et al. Spontaneous droplet formation techniques for monodisperse emulsions preparation—Perspectives for food applications. Journal of Food Engineering. vol. 107, Issues 3-4, Dec. 2011, pp. 334-346.

(56) References Cited

OTHER PUBLICATIONS

Macosko, et al. Highly Parallel Genome-wide Expression Profiling of Individual Cells Using Nanoliter Droplets. Cell. May 21, 2015;161(5):1202-14. doi: 10.1016/j.cell.2015.05.002.
Mair, et al. Injection molded microfluidic chips featuring integrated interconnects. Lab Chip. Oct. 2006;6(10):1346-54. Epub Jul. 31, 2006.
Makino, et al. Preparation of hydrogel microcapsules: Effects of preparation conditions upon membrane properties. Colloids and Surfaces B: Biointerfaces. Nov. 1998; 12(2), 97-104.
Malic et al., "Integration and detection of biochemical assays in digital microfluidic LOC devices", Lab Chip, vol. 10, 418-431 (2010).
Malsch et al., "µPIV-Analysis of Taylor flow in micro channels", Chemical Engineering Journal, 135S, S166-S172 (2008).
Man. Monolithic Structures for Integrated Microfluidic Analysis. PhD Thesis. 2001.
Marcus. Gene method offers diagnostic hope. The Wall Street Journal. Jul. 11, 2012.
"Mary P. Pascaline, et al; "Controlling droplet incubation using close-packed plug flow"; Biomicrofluidics 5; (2011); pp. 024101-1-024101-6."
Mason, T.J. and Bibette, J. Shear Rupturing of Droplets in Complex Fluids, Langmuir, 13(17):4600-4613 (1997).
Matochko, et al. Uniform amplification of phage display libraries in monodisperse emulsions. Methods. Sep. 2012;58(1):18-27. doi: 10.1016/j.ymeth.2012.07.012. Epub Jul. 20, 2012.
Mazutis et al., Droplet-Based Microfluidic Systems for High-Throughput Single DNA Molecule Isothermal Amplification and Analysis, Anal Chem 81(12):4813-4821 (2009).
Mazutis, et al., Preparation of monodisperse emulsions by hydrodynamic size fractionation (Nov. 18, 2009).
Mazutis, et al. Selective droplet coalescence using microfluidic systems. Lab Chip. Apr. 24, 2012;12(10):1800-6. doi: 10.1039/c2lc40121e. Epub Mar. 27, 2012.
Meier et al., "Plug-Based Microfluidics with Defined Surface Chemistry to Miniaturize and control aggregation of amyloidogenic peptides", Angew Chem. Ed Engl., 48(8), 1487-1489 (2009).
Merriman, et al. Progress in ion torrent semiconductor chip based sequencing. Electrophoresis. Dec. 2012;33(23):3397-417. doi: 10.1002/elps.201200424.
Microfluidic ChipShop, Microfluidic Product Catalogue (Feb. 2005).
Microfluidic ChipShop. Microfluidic product catalogue. Mar. 2005.
Microfluidic ChipShop. Microfluidic product catalogue. Oct. 2009.
Mirzabekov, "DNA Sequencing by Hybridization—a Megasequencing Method and a Diagnostic Tool?" Trends in Biotechnology 12(1): 27-32 (1994).
Moore, et al. Behavior of capillary valves in centrifugal microfluidic devices prepared by three- dimensional printing. Microfluidics and Nanofluidics. 2011; 10(4):877-888.
Mouritzen et al., Single nucleotide polymorphism genotyping using locked nucleic acid (LNa). Expert Rev Mol Diagn. Jan. 2003;3(1):27-38.
Nagashima, et al. Preparation of monodisperse poly (acrylamide-co-acrylic acid) hydrogel microspheres by a membrane emulsification technique and their size-dependent surface properties. Colloids and Surfaces B: Biointerfaces. Jun. 15, 1998; 11(1-2), 47-56.
Navin. The first five years of single-cell cancer genomics and beyond. Genome Res. Oct. 2015;25(10):1499-507. doi: 10.1101/gr.191098.115.
Nguyen, et al. In situ hybridization to chromosomes stabilized in gel microdrops. Cytometry. 1995; 21:111-119.
Nisisako, et al. Droplet formation in a microchannel network. Lab Chip. Feb. 2002;2(1):24-6. Epub Jan. 18, 2002.
Nisisako et al., "Novel microreactors for functional polymer beads", Chemical Engineering Journal 101 23-29 (Nov. 19, 2004).
Nisisako et al., "Synthesis of Monodisperse Bicolored Janus Particles with Electrical Aniaotropy Using a Microfluidic Co-Flow System", Adv. Mater., 18, 1152-1156.
Nisisako, T. et al. "Droplet Formation in a Microchannel on PMMA Plate" Abstract. 2001 Kluwer Academic Publishers. p. 137-138.
Nisisako, T. et al., Microfluidics large-scale integration on a chip for mass production of monodisperse droplets and particles, The Royal Society of Chemistry: Lab Chip, (Nov. 23, 2007) 8:287-293.
Niu et al., A hybrid microfluidic chip for digital electro-coalescence of droplets, (Nov. 2009).
Niu et al. "Droplet-based compartmentalization of chemically separated components in two-dimensional separations", Chem. Commun, 6159-6161 (Sep. 15, 2009).
Novak, et al. Single cell multiplex gene detection and sequencing using microfluidicallygenerated agarose emulsions. Angew Chem Int Ed Engl. Jan. 10, 2011;50(2):390-5. doi: 10.1002/anie.201006089.
Oberholzer, et al. Polymerase chain reaction in liposomes. Chem Biol. Oct. 1995;2(10):677-82.
Ogawa, et al. Production and characterization of O/W emulsions containing cationic droplets stabilized by lecithin-chitosan membranes. J Agric Food Chem. Apr. 23, 2003;51(9):2806-12.
Okushima, S., et al., "Controlled Production ofMonodisperse Double Emulsions by Two-Step Droplet Breakup in Microfluidic Devices," Langmuir, vol. 20, pp. 9905-9908 (2004).
Ong et al., Experimental and computational analysis of droplet formation in a high-performance flow-focusing geometry, Sensors and Actuators A 138, 203-212 (May 4, 2007).
Perez, C., et al., "Poly(lactic acid)-poly(ethylene glycol) Nanoparticles as new carriers for the delivery of plasmid DNA," Journal of Controlled Release, vol. 75, pp. 211-224 (2001).
Perroud et al., "Isotropically etched radial micropore for cell concentration, immobilization, and picodroplet generation", Lab Chip, 9, 507-515 (Jan. 7, 2009).
Peters, B.A. et al. Accurate whole-genome sequencing and haplotyping from 10 to 20 human cells. Nature, 487(7406):190-195 (Jul. 11, 2012).
Plunkett, et al. Chymotrypsin responsive hydrogel: application of a disulfide exchange protocol for the preparation of methacrylamide containing peptides. Biomacromolecules. Mar.-Apr. 2005;6(2):632-7.
Ramsey, J.M. "The burgeoning power of the shrinking laboratory" Nature Biotech (1999) 17:1061-1062.
Rotem, et al. High-Throughput Single-Cell Labeling (Hi-SCL) for RNA-Seq Using Drop-Based Microfluidics. PLoS One. May 22, 2015;10(5):e0116328. doi: 10.1371/journal.pone.0116328. eCollection 2015.
Rotem, et al. Single Cell Chip-Seq Using Drop-Based Microfluidics. Abstract #50. Frontiers of Single Cell Analysis, Stanford University Sep. 5-7, 2013.
Ryan, "Rapid assay for mycobacterial growth and antibiotic susceptibility using gel microdrop and encapsulation", J. Clinical Microbial., 33:7 1720-1726 (1995).
Sahin, et al. Microfluidic EDGE emulsification: the importance of interface interactions on droplet formation and pressure stability. Sci Rep. May 27, 2016;6:26407. doi: 10.1038/srep26407.
Schirinzi et al., Combinatorial sequencing-by-hybridization: Analysis of the NF1 gene. Genet Test. 2006 Spring;10(1):8-17.
Schmitt, "Bead-based multiplex genotyping of human papillomaviruses", J. Clinical Microbial., 44:2 504-512 (2006).
Schubert, et al. Microemulsifying fluorinated oils with mixtures of fluorinated and hydrogenated surfactants. Colloids and Surfaces A; Physicochemical and Engineering Aspects, 84(1994) 97-106.
Seiffert, et al. Smart microgel capsules from macromolecular precursors. J Am Chem Soc. May 12, 2010;132(18):6606-9. doi: 10.1021/ja102156h.
Sessoms et al., "Droplet motion in microfluidic networks: Hydrodynamic interactions and pressure-drop measurements", Physical Review, E 80, 016317 (Jul. 31, 2009).
Shah, "Fabrication of mono disperse thermosensitive microgels and gel capsules in micro fluidic devices", Soft Matter, 4:2303-2309 (2008).
Shaikh, et al. A modular microfluidic architecture for integrated biochemical analysis. Proc Natl Acad Sci U S A. Jul. 12, 2005;102(28):9745-50. Epub Jun. 28, 2005.

(56) References Cited

OTHER PUBLICATIONS

Shimkus, et al. A chemically cleavable biotinylated nucleotide: usefulness in the recovery of protein-DNA complexes from avidin affinity cols. Proc Natl Acad Sci U S A. May 1985;82(9):2593-7.
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.
Song, et al. Reactions in droplets in microfluidic channels. Angew Chem Int Ed Engl. Nov. 13, 2006;45(44):7336-56.
Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.
Holmberg, et al. The biotin-streptavidin interaction can be reversibly broken using water at elevated temperatures. Feb. 2, 2005. Electrophoresis, 26:501-510.
Invitrogen Dynal. Dynabeads M-280 Streptavidin 2006 product sheet.
Morton. Parameters of the human genome. Apr. 23, 1991. Proceedings of the National Academy of Sciences of the United States of America, 88: 7474-7476.
National Human Genome Research Institute (NHGRI). The Human Genome Project Completion: Frequently Asked Questions. Last Updated: Oct. 30, 2010.
Qiagen. Omniscript Reverse Transcription Handbook. Oct. 2010.
Seiffert, et al. Microfluidic fabrication of smart microgels from macromolecular precursors. 2010. Polymer.
Srisa-Art et al., "High-throughput DNA droplet assays using Picoliter reactor volumes", Anal. Chem. vol. 79, 6682-6689 (Sep. 9, 2007).
Su, et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).
Sun et al., Progress in research and application of liquid-phase chip technology. Chinese Journal Experimental Surgery. May 2005;22(5):639-40.
Tawfik, D.S., et al., "Man-made cell-like compartments for molecular evolution," Nature Biotechnology, vol. 16, pp. 652-656 (1998).
Tetradis-Meris et al., Novel parallel integration of microfluidic device network for emulsion formation. Ind. Eng. Chern. Res., 2009; 48 (19): 8881-8889.
Tewhey, et al. Microdroplet-based PCR amplification for large-scale targeted sequencing. Nat Biotechnol. Nov. 2009;27(11):1025-31. doi: 10.1038/nbt.1583. Epub Nov. 1, 2009.
Tewhey, et al. Microdroplet-based PCR enrichment for large-scale targeted sequencing. Nat Biotechnol. Nov. 2009;27(11):1025-31. doi: 10.1038/nbt.1583. Epub Nov. 1, 2009.
Theberge, et al. Microdroplets in microfluidics: an evolving platform for discoveries in chemistry and biology. Angew Chem Int Ed Engl. Aug. 9, 2010;49(34):5846-68. doi: 10.1002/anie.200906653.
Thorsen, et al. Dynamic pattern formation in a vesicle-generating microfluidic device. Physical Review Letters. American Physical Society. 2001; 86(18):4163-4166.
Tonelli, et al. Perfluoropolyether functional oligomers: unusual reactivity in organic chemistry. Journal of fluorine chemistry. 2002; 118(1)107-121.
Tubeleviciute, et al. Compartmentalized self-replication (CSR) selection of Thermococcus litoralis Sh1B DNa polymerase for diminished uracil binding. Protein Eng Des Sel. Aug. 2010;23(8):589-97. doi: 10.1093/protein/gzq032. Epub May 31, 2010.
Turner, et al. Methods for genomic partitioning. Annu Rev Genomics Hum Genet. 2009;10:263-84. doi: 10.1146/annurev-genom-082908-150112. Review.
Umbanhowar, P.B., et al., "Monodisperse Emulsion Generation via Drop Break Off in a Coflowing Stream," Langmuir, vol. 16, pp. 347-351 (2000).

Van Dijke, et al. Effect of viscosities of dispersed and continuous phases in microchannel oil-in-water emulsification . Microfluid Nanofluid (2010) 9: 77. https://doi.org/10.1007/s10404-009-0521-7

Wagner, et al. Biocompatible fluorinated polyglycerols for droplet microfluidics as an alternative to PEG-based copolymer surfactants. Lab Chip. Jan. 7, 2016;16(1):65-9. doi: 10.1039/c5lc00823a. Epub Dec. 2, 2015.
Wang, et al. A novel thermo-induced self-bursting microcapsule with magnetic-targeting property. Chemphyschem. Oct. 5, 2009;10(14):2405-9.
Wang et al., Single nucleotide polymorphism discrimination assisted by improved base stacking hybridization using oligonucleotide microarrays. Biotechniques. 2003;35:300-08.
Ward, et al. Microfluidic flow focusing: Drop size and scaling in pressure versus flow-rate-driven pumping. Electrophoresis. Oct. 2005;26(19):3716-24.
Weaver, "Rapid clonal growth measurements at the single-cell level: gel microdroplets and flow cytometry", Biotechnology, 9:873-877 (1991).
Weigl, et al. Microfluidic Diffusion-Based Separation and Detection. Science. 1999; pp. 346-347.
Whitesides, "Soft lithography in biology and biochemistry", Annual Review of Biomedical Engineering, 3:335-373 (2001).
Williams, et al. Amplification of complex gene libraries by emulsion PCR. Nature Methods. 2006;3(7):545-50.
Woo, et al. G/C-modified oligodeoxynucleotides with selective complementarity: synthesis and hybridization properties. Nucleic Acids Res. Jul. 1, 1996;24(13):2470-5.
Xia and Whitesides, Soft Lithography, Ann. Rev. Mat. Sci. 28:153-184 (1998).
Yamamoto, et al. Chemical modification of Ce(IV)/EDTA-base artificial restriction DNA cutter for versatile manipulation of double-stranded DNA. Nucleic Acids Research. 2007; 35(7):e53.
Zeng, et al. High-performance single cell genetic analysis using microfluidic emulsion generator arrays. Anal Chem. Apr. 15, 2010;82(8):3183-90. doi: 10.1021/ac902683t.
Zhang, "Combinatorial marking of cells and organelles with reconstituted fluorescent proteins", Cell, 119:137-144 (Oct. 1, 2004).
Zhang, et al. Degradable disulfide core-cross-linked micelles as a drug delivery system prepared from vinyl functionalized nucleosides via the RAFT process. Biomacromolecules. Nov. 2008;9(11):3321-31. doi: 10.1021/bm800867n. Epub Oct. 9, 2008.
Zhang, et al. One-step fabrication of supramolecular microcapsules from microfluidic droplets. Science. Feb. 10, 2012;335(6069):690-4. doi: 10.1126/science.1215416.
Zhao, J., et al., "Preparation of hemoglobin-loaded Nano-sized particles with porous structure as oxygen carriers," Biomaterials, vol. 28, pp. 1414-1422 (2007).
Zhu, et al. Synthesis and self-assembly of highly incompatible polybutadienepoly(hexafluoropropoylene oxide) diblock copolymers. Journal of Polymer Science Part B: Polymer Physics. 2005; 43(24):3685-3694.
Zimmermann et at., Microscale production of hybridomas by hypo-osmolar electrofusion. Hum. Antibodies Hybridomas. Jan. 1992;3(1 ): 14-8.
Zong et al. Genome-Wide Detection of Single Nucleotide and Copy Number Variations of a Single Human Cell. Science 338(6114):1622-1626 (2012) .
10X Genomics. 10x Genomics Chromium™ Single Cell 3' Solution Utilized for Perturb-seq Approach. Press Release. Dec. 19, 2016. Retrieved from https://www.10xgenomics.com/news/10x-genomics-chromium-single-cell-3-solution-utilized-perturb-seq-approach/.
Adamson, et al. A Multiplexed Single-Cell CRISPR Screening Platform Enables Systematic Dissection of the Unfolded Protein Response. Cell. Dec. 15, 2016;167(7):1867-1882.e21. doi: 10.1016/j.cell.2016.11.048.
Adey, et al. Rapid, low-input, low-bias construction of shotgun fragment libraries by high-density in vitro transposition. Genome Biology 11:R119 (2010).
Adey, et al., "Ultra-low-input, tagmentation-based whole-genome bisulfite sequencing", Genome Research, 2012, 22 ;6): 1139-1143.

(56) References Cited

OTHER PUBLICATIONS

Ahern, "Biochemical, Reagents Kits Offer Scientists Good Return on Investment" The Scientist (1995) 9(15):1-7.
Aitman, et al. Copy number polymorphism in Fcgr3 predisposes to glomerulonephritis in rats and humans. Nature. Feb. 16, 2006;439(7078):851-5.
Altemos et al., "Genomic Characterization of Large Heterochromatic Gaps in the Human Genome Assembly," PLOS Computational Biology, May 15, 2014, vol. 10, Issue 5, 14 pages.
Amini, S. et al. "Haplotype-resolved whole-genome sequencing by contiguity-preserving transposition and combinatorial indexing" Nature Genetics (2014) 46:1343-1349 doi:10.1038/ng.3119.
Anonymous, "Oligo(dT)25 cellulose beads" NEB (2012) Retrieved from the Internet:https://www.neb.com/~/media/Catalog/All-Products/286CA51268E24DE1B06F1CB288698B54/Datacards%20or%Manuals/S1408Datasheet-Lot0011205.pdf.
Anonymous, "Oligotex Handbook" Qiagen (2012) XP055314680, Retrieved from the Internet: URL:http://www.qiagen.com/de/resources/download.apsx?id=f9fald98-d54d-47e7-a20b-8b0cb8975009&lang=en.
Anonymous: "TCEP=HCl" Thermo Scientific, Dec. 31, 2013 (Dec. 31, 2013), XP055508461, Retrieved from the Internet: URL:https://assets.thermofisher.com/TFS-Assets/LSG/manuals/MAN0011306_TCEP_HCl_UG.pdf.
Anonymous: "Viscosity-Basic concepts" (2004) XP055314117, Retrieved from the Internet: URL:http://lhtc.epfl.ch/webdav/site/lhtc/shared/import/migration/2 VISCOSITY.pdf.
Ason et al. DNA sequence bias during Tn5 transposition. Journal of molecular biology 335.5 (2004): 1213-1225.
Balikova, et al. Autosomal-dominant microtia linked to five tandem copies of a copy-number variable region at chromosome 4p16. Am J Hum Genet. Jan. 2008;82(1):181-7. doi: 10.1016/j.ajhg.2007.08.001.
BD. BD Rhapsody™ Single-Cell Analysis System: Analyze hundreds of genes across tens of thousands of single cells in parallel. BD, Becton, Dickinson and Company. BDGM1012 Rev. 1. 2017. 8 pages.
Bentzen, et al. Large-scale detection of antigen-specific T cells using peptide-MHC-I multimers labeled with DNA barcodes. Nat Biotechnol. Oct. 2016;34(10): 1037-1045. doi: 10.1038/nbt.3662. Epub Aug. 29, 2016.
Berkum, et al. Hi-C: a method to study the three-dimensional architecture of genomes. J Vis Exp. May 6, 2010;(39). pii: 1869. doi: 10.3791/1869.
Biles et al., Low-fidelity Pyrococcus furiosis DNA polymerase mutants useful in error-prone PCR. Nucl. Acids Res. 32(22):e176 2004.
Bjornsson et al., Intra-individual change over time in DNA methylation with familial clustering, JAMA, Jun. 25, 2008, vol. 299 No. 24, pp. 2877-2883.
Bodi, K. et al. "Comparison of Commercially Available Target Enrichment Methods for Next-Generation Sequencing" J Biomolecular Techniques (2013) 24:73-86.
Boulanger, et al, "Massively parallel haplotyping on microscopic beads for the high-throughput phase analysis of single molecules", PLoS One, vol. 7:1-10, 2012.
Boyle, et al. "High-resolution genome-wide in vivo footprinting of diverse transcription factors in human cells", Genome Res. Mar. 2011;21(3):456-64.
Brenner, et al. In vitro cloning of complex mixtures of DNA on microbeads: physical separation of differentially expressed cDNAs. Proc Natl Acad Sci U S A. Feb. 15, 2000;97(4):1665-70.
Briggs, et al. "Tumor-infiltrating immune repertoires captures by single-cell barcoding in emulsion" with Supplementary material. bioRxiv 134841; doi: https://doi.org/10.1101/134841. Posted May 5, 2017.
Brown, K., Targeted Sequencing Using Droplet-Based Microfluidics, RainDance Technologies, 2009, 1-18.

Browning, et al. Haplotype phasing: existing methods and new developments. Nat Rev Genet. Sep. 16, 2011;12(10):703-14. doi: 10.1038/nrg3054. Review.
Buchman GW, et al. Selective RNA amplification: a novel method using dUMP-containing primers and uracil DNA glycosylase. PCR Methods Appl. Aug. 1993; 3(1):28-31.
Buenrostro, et al. ATAC-seq: A Method for Assaying Chromatin Accessibility Genome-Wide. Curr Protoc Mol Biol.; 109: 21.29.1-21.29.9. doi: 10.1002/0471142727.mb2129s109.
Buenrostro, et al. Single-cell chromatin accessibility reveals principles of regulatory variation. Nature. Jul. 23, 2015;523(7561):486-90. doi: 10.1038/nature14590. Epub Jun. 17, 2015.
Buenrostro, et al. "Transposition of native chromatin for fast and sensitive epigenomic profiling of open chromatin, DNA-binding proteins and nucleosome position." Nat Methods. Dec. 2013;10(12):1213-8. doi: 10.1038/nmeth.2688. Epub Oct. 6, 2013.
Cappuzzo, et al. Increased HER2 gene copy number is associated with response to gefitinib therapy in epidermal growth factor receptor-positive non-small-cell lung cancer patients. J Clin Oncol. Aug. 1, 2005;23(22):5007-18.
Caruccio, et al. Nextera Technology for NGS DNA Library Preparation: Simultaneous Fragmentation and Tagging by In Vitro Transposition, Nextera Technology, 2009, 16-3, 1-3. (Year: 2009).
Caruccio N., Preparation of Next-Generation Sequencing Libraries Using Nextera Technology: Simultaneous DNA Fragmentation and Adaptor Tagging by In Vitro Transposition. Ch. 17 Methods in Microbiology 733:241 (2011).
Casbon, et al., "Reflex: intramolecular barcoding of long-range PCR products for sequencing multiple pooled DNAs", Nucleic Acids Res., pp. 1-6, 2013.
Choi, et al. Identification of novel isoforms of the EML4-ALK transforming gene in non-small cell lung cancer. Cancer Res. Jul. 1, 2008;68(13):4971-6. doi: 10.1158/0008-5472.CAN-07-6158.
Christian, et al. Targeting DNA double-strand breaks with TAL effector nucleases. Genetics.186 (2010): 757-761.
Christiansen et al. "The Covalent Eukaryotic Topoisomerase I-DNA Intermediate Catalyzes pH-dependent Hydrolysis and Alcoholysis" J Biol Chem (Apr. 14, 1994) 269(15):11367-11373.
Chung, et al. Structural and molecular interrogation of intact biological systems. Nature. May 16, 2013;497(7449):332-7. doi: 10.1038/nature12107. Epub Apr. 10, 2013.
Clark, et al. Single-cell epigenomics: powerful new methods for understanding gene regulation and cell identity. Genome Biol. Apr. 18, 2016;17:72. doi: 10.1186/s13059-016-0944-x.
Cong, et al. Multiplex genome engineering using CRISPR/Cas systems. Science. 339.6121 (Feb. 15, 2013): 819-23. doi: 10.1126/science.1231143. Epub Jan. 3, 2013.
Cook, et al. Copy-number variations associated with neuropsychiatric conditions. Nature. Oct. 16, 2008;455(7215):919-23. doi: 10.1038/nature07458.
Co-pending U.S. Appl. No. 15/440,772, filed Feb. 23, 2017.
Co-pending U.S. Appl. No. 15/449,741, filed Mar. 3, 2017.
Co-pending U.S. Appl. No. 16/033,065, filed Jul. 11, 2018.
Co-pending U.S. Appl. No. 16/044,374, filed Jul. 24, 2018.
Co-pending U.S. Appl. No. 16/107,685, filed Aug. 21, 2018.
Co-pending U.S. Appl. No. 16/170,980, filed Oct. 25, 2018.
Co-pending U.S. Appl. No. 16/274,134, filed Feb. 12, 2019.
Coufal, et al. L1 retrotransposition in human neural progenitor cells. Nature. Aug. 2, 20097;460(7259):1127-31. doi: 10.1038/nature08248. Epub Aug. 5, 2009.
Cusanovich; et al., "Multiplex single-cell profiling of chromatin accessibility by combinatorial cellular indexing. Sciencexpress, May 7, 2014, p. 1-9."
Cusanovich, et al. Supplementary materials for Multiplex single-cell profiling of chromatin accessibility by combinatorial cellular indexing. Science. May 22, 2015;348(6237):910-4. doi: 10.1126/science.aab1601. Epub May 7, 2015.
Dekker, et al. Capturing chromosome conformation. Science. Feb. 15, 2002;295(5558):1306-11.
Depristo et al. A framework for variation discovery and genotyping using next-generation DNA sequencing data. Nature Genet 43:491-498 (2011).

(56) References Cited

OTHER PUBLICATIONS

Dey, et al. Integrated genome and transcriptome sequencing of the same cell. Dey, Siddharth S. et al. "Integrated Genome and Transcriptome Sequencing from the Same Cell." Nature biotechnology 33.3 (2015): 285-289. PMC. Web. Dec. 18, 2017.
Dixit, et al. Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.
Doshi, et al. Red blood cell-mimicking synthetic biomaterial particles. Proceedings of the National Academy of Sciences 106.51 (2009): 21495-21499.
Dressman et al. Supplementary Information pp. 1-2 of article published 2003, PNAS 100(15:8817-22).
Dressman et al. Transforming single DNA molecules into fluorescent magnetic particles for detection and enumeration of genetic variations. Proc. Natl. Acad. Sci. 2003. 100(15):8817-8822.
Epicentre., "EZ-Tn5TM Custom Transposome Construction Kits", http://www.epicentre.com, pp. 1-17, 2012.
Fabi, et al. Correlation of efficacy between EGFR gene copy number and lapatinib/capecitabine therapy in HER2-positive metastatic breast cancer. J. Clin. Oncol. 2010; 28:15S. 2010 ASCO Meeting abstract Jun. 14, 2010:1059.
Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.
Fan, et al. Whole-genome molecular haplotyping of single cells. Nature Biotechnology, vol. 29, No. 1. Jan. 1, 2011. pp. 51-57.
Fang, et al. Fluoride-cleavable biotinylation phosphoramidite for 5'-end-labeling and affinity purification of synthetic oligonucleotides. Nucleic Acids Res. Jan. 15, 2003;31(2):708-15.
Frampton, G.M. et al. "Development and validation of a clinical cancer genomic profiling test based on massively parallel DNA sequencing" Nature Biotechnology (2013) 31(11):1023-1031. doi:10.1038/nbr.2696.
Gangadharan et al., DNA transposon Hermes insert into DNA in nucleosome-free regions in vivo, Proc nat Ad Sci, Dec. 21, 2010, vol. 107, No. 51, pp. 1966-1972.
Gao et al., Toehold of dsDNA Exchange Affects the Hydrogel Swelling Kinetic of a Polymer-dsDNA Hybrid Hydrogel, Royal Soc. Chem. 7:1741-1746 (Dec. 20, 2010).
Gericke, et al. Functional cellulose beads: preparation, characterization, and applications. Chemical reviews 113.7 (2013): 4812-4836.
Gonzalez, et al. The influence of CCL3L1 gene-containing segmental duplications on HIV-1/AIDS susceptibility. Science. Mar. 4, 2005;307(5714):1434-40. Epub Jan. 6, 2005.
Green et al. Insertion site preference of Mu, Tn5, and Tn7 transposons. Mobile DNA 3.1 (2012): 3.
Greenleaf, et al. Assaying the epigenome in limited numbers of cells. Methods. Jan. 15, 2015;72:51-6. doi: 10.1016/j.ymeth.2014.10.010. Epub Oct. 22, 2014.
Hamilton, A.J. "microRNA in erythrocytes" Biochem. Soc. Trans. (2010) 38, 229-231.
Han, SW et al. "Targeted Sequencing of Cancer-Related Genes in Colorectal Cancer Using Next-Generation Sequencing" PLOS One (2013) 8(5):e64271.
Han, X. et al. "CRISPR-Cas9 delivery to hard-to-transfect cells via membrane deformation" Science Advances (2015) 1(7): E1500454 (8 pages).
Haring, et al. Chromatin immunoprecipitation: optimization, quantitative analysis and data normalization. Plant Methods. 2007; 3: 11.
He, J. et al. "Genotyping-by-sequencing (GBS), an ultimate marker-assisted selections (MAS) tool to accelerate plant breeding" Frontiers in Plant Sci (Sep. 30, 2014) 5:1-8.
Hiatt, et al. Parallel, tag-directed assembly of locally derived short sequence reads. Nat Methods. Feb. 2010;7(2):119-22. Epub Jan. 17, 2010.
Hirsch et al. (2002) "Easily reversible desthiobiotin binding to streptavidin, avidin, and other biotin-binding proteins: uses for protein labeling, detection, and isolation." Analytical of Biochemistry 308(2):343-357.
Hjerten, et al. General methods to render macroporous stationary phases nonporous and deformable, exemplified with agarose and silica beads and their use in high-performance ion-exchange and hydrophobic-interaction chromatography of proteins. Chromatographia 31.1-2 (1991): 85-94.
Hosono S, et al. Unbiased whole-genome amplification directly from clinical samples. Genome Res. May 2003; 13(5):954-64. Epub Apr. 14, 2003.
"How many species of bacteria are there" (wisegeek.com; accessed Jan. 21, 2014).
Hu et al., Shape Controllable Microgel Particles Prepared by Microfluidic Combining External Crosslinking, Biomicrofluidics 6:26502 (May 18, 2012).
Illumina Nextera Enrichment Sample Preparation Guide. Feb. 2013.
Illumina TruSeq Custom Enrichment Kit Data Sheet. (c) 2014.
Imburgio, et al, "Studies of promoter recognition and start site selection by T7 RNA polymerase using a comprehensive collection of promoter variants", Biochemistry., 39:10419-30, 2000.
Ioannidis, N. Manufacturing of agarose-based chromatographic adsorbents with controlled pore and particle sizes. A thesis submitted to The University of Birmingham for the degree of Doctor of Philosophy. 2009.
Joneja, et al. Linear nicking endonuclease-mediated strand-displacement DNA amplification. Anal Biochem. Jul. 1, 2011;414(1):58-69. doi: 10.1016/j.ab.2011.02.025. Epub Feb. 20, 2011.
JPK "Determining the elastic modulus of biological samples using atomic force microscopy" (https://www.jpk.com/ app-technotes-img/AFM/pdf/jpk-app-elastic-modulus.14-1.pdf) 2009, pp. 1-9 (Year: 2009).
Kamperman, et al. Centering Single Cells in Microgels via Delayed Crosslinking Supports Long-Term 3D Culture by Preventing Cell Escape. Small. Jun. 2017;13(22). doi: 10.1002/smll.201603711. Epub Apr. 28, 2017.
Kaper, et al. Supporting Information for "Whole-genome haplotyping by dilution, amplification, and sequencing." Proc Natl Acad Sci U S A. Apr. 2, 2013;110(14):5552-7. doi: 10.1073/pnas.1218696110. Epub Mar. 18, 2013.
Kaper, et al. Whole-genome haplotyping by dilution, amplification, and sequencing. Proc Natl Acad Sci U S A. Apr. 2, 2013;110(14):5552-7. doi: 10.1073/pnas.1218696110. Epub Mar. 18, 2013.
Karmakar, et al. Organocatalytic removal of formaldehyde adducts from RNA and DNA bases. Nat Chem. Sep. 2015;7(9):752-8. doi: 10.1038/nchem.2307. Epub Aug. 3, 2015.
Kebschull, et al. High-Throughput Mapping of Single-Neuron Projections by Sequencing of Barcoded RNA. Neuron. Sep. 7, 2016;91(5):975-87. doi: 10.1016/j.neuron.2016.07.036. Epub Aug. 18, 2016.
Kirkness et al. "Sequencing of isolated sperm cells for direct haplotyping of a human genome," Genome Res (2013) 23:826-832.
Kitzman et al. "Haplotype-resolved genome sequencing of a Gujarati Indian individual." Nat Biotechnol (2011) 29:59-63.
Kitzman, et al. Noninvasive whole-genome sequencing of a human fetus. Sci Transl Med. Jun. 6, 2012;4(137):137ra76. doi: 10.1126/scitranslmed.3004323.
Kivioja, et al. Counting absolute numbers of molecules using unique molecular identifiers. Nat Methods. Nov. 20, 2011;9(1):72-4.
Knapp, et al. Generating barcoded libraries for multiplex high-throughput sequencing. Methods Mol Biol. 2012;840:155-70. doi: 10.1007/978-1-61779-516-9_19.
Knight, et al. Subtle chromosomal rearrangements in children with unexplained mental retardation. Lancet. Nov. 13, 1999;354(9191):1676-81.
Korlach et al., Methods in Enzymology, Real-Time DNA Sequencing from Single Polymerase Molecules, (2010) 472:431-455.
Kozarewa, et al, "96-plex molecular barcoding for the Illumina Genome Analyzer", Methods Mol Biol., 733:279-98, 2011.
Kozarewa, et al. "Amplification-free Illumina sequencing-library preparation facilitates improved mapping and assembly of GC-biased genomes", Nat Methods., 6: 291-5, 2009.

(56) References Cited

OTHER PUBLICATIONS

Kwok, et al, "Single-molecule analysis for molecular haplotyping", Hum Mutat., 23:442-6, 2004.
Lai; et al., ""Characterization and Use of Laser-Based Lysis for Cell Analysis On-Chip", Journal of the Royal Society, Interface, vol. 5, Supplement 2, pp. S113-S121, Oct. 2008, (Year:2008)", Journal of the Royal Society, Interface, Oct. 2008, vol. 5, Supplement 2, S113-S121.
Laird et al, Hairpin-bisulfite PCR: Assessing epigenetic methylation patterns on complementary strands of individual DNA molecules, 2004, PNAS, 101, 204-209.
Lake, et al. "Integrative Single-Cell Analysis by Transcriptional and Epigenetic States in Human Adult Brain". Apr. 19, 2017. doi: https://doi.org/10.1101/128520.
Lan, et al. "Single-cell genome sequencing at ultra-high-throughput with microfluidic droplet barcoding" with Supplementary Material. Nat Biotechnol. May 29, 2017. doi: 10.1038/nbt.3880. [Epub ahead of print].
Lasken, et al. (1996) Archaebacterial DNA Polymerases Tightly Bind Uracil-containing DNA. The Journal of Biological Chemistry, 271(30):17692-17696 (Year: 1996).
Lebedev, A. et al. "Hot Start PCR with heat-activatable primers: a novel approach for improved PCR performance" NAR (2008) 36(20):E131-1.
Lee, et al. ACT-PRESTO: Rapid and consistent tissue clearing and labeling method for 3-dimensional (3D) imaging. Sci Rep. Jan. 11, 2016;6:18631. doi: 10.1038/srep18631.
Lee et al. Alginate: Properties and biomedical applications. Prog Polym Sci 37(1):106-126 (2012).
Lee, et al., "Highly multiplexed subcellular RNA sequencing in situ. Science. Mar. 21, 2014;343(6177):1360-3. doi: 10.1126/science.1250212. Epub Feb. 27, 2014."
Lee, J-H. et al. "Fluorescent in situ sequencing (FISSEQ) of RNA for gene expression profiling in intact cells and tissues" Nature Protocols (Feb. 12, 2015) 10(3):442-458.
"Lennon et al. A scalable, fully automated process for construction of sequence-ready barcoded libraries for 454. Genome Biology 11:R15 (2010)."
Li, et al. A single-cell-based platform for copy No. variation profiling through digital counting of amplified genomic DNA fragments. ACS Appl Mater Interfaces. Mar. 24, 2017. doi: 10.1021/acsami.7b03146. [Epub ahead of print].
Lienemann, et al. Single cell-laden protease-sensitive microniches for long-term culture in 3D. Lab Chip. Feb. 14, 2017;17(4):727-737. doi: 10.1039/c6lc01444e.
Linch, et al. Bone marrow processing and cryopreservation. Journal of Clinical Pathology; Feb. 1982, vol. 35, No. 2; pp. 186-190.
"List of sequenced bacterial genomes" (Wikipedia.com; accessed Jan. 24, 2014).
Lo, et al. On the design of clone-based haplotyping. Genome Biol. 2013;14(9):R100.
Lundin, et al, "Hierarchical molecular tagging to resolve long continuous sequences by massively parallel sequencing", Sci Rep., 3:1186, 2003.
Lupski. Genomic rearrangements and sporadic disease. Nat Genet. Jul. 2007;39(7 Suppl):S43-7.
Macaulay; et al., "G&T-seq: parallel sequencing of single-cell genomes and transcriptomes. Nature Methods, 2015, p. 1-7."
Macaulay, et al. Single-Cell Multiomics: Multiple Measurements from Single Cells. Trends in Genetics 33.2 (2017): 155-168. PMC. Web. Dec. 18, 2017.
Maricic T, et al. Optimization of 454 sequencing library preparation from small amounts of DNA permits sequence determination of both DNA strands. Biotechniques. Jan. 2009; 46(1):51-2, 54-7.
McGinnis, et al. MULTI-seq: Scalable sample multiplexing for single-cell RNA sequencing using lipid-tagged indices. bioRxiv 387241; doi: https://doi.org/10.1101/387241.
Miller JC, et al. An improved zinc-finger nuclease architecture for highly specific genome editing. Nat. Biotechnol. 2007;25:778-785.
Miller-Stephenson Chemicals 157 FS Series catalog, www.miller-stephenon.com.
MiRNA (http://www.exiqon.com/what-are-microRNAs) accessed Oct. 19, 2017.
Morgan, et al. Chapter 12: Human microbiome analysis. PLoS Comput Biol. 2012;8(12):e1002808. doi: 10.1371/journal.pcbi.1002808. Epub Dec. 27, 2012.
Morimoto, et al. Monodisperse semi-permeable microcapsules for continuous observation of cells. 2009. Lab Chip 9(15):2217-2223.
Mozhanova, A.A. et al. "Local elastic properties of biological materials studied by SFM" (2003) XP055314108, Retrieved from the Internet: URL:http://www.ntmdt.com/data/media/files/publications/2003/08.08_a.a.mozhanova_n.i.n_english.pdf.
Muotri, et al. L1 retrotransposition in neurons is modulated by MeCP2. Nature. Nov. 18, 2010;468(7322):443-6. doi: 10.1038/nature09544.
Myllykangas et al., Targeted Sequencing Library Preparation by Genomic DNA Circularization, BMC Biotechnology, 2011, 11(122), 1-12.
Nagano, et al. Single-cell Hi-C reveals cell-to-cell variability in chromosome structure. Nature. Oct. 3, 2013;502(7469):59-64. doi: 10.1038/nature12593. Epub Sep. 25, 2013.
Narayanan, J. et al. "Determination of agarose gel pore size: Absorbance measurements vis a vis other techniques" Journal of Physics: Conference Series 28 (2006) 83-86 (Year: 2006).
Oligotex Handbook. For purification of poly A+ RNA from total RNA and directly from cultured cells or tissues as well as purification of polyadenylated in vitro transcripts. Jun. 2012.
Orakdogen, N. "Novel responsive poly(N,N-dimethylaminoethyl methacrylate) gel beads: preparation, mechanical properties and pH-dependent swelling behavior" J Polym Res (2012) 19:9914.
Oyola, et al, "Optimizing Illumina next-generation sequencing library preparation for extremely AT-biased genomes", BMC Genomics., 13:1, 2012.
Pantel, et al. Detection methods of circulating tumor cells. J Thorac Dis. Oct. 2012;4(5):446-7. doi: 10.3978/j.issn.2072-1439.2012.08.15.
Park. ChIP-seq: advantages and challenges of a maturing technology. Nature Reviews Genetics vol. 10, pp. 669-680 (2009).
Patel, et al. Single-cell RNA-seq highlights intratumoral heterogeneity in primary glioblastoma. Science. Jun. 20, 2014;344(6190):1396-401. doi: 10.1126/science.1254257. Epub Jun. 12, 2014.
Perrott, Jimmy. Optimization and Improvement of Emulsion PCR for the Ion Torrent Next-Generation Sequencing Platform. (2011) Thesis.
Picot, J. et al. "A biomimetic microfluidic chip to study the circulation and mechanical retention of red blood cells in the spleen" Am J Hematology (Jan. 12, 2015) 90(4):339-345.
Pinto, et al. Functional impact of global rare copy number variation in autism spectrum disorders. Nature. Jul. 15, 2010;466(7304):368-72. doi: 10.1038/nature09146. Epub Jun. 9, 2010.
"Portable Water Filters" (http://www.portablewaterfilters.org/water-filter-guide/particle-contaminant-size-chart-microns/) 2015, accessed Oct. 19, 2017.
Porteus MH, Baltimore D. Chimeric nucleases stimulate gene targeting in human cells. Science. 2003;300:763.
Pott, et al. Single-cell ATAC-seq: strength in numbers. Genome Biol. Aug. 21, 2015;16:172. doi: 10.1186/s13059-015-0737-7.
Preissl, et al. Single nucleus analysis of the chromatin landscape in mouse forebrain development. Posted Jul. 4, 2017. bioRxiv 159137; doi: https://doi.org/10.1101/159137.
"U.S. Appl. No. 61/982,001, filed Apr. 21, 2014 (Year:2014)".
Rakszewska, A. et al. "One drop at a time: toward droplet microfluidics as a versatile tool for single-cell analysis" NPG Asia Materials (2014) 6(10):e133 (12 pages).
Ram, et al. Strategy for microbiome analysis using 16S rRNA gene sequence analysis on the Illumina sequencing platform. Syst Biol Reprod Med. Jun. 2011;57(3):162-70. doi: 10.3109/19396368.2011.555598. Epub Mar. 1, 2011.
Ramskold et al. (2012) "Full-length mRNA-Seq from single-cell levels of RNA and individual circulating tumor cells" Nature Biotechnology 30(8):777-782.

(56) References Cited

OTHER PUBLICATIONS

Ran et al. Genome engineering using the CRISPR-Cas9 system. Nature Protocols 8:2281-2308 (2013).
Reis, A. et al. "CRISPR/Cas9 and Targeted Genome Editing: A New Era in Molecular Biology" (2014) XP002766825: URL:https://ww.neb.com/tools-and-resources/feabture-articles/crispr-cas9-and-targeted-genome-editing-a-new-era-in-molecular-biology.
Reisner, et al, "Single-molecule denaturation mapping of DNA in nanofluidic channels", Proc Natl Acad Sci U.S.A., 107: 13294-9, 2010.
Repp et al. "Genotyping by Multiplex Polymerase Chain Reaction for Detection of Endemic Hepatitis B Virus Transmission" J Clinical Microbiology (1993) 31:1095-1102.
Richardson, et al. Novel inhibition of archaeal family-D DNA polymerase by uracil. Nucleic acids research 41.7 (2013): 4207-4218.
Roche. Using Multiplex Identifier (MID) Adaptors for the GS FLX Titanium Chemistry Basic MID Set Genome Sequencer FLX System, Technical Bulletin 004-2009, (Apr. 1, 2009) pp. 1-7. URL:http://454.com/downloads/my454/documentation/technical-bulletins/TCB-09004 UsingMultiplexIdentifierAdaptorsForTheGSFLXTitaniumSeriesChemistry-BasicMIDSet.pdf.
Roche. Using Multiplex Identifier (MID) Adaptors for the GS FLX Titanium Chemistry Extended MID Set Genome Sequencer FLX System, Technical Bulletin 005-2009, (Apr. 1, 2009) pp. 1-7. URL:http://454.com/downloads/my454/documentation/technical-bulletins/TCB-09005UsingMultiplexIdentifierAdaptorsForTheGSFLXTitaniumChemistry-ExtendedMIDSet.pdf.
Rodrigue, S. et al. "Whole genome amplification and de novo assembly of single bacterial cells" PLoS One. Sep. 2, 2009;4(9):e6864. doi: 10.1371/journal.pone.0006864.
Rogozin, et al. A highly conserved family of inactivated archaeal B family DNA polymerases. Biol Direct. Aug. 6, 2008;3:32. doi: 10.1186/1745-6150-3-32.
Ropers. New perspectives for the elucidation of genetic disorders. Am J Hum Genet. Aug. 2007;81(2):199-207. Epub Jun. 29, 2007.
Rotem, et al. Single-cell ChIP-seq reveals cell subpopulations defined by chromatin state. Nat Biotechnol. Nov. 2015;33(11):1165-72. doi: 10.1038/nbt.3383. Epub Oct. 12, 2015.
Sakaguchi, et al. (1996) Cautionary Note on the Use of dUMP-Containing PCR Primers with Pfu and VentR. Biotechniques, 21(3): 369-370 (Year: 1996).
Sander JD, et al. Selection-free zinc-finger-nuclease engineering by context-dependent assembly (CoDA). Nat. Methods. 2011;8:67-69.
Savva, et al. The structural basis of specific base-excision repair by uracil-DNA glycosylase. Nature. Feb. 9, 1995;373(6514):487-93.
Schmeider, et al. Fast identification and removal of sequence contamination from genomic and metagenomic datasets. PLoS One. Mar. 9, 2011;6(3):e17288. doi: 10.1371/journal.pone.0017288.
Schwartz, et al., "Capturing native long-range contiguity by in situ library construction and optical sequencing", PNAS (Nov. 2012), 109(46)18749-18754.
Sebat, et al. Strong association of de novo copy number mutations with autism. Science. Apr. 20, 2007;316(5823):445-9. Epub Mar. 15, 2007.
Shahi, et al. Abseq: Ultrahigh-throughput single cell protein profiling with droplet microfluidic barcoding. Sci Rep. 2017; 7: 44447. Published online Mar. 14, 2017. doi: 10.1038/srep44447.
Shlien, et al. Copy number variations and cancer. Genome Med. Jun. 16, 2009;1(6):62. doi: 10.1186/gm62.
Shlien, et al. Excessive genomic DNA copy number variation in the Li-Fraumeni cancer predisposition syndrome. Proc Natl Acad Sci U S A. Aug. 12, 2008;105(32):11264-9. doi: 10.1073/pnas.0802970105. Epub Aug. 6, 2008.
Shuttleworth, et al. Recognition of the pro-mutagenic base uracil by family B DNA polymerases from archaea. J Mol Biol. Mar. 26, 2004;337(3):621-34.
Sigma. Streptavidin-agarose (S1638) product information sheet. www.sigma-aldrich.com.

Simon, et al., "Using formaldehyde-assisted isolation of regulatory elements (FAIRE) to isolate active regulatory DNA", Nature Protocols, 2012, 7(2): 256-267.
Skerra. Phosphorothioate primers improve the amplification of DNA sequences by DNA polymerases with proofreading activity. Nucleic Acids Res. Jul. 25, 1992; 20(14):3551-4.
Smith, et al. Highly-multiplexed barcode sequencing: an efficient method for parallel analysis of pooled samples. Nucleic Acids Research, 38(13): e142 (2010).
Song, et al., "DNase-seq: A High-Resolution Technique for Mapping Active Gene Regulatory Elements across the Senome from Mammalian Cells", Cold Spring Harbor Laboratory Press, 2010, 2010(2), doi:10.1101/pdb.prot5384.
Spormann Laboratory, Polymerase Chain Reaction (PCR), Alfred Spormann Laboratory, 2009, 1-3. (Year: 2009).
Stoeckius, et al. Large-scale simultaneous measurement of epitopes and transcriptomes in single cells. bioRxiv 113068; doi: https://doi.org/10.1101/113068.
Stoeckius, et al. Simultaneous epitope and transcriptome measurement in single cells. Nature methods. Jul. 31, 2017. Supplemental Materials.
Susaki, et al. Whole-brain imaging with single-cell resolution using chemical cocktails and computational analysis. Cell. Apr. 24, 2014;157(3):726-39. doi: 10.1016/j.cell.2014.03.042. Epub Apr. 17, 2014.
Syed, et al. Next-generation sequencing library preparation: simultaneous fragmentation and tagging using in vitro transposition. Nature Methods 2 pgs (Nov. 2009).
Tayyab, S. et al. "Size exclusion chromatography and size exclusion HPLC of proteins" Biochem Ed, Pergamon, (1991) 19(3):149-152.
Tewhey et al., Supplementary Materials, Nature Biotechnology, 2009, 27(11), 1-22.
ThermoFisher, Protocols, M-270 Streptavidin, ThermoFisherScientific, 2007, 1-5. (Year: 2007).
Tomer, et al. Advanced CLARITY for rapid and high-resolution imaging of intact tissues. Nat Protoc. Jul. 2014;9(7):1682-97. doi: 10.1038/nprot.2014.123. Epub Jun. 19, 2014.
Turner, et al. Assaying chromosomal inversions by single-molecule haplotyping. Nat Methods. Jun. 2006;3(6):439-45.
Turner, et al, "High-throughput haplotype determination over long distances by haplotype fusion PCR and ligation haplotyping", Nat Protoc., 4:1771-83, 2009.
Ushijima et al, Detection and interpretation of altered methylation patterns in cancer cells, 2005, Nature reviews, 5, 223-231.
Van Nieuwerburgh, et al, "Illumina mate-paired DNA sequencing-library preparation using Cre-Lox recombination", Nucleic Acids Res., 40:1-8, 2012.
Wang, et al. Digital karyotyping. Proc Natl Acad Sci U S A. Dec. 10, 2002;99(25):16156-61. Epub Dec. 2, 2002.
Wang et al., "Self-Formed Adaptor PCR: a Simple and Efficient Method for Chromosome Walking", Applied and Environmental Microbiology (Aug. 2007), 73(15):5048-5051.
Wesolowska, et al. Cost-effective multiplexing before capture allows screening of 25 000 clinically relevant SNPs in childhood acute lymphoblastic leukemia. Leukemia. Jun. 2011;25(6):1001-6. doi: 10.1038/leu.2011.32. Epub Mar. 18, 2011.
Wiseman, R.W. et al. "Major histocompatibility complex genotyping with massively parallel pyrosequencing" Nature Medicine (Oct. 11, 2009) 15(11):1322-1326.
Wong, et al. Multiplexed Barcoded CRISPR-Cas9 Screening Enabled by CombiGEM. PNAS. Mar. 1, 2016, vol. 113, pp. 2544-2549.
Wood AJ, et al. Targeted genome editing across species using ZFNs and TALENs. Science. 2011;333:307.
Xi, et al. New library construction method for single-cell genomes. PLoS One. Jul. 19, 2017;12(7):e0181163. doi: 10.1371/journal.pone.0181163. eCollection 2017.
Xia and Whitesides, Soft Lithography, Angew. Chem. Int. Ed. 37:550-575 (1998).
Xiao, et al, "Determination of haplotypes from single DNA molecules: a method for single-molecule barcoding", Hum Mutat., 28:913-21, 2007.
Yan, Pu et al. "Rapid one-step construction of hairpin RNA" Biochem and Biophys Res Comm (Jun. 12, 2009) 383(4):464-468.

(56) References Cited

OTHER PUBLICATIONS

Zentner, et al. Surveying the epigenomic landscape, one base at a time. Genome Biol. Oct. 22, 2012;13(10):250. doi: 10.1186/gb4051.
Zhang, et al. Reconstruction of DNA sequencing by hybridization. Bioinformatics. Jan. 2003;19(1):14-21.
Zhang F, et al. Efficient construction of sequence-specific TAL effectors for modulating mammalian transcription. Nat. Biotechnol. 2011;29:149-153.
Zhang. Genomics of inherited bone marrow failure and myelodysplasia. Dissertation [online]. University of Washington. 2015 [Retrieved on May 3, 2017].
Zheng, et al. Massively parallel digital transcriptional profiling of single cells. Nat Commun. Jan. 16, 2017;8:14049. doi: 10.1038/ncomms14049.
Zheng, X.Y. et al. "Haplotyping germline and cancer genomes with high-throughput linked-read sequencing" Nature Biotech (Feb. 1, 2016) 34(3):303-311.
Zhou, Y. et al. "Development of an enzyme activity screening system for p-glucosidase-displaying yeasts using calcium alginate micro-beads and flow sorting" Appl Microbiol Biotechnol (2009) 84:375-382 (Year: 2009).
Zhu et al. Hydrogel Droplet Microfluidics for High-Throughput Single Molecule/Cell Analysis. Accounts of Chemical Research Article ASAP. DOI: 10.1021/acs.accounts.6b00370.
Zhu, et al. Reverse transcriptase template switching: a SMART approach for full-length cDNA library construction. Biotechniques. Apr. 2001;30(4):892-7.
Co-pending U.S. Appl. No. 16/419,820, filed May 22, 2019.
U.S. Appl. No. 17/545,812, Freitas et al.

\* cited by examiner

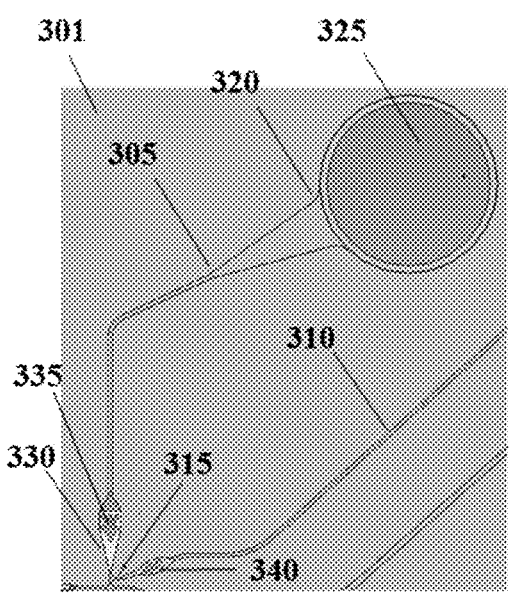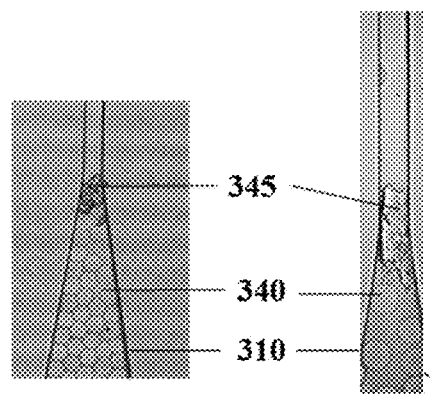
*FIG. 3A*  *FIG. 3B*  *FIG. 3C*

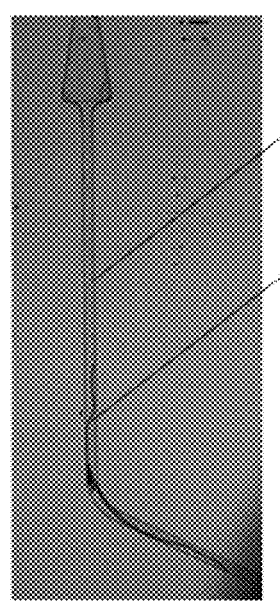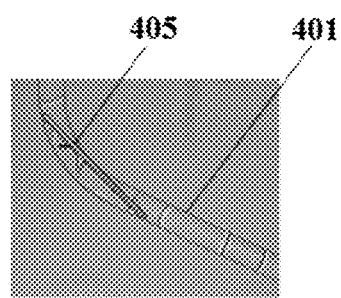
FIG. 4A
FIG. 4B

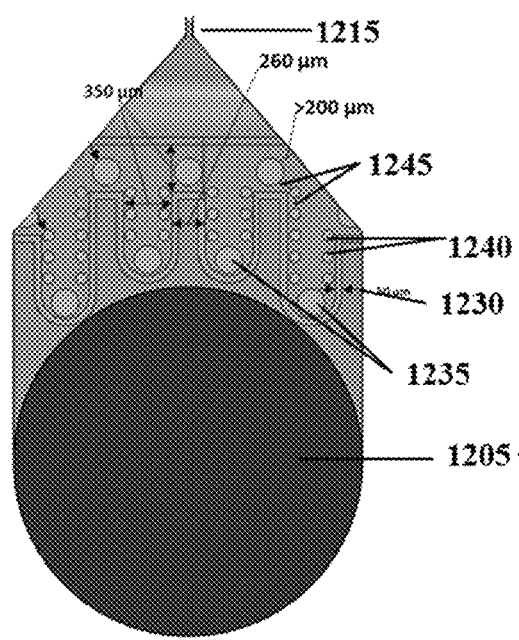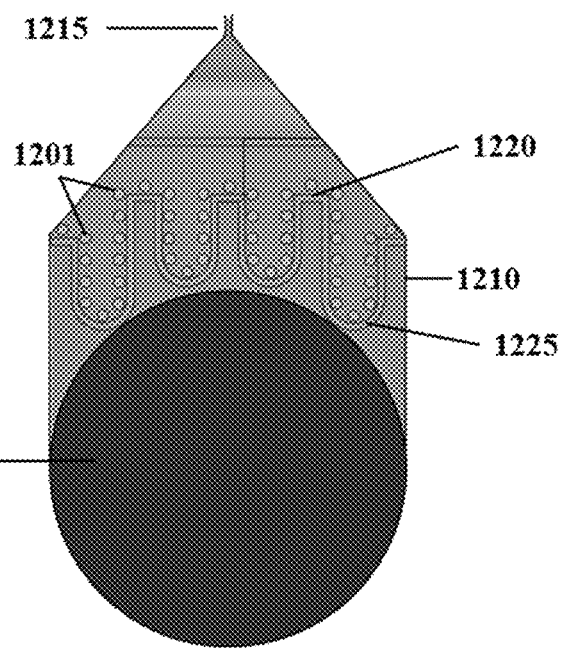
*FIG. 12A*  *FIG. 12B*

MICROFLUIDIC ON-CHIP FILTERS

CROSS-REFERENCE

This application is a continuation of PCT Patent Application No. PCT/US2017/32525, filed May 12, 2017, which claims the benefit of U.S. Provisional Patent Application No. 62/335,216, filed May 12, 2016, each of which applications is entirely incorporated herein by reference.

BACKGROUND

Microfluidic systems may be used in various applications, such as biological sample processing, for example, for generating monodisperse populations of microcapsules or beads that may have reagents such as biological reagents associated therewith. Further, the microfluidic systems may be used for selectively and controllably partitioning these microcapsules or beads into droplets in emulsions for use in performing further reactions and/or analyses. Such systems may include a network of channels, and actuators for directing fluids through the network of channels. The network of channels can further comprise one or more flow controlling structures that provide a flow rate.

A microfluidic system may include a repository of biological material in fluid communication with a first channel and a micropump for subjecting the biological material to flow through the channel. The biological material, while flowing through the first channel, may be subjected to reagents in a second channel for generating emulsion at an intersection of the first channel and the second channel. The microfluidic system may be fluidly connected to an output reservoir for collecting a released biological material that was subjected to flow through the channel. The released biological material may comprise droplets in emulsions.

A microfluidic system may be integrated in a chip. The chip may be used to process a biological sample. The chip may further comprise a plurality of compartments. At least one compartment may be in fluid communication with the repository of biological material that may or may not be associated with the reagents. At least one compartment may be in fluid communication with the output reservoir. The plurality of compartments may be in communication with each other via the network of channels. The chip may be compatible with a plurality of devices for further analyzing the processed biological material. The plurality of devices may comprise high throughput next generation sequencing platforms, nucleic acid amplification systems and nucleic acid manipulation systems.

SUMMARY

Such systems, including microfluidic channels and features, have proven useful tools for fluid and particle manipulations in a variety of applications. As microfluidic channel dimensions decrease, however, the likelihood of blockage in such channels (i.e., blocking rate or clogging rate) may increase. Such blockage can occur due to debris from consumables (e.g., pipette tips and reagent troughs), environment (e.g., airborne particulate that settles into chip wells) or due to debris/clumps in reagents themselves.

Such blockage can be an issue with gel bead emulsion reagent processing, for example, because (a) the gel bead solution may be a two-phase suspension flow that is more susceptible to blockage, and (b) the gel bead solution may have more debris compared to other single phase reagents (e.g., oil, aqueous solutions) due to the large number of processing steps involved in generating gel beads. Accordingly, recognized herein is the need for on-chip solutions to reduce blocking of microfluidic systems employing particles and emulsions, for example, gel bead emulsions.

In an aspect, the present disclosure provides a microfluidic device for filtering particles in a fluid. The microfluidic device comprises (i) a reservoir for holding the fluid comprising the particles; (ii) a channel in fluid communication with the reservoir; and (iii) at least one filter feature in the channel, where the at least one filter feature comprises a field of a plurality of physical obstacles configured and arranged in the channel, where the at least one filter feature separates the particles in the fluid upon flow of the fluid from the reservoir through the channel, and where the channel comprises a first end and a second end, where the first end is adjacent to the reservoir, and where a cross-section of the channel decreases along a direction leading from the first end to the second end.

In some embodiments, the reservoir, the channel and at least one filter feature are integrated in a chip. In some embodiments, the chip comprises a plurality of compartments in fluid communication with the reservoir. In some embodiments, at least one compartment of the plurality of compartments is in fluid communication with the reservoir, which reservoir includes the particles. In some embodiments, at least one compartment of the plurality of compartments is in fluid communication with an output reservoir that collects the particles.

In some embodiments, the plurality of physical obstacles is distributed in an array of physical obstacles. In some embodiments, the plurality of physical obstacles includes a plurality of cylinders each having a cross-sectional dimension and a vertical dimension arranged within the field. In some embodiments, cross-sectional dimensions and vertical dimensions of at least a subset of the plurality of cylinders are the same. In some embodiments, at least a subset of the plurality of cylinders have different cross-sectional dimensions and vertical dimensions.

In some embodiments, the plurality of cylinders arranged in a plurality of concentric rings where an innermost ring is in fluid communication with the reservoir. In some embodiments, the plurality of concentric rings comprises at least two rings. In some embodiments, the plurality of concentric rings comprises an inner ring and an outer ring. In some embodiments, the inner ring comprises a first subset of the plurality of cylinders having larger cross-sectional dimensions and/or vertical dimensions than a second subset of the plurality of cylinders in the outer ring.

In some embodiments, the plurality of cylinders are arranged in a serpentine configuration in fluid communication with the reservoir. In some embodiments, the serpentine configuration includes at least one convex portion comprising a subset of the plurality of cylinders, which convex portion is in fluid communication with the reservoir.

In some embodiments, the direction is oriented along a direction of a gravitational acceleration vector. In some embodiments, the direction is oriented along a direction of a pressure increase or decrease along a direction leading from the first end to the second end.

In some embodiments, the at least one filter feature comprises at least one passage with a cross-section that is greater than or equal to an average diameter of the particle in the fluid among other particles in the fluid. In some embodiments, the at least one filter feature comprises at least one passage with a cross-section that is less than an average diameter of the particle in the fluid among other particles in the fluid.

In some embodiments, the particles are contaminants. In some embodiments, the particles are beads. In some embodiments, the particles are gel beads. In some embodiments, the particles are cellular components. In some embodiments, the particles are cells. In some embodiments, the cells include or are enclosed in a gel or a polymer matrix. In some embodiments, the cellular components include one or more members selected from the group consisting of cell membrane, cell wall, organelles, macromolecular constituent(s), deoxyribonucleic acid (DNA), and ribonucleic acid (RNA).

In some embodiments, the particles are comprised in a population of particles. In some embodiments, the population of particles is homogeneous. In some embodiments, the population of particles is heterogeneous.

In some embodiments, the particles include barcodes coupled thereto. In some embodiments, the barcodes are nucleic acid molecules comprising nucleic acid sequences. In some embodiments, the barcodes across at least a subset of the particles are different.

In some embodiments, the channel comprises at least one constriction between the first end and the second end to reduce a concentration of air trapped in the filter feature. In some embodiments, the channel comprises at least two constrictions on opposite sides of the channel between the first end and the second end to reduce a concentration of air trapped in the filter feature. In some embodiments, the channel comprises at least one passive valve and at least one rectifier and the at least one filter feature is between the at least one passive valve and the at least one rectifier.

In an additional aspect, the present disclosure provides a system for filtering particles in a fluid. The system comprises a microfluidic device comprising (i) a reservoir for holding the fluid comprising the particles, (ii) a channel in fluid communication with the reservoir, and (iii) at least one filter feature in the channel, where the at least one filter feature comprises a field of a plurality of physical obstacles configured and arranged in the channel, where the at least one filter feature separates the particles in the fluid upon flow of the fluid from the reservoir through the channel, and where the channel comprises a first end and a second end, where the first end is adjacent to the reservoir, and where a cross-section of the channel decreases along a direction leading from the first end to the second end; and a controller operatively coupled to the microfluidic device, where the controller subjects the fluid to flow from the reservoir to the channel.

In some embodiments, the reservoir, the channel and at least one filter feature are integrated in a chip. In some embodiments, the chip comprises a plurality of compartments in fluid communication with the reservoir. In some embodiments, at least one compartment of the plurality of compartments is in fluid communication with the reservoir, which reservoir includes the particles. In some embodiments, at least one compartment of the plurality of compartments is in fluid communication with an output reservoir that collects the particles.

In some embodiments, the plurality of physical obstacles is distributed in an array of physical obstacles. In some embodiments, the plurality of physical obstacles includes a plurality of cylinders each having a cross-sectional dimension and a vertical dimension arranged within the field. In some embodiments, cross-sectional dimensions and vertical dimensions of at least a subset of the plurality of cylinders are the same. In some embodiments, at least a subset of the plurality of cylinders have different cross-sectional dimensions and vertical dimensions.

In some embodiments, the plurality of cylinders arranged in a plurality of concentric rings where an innermost ring is in fluid communication with the reservoir. In some embodiments, the plurality of concentric rings comprises at least two rings. In some embodiments, the plurality of concentric rings comprises an inner ring and an outer ring. In some embodiments, the inner ring comprises a first subset of the plurality of cylinders having larger cross-sectional dimensions and/or vertical dimensions than a second subset of the plurality of cylinders in the outer ring.

In some embodiments, the plurality of cylinders are arranged in a serpentine configuration in fluid communication with the reservoir. In some embodiments, the serpentine configuration includes at least one convex portion comprising a subset of the plurality of cylinders, which convex portion is in fluid communication with the reservoir.

In some embodiments, the direction is oriented along a direction of a gravitational acceleration vector. In some embodiments, the direction is oriented along a direction of a pressure increase or decrease along a direction leading from the first end to the second end.

In some embodiments, the at least one filter feature comprises at least one passage with a cross-section that is greater than or equal to an average diameter of the particle in the fluid among other particles in the fluid. In some embodiments, the at least one filter feature comprises at least one passage with a cross-section that is less than an average diameter of the particle in the fluid among other particles in the fluid.

In some embodiments, the particles are contaminants. In some embodiments, the particles are beads. In some embodiments, the particles are gel beads. In some embodiments, the particles are cellular components. In some embodiments, the particles are cells. In some embodiments, the cells include or are enclosed in a gel or polymer matrix. In some embodiments, the cellular components include one or more members selected from the group consisting of cell membrane, cell wall, organelles, macromolecular constituent(s), deoxyribonucleic acid (DNA), and ribonucleic acid (RNA).

In some embodiments, the particles are comprised in a population of particles. In some embodiments, the population of particles is homogeneous. In some embodiments, the population of particles is heterogeneous.

In some embodiments, the particles include barcodes coupled thereto. In some embodiments, the barcodes are nucleic acid molecules comprising nucleic acid sequences. In some embodiments, the barcodes across at least a subset of the particles are different.

In some embodiments, the channel comprises at least one constriction between the first end and the second end to reduce a concentration of air trapped in the filter feature. In some embodiments, the channel comprises at least two constrictions on opposite sides of the channel between the first end and the second end to reduce a concentration of air trapped in the filter feature. In some embodiments, the channel comprises at least one passive valve and at least one rectifier and the at least one filter feature is between the at least one passive valve and the at least one rectifier.

In an additional aspect, the present disclosure provides a method for filtering particles in a fluid. The method comprises (a) activating a microfluidic device comprising (i) a reservoir for holding the fluid comprising the particles, (ii) a channel in fluid communication with the reservoir, and (iii) at least one filter feature in the channel, where the at least one filter feature comprises a field of a plurality of physical obstacles configured and arranged in the channel, where the channel comprises a first end and a second end, where the first end is adjacent to the reservoir, and where a cross-section of the channel decreases along a direction leading from the first end to the second end; and (b) subjecting the fluid to flow from the reservoir to the channel, where upon flow of the fluid from the reservoir through the channel, the at least one filter feature separates the particles in the fluid.

In some embodiments, the method further comprises collecting the particles in an output reservoir. In some embodiments, the method further comprises directing the particles collected in the output reservoir to further processing. In some embodiments, the method further comprises directing the particles to partitions. In some embodiments, the partitions are droplets. In some embodiments, the partitions are wells.

In some embodiments, the particles include contaminants. In some embodiments, the particles include beads. In some embodiments, the particles include cellular components. In some embodiments, the particles include cells. In some embodiments, the cellular components include one or more members selected from the group consisting of cell membrane, cell wall, organelles, macromolecular constituent(s), deoxyribonucleic acid (DNA), and ribonucleic acid (RNA).

In some embodiments, the particles include barcodes coupled thereto. In some embodiments, the barcodes are nucleic acid molecules comprising nucleic acid sequences. In some embodiments, the barcodes across at least a subset of the particles are different.

In some embodiments, the fluid is subjected to flow with the aid of a pressure increase or decrease along a direction leading from the first end to the second end.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIGS. 3A-3C provides photomicrographs of an example microfluidic device.

FIGS. 4A-4B provides photomicrographs of an example channel blocked by a fiber.

FIGS. 12A-12B schematically illustrates an example of at least one filter feature in a serpentine arrangement with two configurations and provides dimensions for parts of the serpentine arrangements.

DETAILED DESCRIPTION

Figure 1:
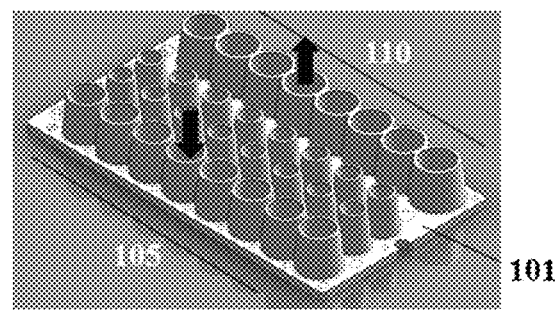
FIG. 1 schematically illustrates an example microfluidic device with a plurality of compartments.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The term "barcode," as used herein, generally refers to a label, or identifier, that conveys or is capable of conveying information about an analyte. A barcode can be part of an analyte. A barcode can be a tag attached to an analyte (e.g., nucleic acid molecule) or a combination of the tag in addition to an endogenous characteristic of the analyte (e.g., size of the analyte or end sequence(s)). A barcode may be unique. Barcodes can have a variety of different formats. For example, barcodes can include: polynucleotide barcodes; random nucleic acid and/or amino acid sequences; and synthetic nucleic acid and/or amino acid sequences. A barcode can be attached to an analyte in a reversible or irreversible manner. A barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads in real time.

The term "genome," as used herein, generally refers to genomic information from a subject, which may be, for example, at least a portion or an entirety of a subject's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together may constitute a human genome.

The terms "adaptor(s)", "adapter(s)" and "tag(s)" may be used synonymously. An adaptor or tag can be coupled to a polynucleotide sequence to be "tagged" by any approach including ligation, hybridization, or other approaches.

The term "sequencing," as used herein, generally refers to methods and technologies for determining the sequence of nucleotide bases in one or more polynucleotides. The polynucleotides can be, for example, deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina, Pacific Biosciences, Oxford Nanopore, or Life Technologies (Ion Torrent). As an alternative, sequencing may be performed using nucleic acid amplification, polymerase chain reaction (PCR) (e.g., digital PCR, quantitative PCR, or real time PCR) or isothermal amplification. Such devices may provide a plurality of raw genetic data corresponding to the genetic information of a subject (e.g., human), as generated by the device from a sample provided by the subject. In some situations, systems and methods provided herein may be used with proteomic information.

The term "bead," as used herein, generally refers to a particle. The bead may be a solid or semi-solid particle. The bead may be a gel bead. The bead may be formed of a polymeric material. The bead may be magnetic or non-magnetic.

The term "sample," as used herein, generally refers to a biological sample of a subject. The biological sample may be a nucleic acid sample or protein sample. The biological sample may be derived from another sample. The sample may be a tissue sample, such as a biopsy, core biopsy, needle aspirate, or fine needle aspirate. The sample may be a fluid sample, such as a blood sample, urine sample, or saliva sample. The sample may be a skin sample. The sample may be a cheek swap. The sample may be a plasma or serum sample. The sample may be a cell-free or cell free sample. A cell-free sample may include extracellular polynucleotides. Extracellular polynucleotides may be isolated from a bodily sample that may be selected from the group consisting of blood, plasma, serum, urine, saliva, mucosal excretions, sputum, stool and tears.

The term "biological particle," as used herein, generally refers to a discrete biological system derived from a biological sample. The biological particle may be a virus. The biological particle may be a cell or derivative of a cell. The biological particle may be an organelle. The biological particle may be a rare cell from a population of cells. The biological particle may be any type of cell, including without limitation prokaryotic cells, eukaryotic cells, bacterial, fungal, plant, mammalian, or other animal cell types, mycoplasmas, normal tissue cells, tumor cells, or any other cell type, whether derived from single cell or multicellular organisms. The biological particle may be obtained from a tissue of a subject. Biological particles may be disruptable particles.

The biological particle may be a hardened cell. Such hardened cell may or may not include a cell wall or cell membrane. The biological particle may include one or more constituents of a cell, but may not include other constituents of the cell. A cell may be a live cell. The live cell may be capable of being cultured, for example, being cultured when enclosed in a gel or polymer matrix, or cultured when comprising a gel or polymer matrix.

The term "macromolecular constituent," as used herein, generally refers to a macromolecule contained within a biological particle. The macromolecular constituent may comprise a nucleic acid. The macromolecular constituent may comprise deoxyribonucleic acid (DNA). The macromolecular constituent may comprise ribonucleic acid (RNA). The macromolecular constituent may comprise a protein. The macromolecular constituent may comprise a peptide. The macromolecular constituent may comprise a polypeptide.

The term "molecular tag," as used herein, generally refers to a molecule capable of binding to a macromolecular constituent. The molecular tag may bind to the macromolecular constituent with high affinity. The molecular tag may bind to the macromolecular constituent with high specificity. The molecular tag may comprise a nucleotide sequence. The molecular tag may comprise an oligonucleotide or polypeptide sequence. The molecular tag may comprise a DNA aptamer. The molecular tag may be or comprise a primer. The molecular tag may be or comprise a protein. The molecular tag may comprise a polypeptide. The molecular tag may be a barcode.

The efficiency of many single cell applications can increase by improving cell throughput. For example, this can be achieved by sorting a plurality of droplets that may or may not contain cells and/or particles therein to collect only the droplets that contain the cells and/or particles therein. The isolated population of droplets that contain the cells and/or particles therein can then be subject to further applications, such as nucleic acid amplification and/or sequencing applications.

Apparatuses and Systems

In an aspect, the present disclosure provide a microfluidic device for filtering particles in a fluid. The microfluidic device may include a reservoir for holding the fluid comprising the particles, a channel in fluid communication with the reservoir, at least one filter feature in the channel. The at least one filter feature may comprise a field of a plurality of physical obstacles configured and arranged in the channel. The at least one filter feature may separate the particles in the fluid upon flow of the fluid from the reservoir through the channel.

For example, the at least one filter feature may retain the particles and permit the fluid to flow through, thereby separating the particles from the fluid. As another example, the at least one filter feature may separate a first subset of particles (e.g., gel beads) from a second subset of particles (e.g. contaminants or debris), to permit the fluid with the first subset of particles to flow through with a decrease in an amount or concentration of the second subset of particles or contaminants or debris.

The channel may comprise a first end and a second end, wherein the first end is adjacent to the reservoir. A cross-section of the channel may decrease along a direction leading from the first end to the second end. The cross-section may be tapered or chamfered. For example, the cross-section gradually decreases.

The reservoir, the channel and the at least one filter feature may be integrated in a chip. For example, the chip may include the reservoir, the channel and the at least one filter feature as a single piece unit. The chip may comprise a plurality of compartments in fluid communication with the reservoir. At least one compartment of the plurality of compartments may be in fluid communication with the reservoir. The reservoir may include the particles.

As shown in FIG. 1, a microfluidic device 101 may comprise a plurality of compartments. The plurality of compartments may further comprise a first subset of compartments 105 and a second subset of compartments 110. The first subset of compartments 105 may be in fluid communication with a reservoir (not shown). The reservoir may include the particles in a fluid. The first subset of compartments 105 may receive the fluid with the particles from the reservoir. The first subset of compartments 105 may direct the fluid through a network of channels (not shown) in the microfluidic device 101. The network of channels may connect to the first subset of compartments 105 with a first end and may further connect to the second subset of compartments 110 with a second end.

The second set of compartments 110 may be in fluid communication with an output reservoir (not shown). The fluid comprising the particles (e.g., cells) may be subjected to filtration in the channels. The channels may comprise the at least one filter feature (not shown). The at least one filter feature may filter the cells that may further be collected through the second set of compartments 110. The cells after filtration may be released in the output reservoir and the cells may then be collected from the output reservoir. The output reservoir may hold the particles for further processing, for example, sample preparation for assaying (e.g., sequencing). The output reservoir may direct the particles to partitions, such as to droplets and wells. The wells may further include an array of wells on a plate.

Figure 2:
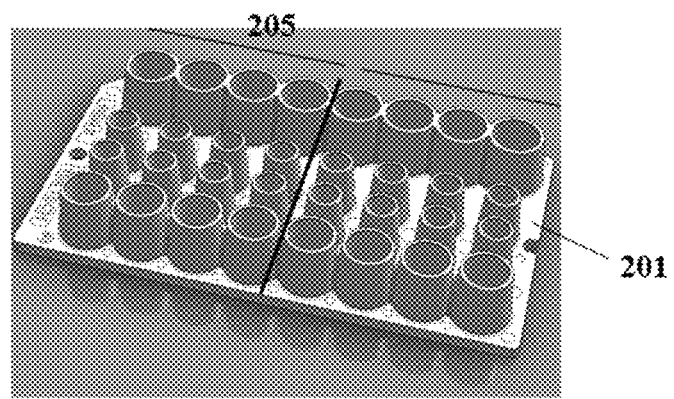
FIG. 2 schematically illustrates an example microfluidic device with a plurality of compartments.

In another example, as shown in FIG. 2, the microfluidic device 201 may comprise a plurality of compartments. The plurality of compartments may further comprise a first subset of compartments 205 and a second subset of compartments 210. The first subset of compartments 205 may be in fluid communication with a reservoir (not shown) and may receive a fluid with particles (e.g., cells and a gel or a matrix) from the reservoir to produce cell beads. The cell beads may be directed to the second subset of compartments 210 for filtering the cell beads. A first end of a network of channels (not shown) may be in fluid communication with the first subset of compartments 205 and may receive the cell beads. The network of channels may carry the cell beads for filtration to the second subset of compartments 210. A second end of the network of channels may be in fluid communication with the second subset of compartments 210. The cell beads may be collected from the second set of compartments 210 after filtration. The cell beads may be released in an output reservoir (not shown) after filtration. The cells beads may be collected from the output reservoir. The output reservoir may hold the particles for further processing, for example, sample preparation for assaying (e.g., sequencing). The output reservoir may direct the particles to partitions, such as to droplets and wells. The wells may further include an array of wells on a plate.

In another example, as shown in FIG. 3, the microfluidic device 301 may comprise a network of channels. The network of channels may comprise a first channel 305 and a second channel 310 that may intersect at an intersection 315. A first end 320 of the first channel may be in fluid communication with a reservoir 325, and a second end 330 of the first channel may be in fluid communication with the second channel 310 at the intersection 315. The first end 320 of the first channel 305 may taper toward the second end 330 of the first channel. For example, a cross-sectional dimension of the first end 320 may be larger than a cross-sectional dimension of the second end 330. The first channel 305 may carry a fluid with particles (e.g., debris or fibers or contaminants). The second end 330 of the first channel 305 may comprise at least one filter feature 335 that may separate the particles in the fluid before fluidly connecting with the second channel 310. The second channel 310 may comprise at least one filter feature (not shown). The at least one filter feature in the second channel 310 may reduce concentration of particles (e.g. debris) associated with the gel beads 340. The second channel 310 may not comprise the at least one filter feature and may be subjected to blockage by the particles (e.g. debris) 345 associated with the gel beads. The blockage in the second channel 310 may affect flow of the gel beads to the intersection 315.

In another example, as shown in FIG. 4 A-B, a channel 401 carrying a fluid may be blocked by particles (e.g., fibers) 405. Fibers 405 may block the channel 401 and may affect flow of the fluid.

The at least one filter feature may be located at the first end of the channel, also called as a "funnel filter". The at least one filter feature may be located at the second end of the channel, also called as a "channel filter". The funnel filter in the channel may be useful in separating particles that are larger in size and are rigid, such as, fibers. The channel filter may be useful in separating particles that are smaller in size, such as contaminants in reagents.

The at least one filter feature may comprise a plurality of physical obstacles. The plurality of obstacles may be located on both the first end and the second end. For example, the channel may comprise both the funnel filter and the channel filter. The plurality of obstacle may be located at either the first end or the second end of the channel. For example, the channel may comprise either the funnel filter or the channel filter. The channel may include a plurality funnel filters. The channel may include a plurality of channel filters. The may include combination of the plurality of funnel filters and the plurality of channel filters.

Figure 5A:
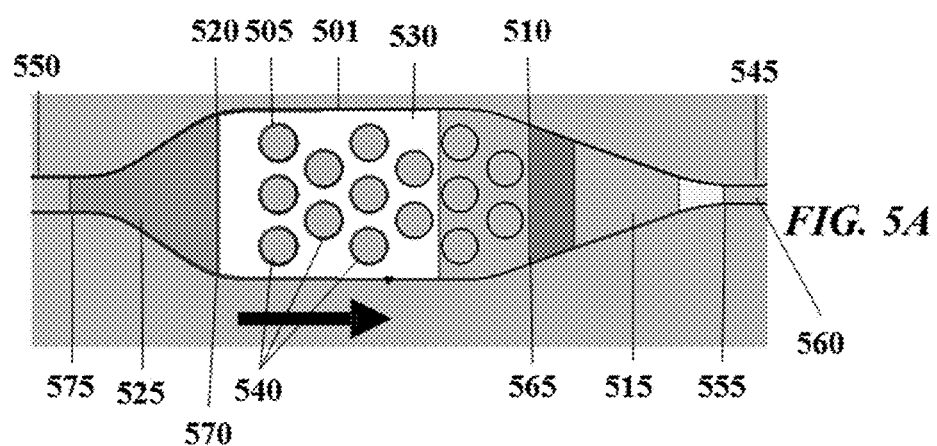
FIGS. 5A-5C schematically illustrates an example of at least one filter feature integrated with at least one passive valve and at least one rectifier in a channel.
Figure 5B:
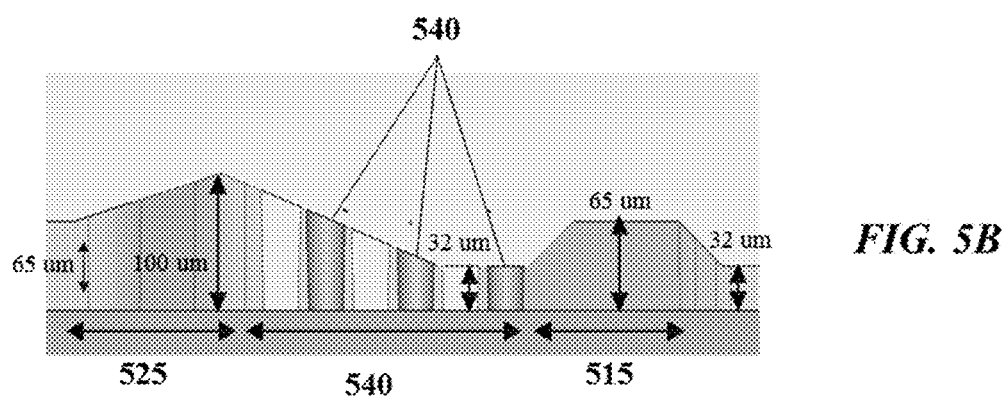
Figure 5C:
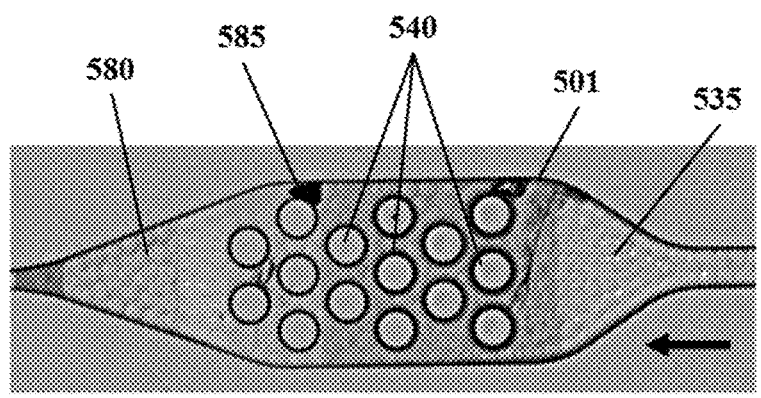

The at least one filter feature in a channel may be configured to reduce a concentration of air trapped in the at least one filter feature. For example, as shown in FIG. 5, the channel 501 may comprise at least one filter feature 505. A first end of at least one filter feature 510 may be in contact with at least one passive valve 515. A second end of at least one filter feature 520 may be in contact with at least one rectifier 525. The channel 501 may carry a fluid 530 with particles (e.g., gel beads, debris, fibers) 535 having a direction of flow as indicated by an arrow in FIG. 5A and FIG. 5C.

The at least one filter feature 505 may comprise a plurality of physical obstacles 540. The plurality of physical obstacles 540 may be arranged in a staggered arrangement. The plurality of physical obstacles 540 in the staggered arrangement may have alternating rows of odd and even number of the plurality of physical obstacles 540. The plurality of physical obstacles 540 may have a vertical dimension. The vertical dimension of the plurality of physical obstacles 540 may be identical. The vertical dimension of a given subset in the plurality of physical obstacles 540 may be different. For example, as shown in FIG. 5B, the vertical dimension of a first subset of the plurality of physical obstacles may be at least about 10 micrometer (µm), at least about 20 µm, at least about 30 µm, at least about 40 µm, at least about 50 µm, at least about 60 µm, at least about 100 µm or more. Further, the vertical dimension of a second subset of the plurality of physical obstacles may be at least about 60 µm. Furthermore, the vertical dimension of a second subset of the plurality of physical obstacles may be at least about 10 µm, at least about 25 µm, at least about 50 µm, at least about 60 µm, at least about 75 µm, at least about 100 µm, at least about 110 µm, at least about 125 µm, at least about 150 µm, at least about 175 µm, at least about 200 µm or more.

The at least one passive valve 515 may regulate flow of the fluid 530 through the channel 501 in the microfluidic device. The at least one passive valve 515 may be configured to open when a fluid pressure in a first end of channel 545 is greater than fluid pressure in a second end of channel 550. In another example, the at least one passive valve 515 may be configured to open when a fluid pressure in a first channel is greater than a fluid pressure in a second channel (not shown in FIG. 5). A first end of at least one passive valve 555 may be in fluid communication with a reservoir 560. A second end of at least one passive valve 565 may be in fluid communication with the first end of at least one filter feature 510. The at least one passive valve 515 may regulate the fluid pressure entering the at least one filter feature 505. The at least one passive valve 515 may have a vertical dimension. The vertical dimension of the first end of at least one passive valve and the second end of at least one passive valve may be identical. The vertical dimension of the first end of at least one passive valve 555 and the second end of at least one passive valve 565 may be different. For example, as shown in FIG. 5B, the vertical dimension of the first end of at least one passive valve 555 may be narrower than the cross-sectional dimension of the second end of at least one passive valve 565. The vertical dimension of the first end of at least one passive valve 555 may be at least about 32 micrometer (µm) and the cross-sectional dimension of the second end of at least one passive valve 565 may be at least about 65 µm.

The second end of at least one filter feature 520 may be in contact with a first end of at least one rectifier 570. The at least one filter feature 505 may be in between the at least one passive valve 515 and the at least one rectifier 525. The at least one rectifier 525 may facilitate operation of the microfluidic device by allowing the fluid to traverse through the channel 501 from the first end of channel 545 toward the second end of channel 550. The at least one rectifier 525 may have different shapes, such as triangular, hyperbolic or other geometric shapes. The at least one rectifier 525 may have a vertical dimension. The vertical dimension of the first end of at least one rectifier and a second end of at least one rectifier may be identical. The vertical dimension of the first end of at least one rectifier 570 and the second end of at least one rectifier 575 may be different. For example, as shown in FIG. 5B, the vertical dimension of the first end of at least one rectifier 570 may be broader than the cross-sectional dimension of the second end of at least one rectifier 575. The vertical dimension of the first end of at least one rectifier 570 may be at least about 100 micrometer (µm) and the vertical dimension of the second end of at least one rectifier 575 may be at least about 65 µm.

The fluid with particles may flow through the plurality of physical obstacles in the directed indicated by the arrow in FIG. 5A and FIG. 5C. The particles may comprise a first subset of particles (e.g., gel beads) 580 and a second subset of particles (e.g., debris, fibers or contaminants) 585. The first subset of particles 580 may be released toward the second end of channel. The second subset of particles 585 may be trapped in the plurality of physical obstacles 540. The plurality of physical obstacles 540 may be useful in separating the second subset of particles 580 associated with the first subset of particles 585.

Figure 6:
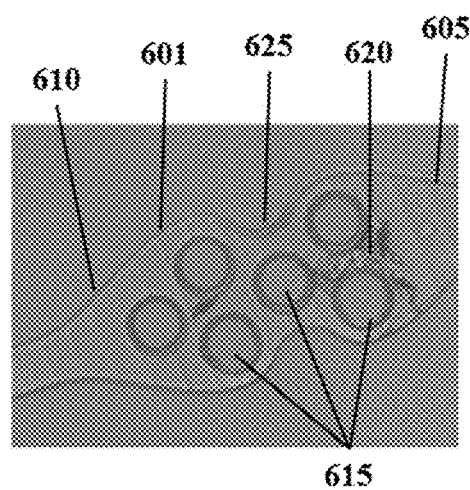
FIG. 6 provides a photomicrograph showing top view of an example of at least one filter feature in a channel with constrictions on opposing sides of the channel.

The channel comprising at least one filter feature may be configured to reduce a concentration of air trapped in the at least one filter feature. For example, as shown in FIG. 6, the channel 601 may include the at least one filter feature between a first end of channel 605 and a second end of channel 610. The at least one filter feature may comprise a plurality of physical obstacles 615. The plurality of physical obstacles 615 may be in a staggered arrangement. The first end of channel 605 may receive a fluid with particles 620 (e.g. debris or fibers). The second end of channel 610 may carry the fluid after filtering through the plurality of physical obstacles 615. The channel 601 may comprise at a plurality of constrictions 625 between the first end of channel 605 and a second end of channel 610. The plurality of constrictions 625 may be at least about 2, 3, 4, 5 or more. The plurality of constrictions may be at least about 2 constrictions on opposing sides of the channel 601. The fluid with particles 620 may flow through the plurality of physical obstacles from the first end of channel 605 toward the second end of channel 610. The particles 620 may be trapped ire the plurality of physical obstacles 615. The plurality of physical obstacles 615 may be useful in separating the particles 620 in the fluid.

Figure 7:
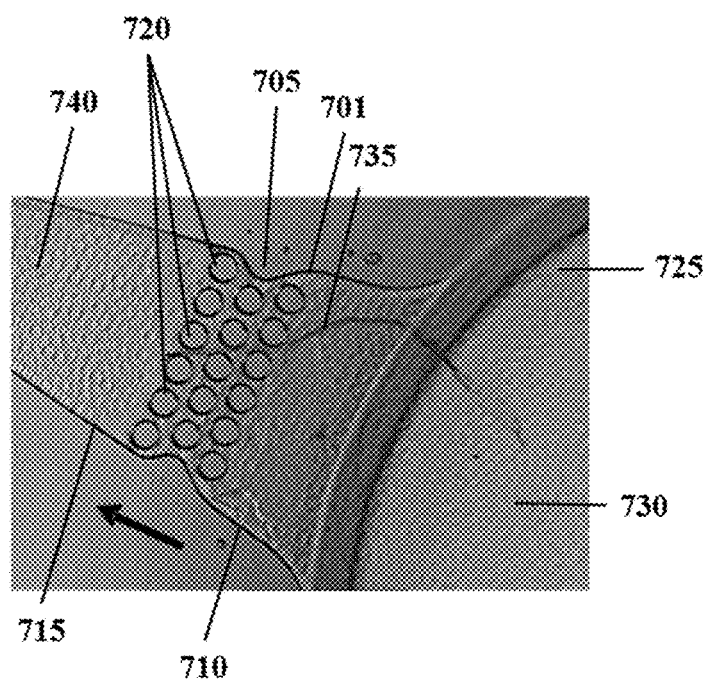
FIG. 7 provides a photomicrograph showing top view of an example of at least one filter feature in a channel with constrictions on opposing sides of the channel and the at least one filter feature in fluid communication with a reservoir.

A channel with a plurality of constrictions may be used to separate a first subset of particles (e.g., gel beads) from a second subset of particles (e.g., debris, fibers). For example, as shown in FIG. 7, a channel 701 may comprise a plurality of constrictions 705 between a first end of channel 710 and a second end of channel 715. The channel 701 may also comprise a plurality of physical obstacles 720 between the first end of channel 710 and the second end of channel 715. The first end of channel 710 may be in fluid communication with a reservoir 725 holding a fluid with particles 730. The first end of channel 710 may receive the fluid. The fluid may then be filtered through the plurality of physical obstacles 720. The fluid may flow through the plurality of physical obstacles 720 as indicated by an arrow in FIG. 7. The plurality of physical obstacles 720 in the channel 701 may be in a staggered arrangement. The plurality of physical obstacles 720 may trap the second subset of particles 735 and the first subset of particles 740 may flow through. The plurality of constrictions 705 may reduce the concentration of air trapped in the plurality of physical obstacles 720.

The plurality of physical obstacles may be arranged in an array in a field in a channel. The plurality of physical obstacles may be distributed randomly in the field in the channel. The array of the plurality of physical obstacles may be in a staggered arrangement. The plurality of physical obstacles in the staggered arrangement may have alternating rows of odd and even number of the plurality of physical obstacles. The plurality of physical obstacles in the array may have a parallel arrangement. The plurality of physical obstacles in the parallel arrangement may form rows and columns with either odd or even number of plurality of physical obstacles.

The plurality of physical obstacles in the field may be at least about 1, 2, 3, 4, 5, 6, 7, 8, 9, 10, 15, 20, 30, 40, 50, 60, 70, 80, 90, 100 or more. In one example, the plurality of physical obstacles may be at least about 6. In another example, the plurality of physical obstacles may be at least about 15. In another example, the plurality of physical obstacles may be at least about 17.

The plurality of physical obstacles may have various shapes, such as cylindrical, conical or pyramidal. In some examples, the plurality of physical obstacles may be cylindrical. The plurality of physical obstacles may be coated with solution. In some examples, the plurality of physical obstacles may be coated with hydrophobic solution.

The plurality of physical obstacles may further comprise a plurality of cylinders. An individual cylinder in the plurality of cylinders may have a cross-sectional dimension and a vertical dimension. In some examples, cross-sectional dimensions and vertical dimensions of at least a subset of the plurality of cylinders may be identical. In other examples, cross-sectional dimensions and vertical dimensions of at least a subset of the plurality of cylinders may be the different.

The plurality of cylinders may comprise at least one passage between the plurality of cylinders. The at least one passage may have a cross-sectional dimension and a vertical dimension. In some examples, cross-sectional dimensions and vertical dimensions of at least a subset of the plurality of cylinders may be the identical. In other examples, cross-sectional dimensions and vertical dimensions of at least a subset of the plurality of cylinders may be the different.

The plurality of cylinders may be arranged in a plurality of concentric rings, sometimes referred to as concentric rings arrangement. The plurality of concentric rings may have an innermost ring. The innermost ring may be in fluid communication with the reservoir. The concentric rings arrangement may include at least about 2, 3, 4, 5, 6, 7, 8, 9, 10 or more of the plurality of concentric rings. The concentric rings arrangement may include at least about 2 of the plurality of concentric rings.

Figure 8:
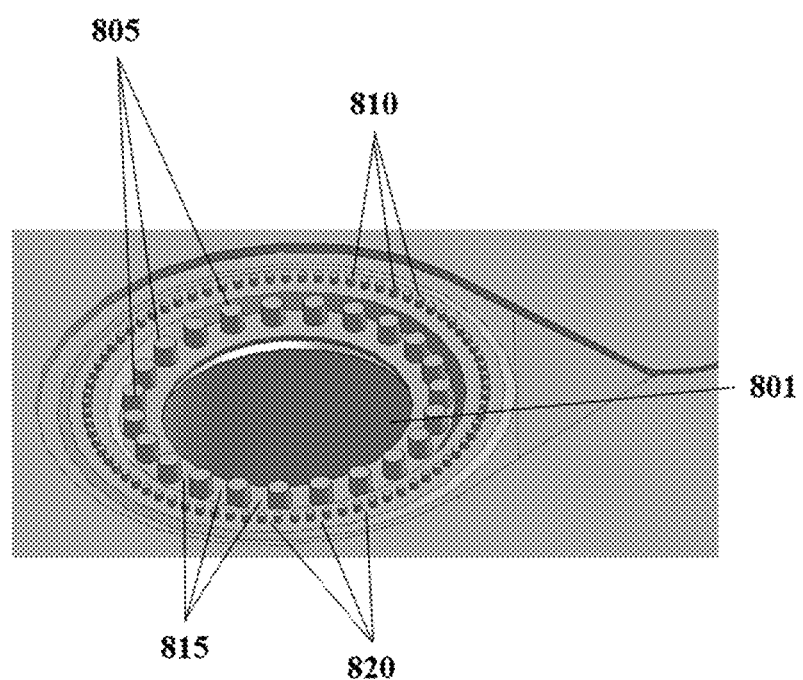
FIG. 8 schematically illustrates an example of at least one filter feature in a concentric rings arrangement in a first end in a channel, in fluid communication with a reservoir.

In some examples, as shown in FIG. 8, a funnel filter may be placed at a first end of a channel. The funnel filter may be in fluid communication with a reservoir 801. The funnel filter may comprise a plurality of physical obstacles. The physical obstacles may comprise a plurality of cylinders. The plurality of cylinders may be arranged in a plurality of concentric rings, sometimes referred to as a concentric rings arrangement. The plurality of concentric rings may be at least about 2. The plurality of concentric rings may comprise an inner ring and an outer ring.

The inner ring may include a first subset of plurality of cylinders 805 and the outer ring may include a second subset of plurality of cylinders 810. The first subset of plurality of cylinders 805 may be in fluid communication with a reservoir 801. The first subset of plurality of cylinders 805 may have larger cross-sectional dimensions and/or vertical dimensions than the second subset of plurality of cylinders 810. In some examples, the inner ring and the outer ring may include the plurality of cylinders having identical cross-sectional dimensions and/or vertical dimensions.

The plurality of cylinders may comprise at least one passage between the plurality of cylinders. The at least one passage may have a cross-sectional dimension and/or vertical dimension. The first subset of plurality of cylinders 805 may comprise a first subset of passages 815. The second subset of plurality of cylinders 810 may comprise a second subset of passages 820. The first subset of passages 815 may have different cross-sectional dimensions and/or vertical dimensions than the second subset of passages 820. The first subset of passages 815 and the second subset of passages may have identical cross-sectional dimensions and/vertical dimensions.

Figures 9A, 9B, 9C:
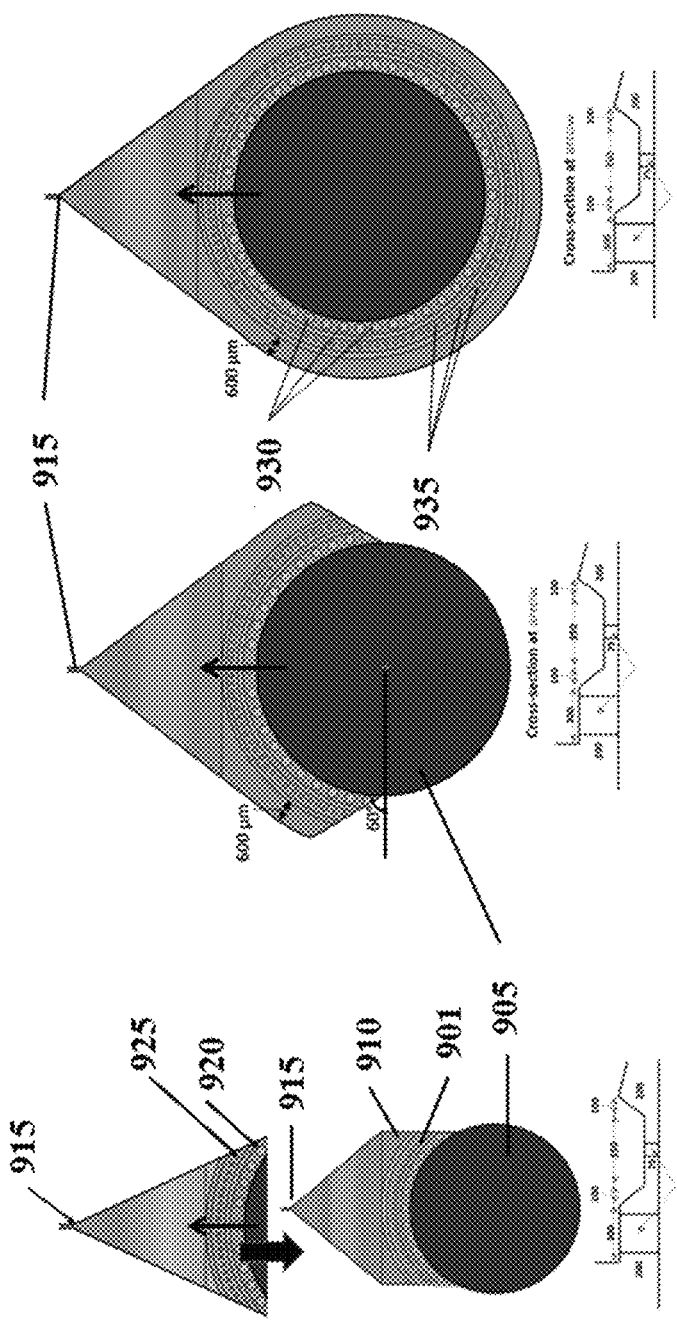
FIGS. 9A-9C schematically illustrates an example of at least one filter feature in a concentric rings arrangement with two configurations and provides dimensions for parts of the concentric rings arrangements.

The cross-sectional dimension of the plurality of cylinders in the inner ring may be at least about 1 micrometer (µm), 10 µm, 20 µm, 30 µm, 40 µm, 50 µm, 100 µm, 150 µm, 160 µm, 170 µm, 180 µm, 190 µm, 200 µm, 300 µm or more. In one example, as shown in FIG. 9A-C the cross-sectional dimensional is at least about 300 µm. The vertical dimensional of the plurality of cylinders in the inner ring may be at least about 1 micrometer (µm), 10 µm, 20 µm, 30 µm, 40 µm, 50 µm, 100 µm, 150 µm, 160 µm, 170 µm, 180 µm, 190 µm, 200 µm, 300 µm or more. In one example, as shown in FIG. 9A-C the vertical dimensional is at least about 200 µm.

The cross-sectional dimension of the plurality of cylinders in the outer ring may be at least about 1 micrometer (µm), 10 µm, 20 µm, 30 µm, 40 µm, 50 µm, 100 µm, 150 µm, 160 µm, 170 µm, 180 µm, 190 µm, 200 µm or more. In one example, the cross-sectional dimensional is at least about 200 µm. The vertical dimension of the plurality of cylinders in the outer ring may be at least about 1 µm, 10 µm, 20 µm, 30 µm, 40 µm, 50 µm 60 µm, 70 µm, 80 µm, 90 µm, 100 µm or more. In one example, as shown in FIG. 9A-C the vertical dimensional is at least about 75 µm. The cross-sectional dimension of the plurality of cylinders in the inner ring may be greater than the cross sectional dimension of the plurality of cylinders in the outer ring.

The cross-sectional dimension of the first subset of passages may be at least about 1 micrometer (µm), 10 µm, 20 µm, 30 µm, 40 µm, 50 µm, 100 µm, 150 µm, 160 µm, 170 µm, 180 µm, 190 µm, 200 µm, 210 µm, 225 µm, 250 µm, 300µm, 350 µm, 400 µm or more. In one example, the cross-sectional dimension of the first subset of passages may be at least about 200 µm. The cross-sectional dimension of the second subset of passages may be at least about 1 micrometer (µm), 10 µm, 20 µm, 30 µm, 40 µm, 50 µm, 100 µm, 150 µm, 160 µm, 170 µm, 180 µm, 190 µm, 200 µm or more. In one example, the cross-sectional dimension of the second subset of passages may be at least about 75 µm.

In some examples, as shown in FIG. 9A-C, at least one filter feature 901 in a concentric rings arrangement may encircle a reservoir 905. In one example, as shown in FIG. 9A-B, the at least one filter feature 901 in the concentric rings arrangement may encircle reservoir 905 partially. In another example, as shown in FIG. 9C, the at least one filter feature 901 in the concentric rings arrangement may encircle reservoir 905 completely. The at least one filter feature may be at a first end of channel 910, in fluid communication with the reservoir 905. The first end of channel 910 tapers toward a second end of channel 915. In one example, a cross-sectional dimension of the first end of channel 910 may be at least about 200 µm. A cross-sectional dimension of the second end of channel 915 may be at least about 75 µm. The concentric rings arrangement may comprise an inner ring 920 and an outer ring 925. The inner ring 920 may comprise a first subset of plurality of cylinders 930. The outer ring 925 may comprise a second subset of plurality of cylinders 935. Cross-sectional dimensions and/vertical dimensions of the first subset of plurality of cylinders 930 in the inner ring 920 may be greater than the cross sectional dimensions and/or vertical dimensions of the second subset of plurality of cylinders 935 in the outer ring 925.

Figure 10:
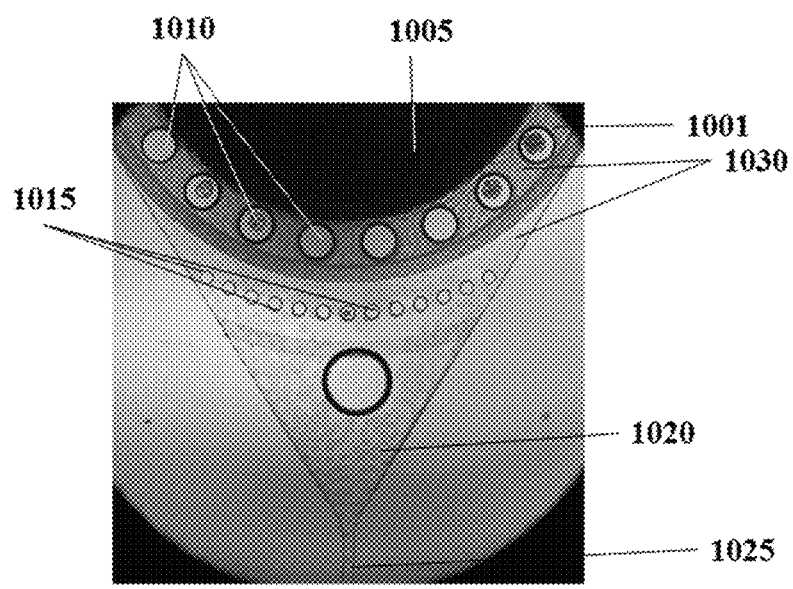
FIG. 10 provides a photomicrograph of an example channel with at least one filter feature in a concentric rings arrangement in fluid communication with a reservoir holding a fluid with gel beads.

In some examples, as shown in FIG. 10, a concentric rings arrangement of at least one filter feature may be used to filter a fluid with particles (e.g., gel beads). The at least one filter feature may be located at a first end of channel 1001. The at least one filter feature may be configured to partially encircle a reservoir 1005 holding the fluid with particles. The concentric rings arrangement may comprise an inner ring and an outer ring. The inner ring may comprise a first subset of plurality of cylinders 1010. The outer ring may comprise a second subset of plurality of cylinders 1015. Cross-sectional dimensions and/vertical dimensions of the first subset of plurality of cylinders 1010 in the inner ring may be greater than the cross sectional dimensions and/or vertical dimensions of the second subset of plurality of cylinders 1015 in the outer ring.

The particles may comprise gel beads 1020. The gel beads 1020 in the fluid may flow from the first end of channel to a second end of channel 1025. The gel beads 1020 may form aggregates 1030 in the channel. The aggregates 1030 of the gel beads 1020 may be trapped in the first subset of plurality of cylinders 1010 and the second subset of plurality of cylinders 1015. The concentric rings arrangement may be useful in separating the aggregates 1030 from the gel beads 1020.

Figure 11:
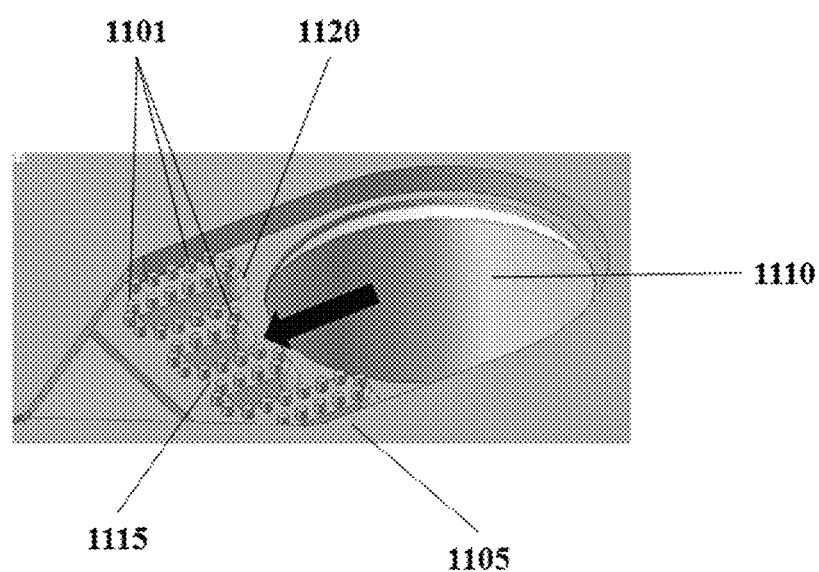
FIG. 11 schematically illustrates an example of at least one filter feature in a serpentine arrangement in a first end in a channel, in fluid communication with a reservoir.

In some examples, as shown in FIG. 11, the plurality of cylinders 1101 may be arranged in a serpentine configuration. The plurality of cylinders 1101 may be located in a first end of channel 1105, in fluid communication with a reservoir 1110. The plurality of cylinders 1101 may partially encircle the reservoir 1110. The serpentine configuration may include at least one flat portion 1115 connecting to at least one convex portion 1120, protruding towards the reservoir 1110. The convex portion 1120 may have a drop-off with respect to the flat portion 1115. The at least one flat portion 1115 may connect the at least one convex portion 1120 on opposite ends of the at least one flat portion 1115. The at least one convex portion 1120 may come in contact with the fluid first as the fluid from the reservoir 1110 to the first end of channel 1105, as indicated by an arrow. The serpentine configuration may comprise at least about three flat portions connecting to at least about four convex portions. The arrow illustrates the general direction of fluid flow, in an example. In another example, the general direction of fluid flow may be reversed.

The serpentine configuration may comprise at least about 1, 2, 3, 4, 5, 6, 7, 8, 9, 10, 20, 30, 40, 50, 60, 70, 80, 90, 100 flat portions. The serpentine configuration may connect or be in fluid communication with at least 1, 2, 3, 4, 5, 6, 7, 8, 9, 20, 30, 40, 50, 60, 70, 80, 90, or 100 convex portions.

In one example, as shown in FIG. 12A, the plurality of cylinders 1201 in the serpentine configuration may partially encircle a reservoir 1205 at a first end of channel 1210. In other examples, the plurality of cylinders 1201 in the serpentine configuration may completely encircle the reservoir at the first end of channel (not shown).

The first end of channel 1210 tapers toward a second end of channel 1215. The first end of channel 1210 may have larger cross-sectional dimension than the second end of channel 1215. For example, the cross-sectional dimension of the first end of channel 1210 may be at least about 200 μm. The cross-sectional dimension of the second end of channel 1215 may be at least about 75 μm.

The serpentine configuration may include at least one flat portion 1220 connecting to at least one convex portion 1225, protruding towards the reservoir 1205. Cross-sectional dimensions of the at least one flat portion 1220 may be at least about 10 μm, 100 μm, 200 μm, 300 μm, 400 μm or more. In one example, as shown in FIG. 12A, a cross-sectional dimension of the at least one flat portion 1220 may be at least about 260 μm. Cross-sectional dimensions of the at least one convex portion 1225 may be at least about 10 μm, 100 μm, 200 μm, 300 μm, 400 μm or more. In one example, as shown in FIG. 12A, a cross-sectional dimension of the at least one convex portion 1225 may be at least about 350 μm. The at least one convex portion 1225 may have a wall 1230 having a cross-sectional dimension. The cross-sectional dimension of the wall 1230 may be at least about 1 μm, 10 μm, 20 μm, 30 μm, 40 μm or more. In one example, as shown in FIG. 12A, the cross-sectional dimension of the wall 1230 may be at least about 50 μm. The at least one convex portion 1225 may have vertical dimensions. As shown in FIG. 12A, the vertical dimensions of the at least one convex portion may be different. The vertical dimensions of the at least one convex portion may be similar (not shown).

The plurality of cylinders 1201 in the serpentine arrangement may have different cross-sectional dimensions and/or vertical dimensions. For example, as shown in FIG. 12A, the plurality of cylinders 1201 may have a first subset of cylinders 1235 and a second subset of cylinders 1240. The first subset of cylinders 1235 may be located at a tip of the at least one convex portion and at the at least one flat portion 1220. The first subset of cylinders 1235 may have larger cross-sectional dimensions than the second subset of cylinders 1240. Cross-sectional dimensions of the first subset of cylinders 1235 may be at least about 1 μm, 100 μm, 200 μm, 300 μm, 400 μm or more. In one example, as shown in FIG. 12A, a cross-sectional dimension of the first subset of cylinders 1235 may be at least about 200 μm. Cross-sectional dimensions of the second subset of cylinders 1240 may be at least about 1 μm, 100 μm, 200 μm, 300 μm, 400 μm or more. In one example, as in FIG. 12A, a cross-sectional dimension of the second subset of cylinders 1240 may be at least about 75 μm. Vertical dimensions of the first subset of cylinders 1235 may be at least about 1 μm, 100 μm, 200 μm, 300 μm, 400 μm or more. In one example, as in FIG. 12A, a vertical dimension of the first subset of cylinders 1235 may be at least about 200 μm. Vertical dimensions of the second subset of cylinders 1240 may be at least about 1 μm, 100 μm, 200 μm, 300 μm, 400 μm or more. In one example, as in FIG. 12A, a vertical dimension of the second subset of cylinders 1240 may be at least about 75 μm.

The plurality of cylinders 1201 in the serpentine arrangement may have identical cross-sectional dimensions and/or vertical dimensions. For example, as shown in FIG. 12B, cross-sectional dimensions of the plurality of cylinders 1201 may be at least about 1 μm, 100 μm, 200 μm, 300 μm, 400 μm or more. In one example, as shown in FIG. 12B, cross-sectional dimensions of the plurality of cylinders 1201 may be at least about 75 μm. Vertical dimensions of the plurality of cylinders 1201 may be at least about 1 μm, 100 μm, 200 μm, 300 μm, 400 μm or more. In one example, as in FIG. 12B, vertical dimensions of the plurality of cylinders 1201 may be at least about 75 μm.

The plurality of cylinders 1201 in the serpentine configuration may include at least one passage 1245. The at least one passage 1245 may have a cross-sectional dimension. The cross-sectional dimension of the at least one passage 1245 may be similar. The cross-sectional dimension of the at least one passage 1245 may be at least about 1 μm, 5 μm, 10 μm, 20 μm, 30 μm, 40 μm, 50 μm, 60 μm, 70 μ, 80 μm, 90 μm, 100 μm, 110 μm, 120 μm, 130 μm, 140 μm, 150 μm or more. In one example, as shown in FIG. 12B, cross-sectional dimension of the at least one passage 1245 may be at least about 75 μm. The cross-sectional dimension of the at least one passage may be different (not shown).

Figure 13:
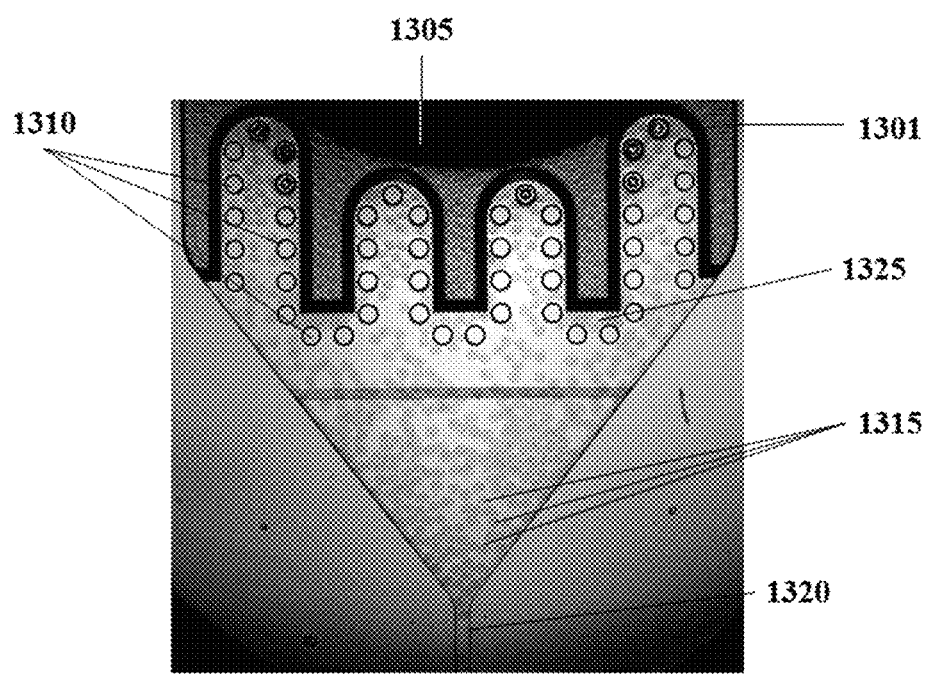
FIG. 13 provides a photomicrograph of an example of at least one filter feature in a serpentine arrangement in fluid communication with a reservoir holding a fluid with gel beads.

In some examples, as shown in FIG. 13, a serpentine arrangement of at least one filter feature may be used to filter a fluid with particles (e.g., gel beads). The at least one filter feature may be located at a first end of channel 1301. The at least one filter feature may be configured to partially encircle a reservoir 1305 holding the fluid with particles. The serpentine arrangement may comprise a plurality of cylinders 1310. Cross-sectional dimensions and/vertical dimensions of the plurality of cylinders 1310 in the serpentine ring arrangement may be similar The particles may comprise gel beads 1315. The gel beads 1315 in the fluid may flow from the first end of channel to a second end of channel 1320. The gel beads 1315 may form aggregates 1325 in the channel. The aggregates 1325 of the gel beads 1315 may be trapped in the plurality of cylinders 1310. The serpentine arrangement may be useful in separating the aggregates 1325 from the gel beads 1315.

The direction of the fluid in the channel from the first end of channel to the second end of channel may be oriented along a direction of a gravitational acceleration vector. The direction of the gravitational acceleration vector may include positioning the first end above the second end such that the reservoir may be above the output reservoir.

The direction of the fluid in the channel from the first end to the second end may be oriented along a direction of a pressure increase or decrease along a direction leading from the first end to the second end. The direction of the pressure increase or decrease may include positioning of the first end and the second end such that first end may be higher pressure than the second end. The pressure increase or decrease may be achieved by using a controller coupled to a pump (e.g., micro pump).

The at least one filter feature may comprise at least one passage with a cross-section. The cross-section of the at least one passage may be greater than or equal to an average diameter of the particle in the fluid among other particles in the fluid. The cross section of the at least one passage having greater than or equal to an average diameter of the particle may be useful for the particles that do not deform, compress or bend.

The cross-section of the at least one passage may be less than an average diameter of the particle in the fluid among other particles in the fluid. The cross section of the at least one passage having less than an average diameter of the particle may be useful for the particles that deform, compress or bend such as gel beads.

The particles in the fluid may include contaminants. The contaminants may be introduced by environment, such as airborne particulate matter, by consumables, such as pipette tips or by reagents, such as chemical compounds. The contaminants may be introduced by the environment, the consumables and the reagents during a step or a plurality of steps in processing of the sample.

The particles may be beads. In some cases, the beads may be porous, non-porous, solid, semi-solid, semi-fluidic, fluidic, and/or a combination thereof. In some instances, the beads may be dissolvable, disruptable, and/or degradable. In some cases, beads may not be degradable. In some cases, the bead may be gel beads. The gel beads may be hydrogel beads.

In some instances, the bead may comprise molecular precursors (e.g., monomers or polymers), which may form a polymer network via polymerization of the precursors. In some cases, a precursor may be an already polymerized species capable of undergoing further polymerization via, for example, a chemical cross-linkage. In some cases, a precursor can comprise one or more of an acrylamide or a methacrylamide monomer, oligomer, or polymer. In some cases, the bead may comprise prepolymers, which are oligomers capable of further polymerization. For example, polyurethane beads may be prepared using prepolymers. In some cases, the bead may contain individual polymers that may be further polymerized together. In some cases, beads may be generated via polymerization of different precursors, such that they comprise mixed polymers, co-polymers, and/or block co-polymers.

In some cases, a chemical cross-linker may be a precursor used to cross-link monomers during polymerization of the monomers and/or may be used to attach oligonucleotides (e.g., barcoded oligonucleotides) to the bead. In some cases, polymers may be further polymerized with a cross-linker species or other type of monomer to generate a further polymeric network or a matrix. Non-limiting examples of chemical cross-linkers (also referred to as a "crosslinker" or a "crosslinker agent" herein) include cystamine, gluteraldehyde, dimethyl suberimidate, N-Hydroxysuccinimide crosslinker BS3, formaldehyde, carbodiimide (EDC), SMCC, Sulfo-SMCC, vinylsilane, N,N'diallyltartardiamide (DATD), N,N'-Bis(acryloyl)cystamine (BAC), or homologs thereof. In some cases, the matrix may include polymer meshes, entangled polymers or similar structures to provide surface for attachment of reagents. In some aspects, hydrogen polymers may be useful as the matrix.

A bead may comprise natural and/or synthetic materials. For example, a polymer can be a natural polymer or a synthetic polymer. In some cases, a bead can comprise both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and/or combinations (e.g., co-polymers) thereof. Beads may also be formed from materials other than polymers, including lipids, micelles, ceramics, glass-ceramics, material composites, metals, other inorganic materials, and others.

The gel beads may be uniform or heterogeneous in cross-sectional dimensions. In some cases, the cross-sectional dimensions may have range between 1 micrometer (μm) to 1 millimeter (mm), 10 μm to 100 μm, 20 μm to 100 μm, 30 μm to 80 μm or 40 μm to 60 μm. Some examples of cross-sectional dimensions may include 30 μm, 40 μm, 50 μm, 55 μm, 57 μm, 60 μm, 64 μm, 70 μm, 72 μm, 75 μm, 100 μm, 125 μm, 150 μm, 200 μm, 250 μm, 500 μm, 750 μm and 1 mm.

The particles may be cellular components. The cellular components may include membranes, organelles, macromolecular components e.g., RNA, DNA, proteins, etc.). The cellular component may be released by lysis of cells or may be associated with the cells.

The particles may further be coupled to barcodes. The barcodes can be nucleic acid molecules with nucleic acid sequences. The barcodes across at least a subset of the particles are different. The barcodes can be assigned or associated with the at least a subset of particles to tag or label with unique identifiers. The nucleic acid sequences can include from 6 to about 20 or more nucleotides within a sequence of oligonucleotides.

The particles may be cells. The cells may be enclosed inside of or comprise a gel or a matrix (e.g., polymer matrix) to form a "cell bead." The cell bead can contain cells or macromolecular constituents (e.g., RNA, DNA, proteins, etc.) of the cells. The cell bead may include a single cell or multiple cells, or a derivative of the single cell or multiple cells. For example after lysing and washing the cells, inhibitory components from cell lysates can be washed away and the macromolecular constituents can be bound as cell beads. In some cases, the cell bead may further comprise one or more field-attractable particles (e.g., paramagnetic particles, conductive particles, etc.), for facilitating sorting of the particles and further assaying. The field-attractable particles may be trapped in the gel matrix. In some instances, the field-attractable particles may be trapped evenly throughout the gel matrix. In some instances, the field-attractable particles may be trapped throughout the gel matrix such as to subject the whole of the cell bead evenly to a force (e.g., magnetic, electric) field.

The particles may be comprised in a population of particles. The population of particles may be homogeneous with similar or identical cross-sectional and/or vertical dimensions. The population of particles may be heterogeneous with dissimilar cross-sectional and/or vertical dimensions. Heterogeneity in the population of particles can be referred to as dispersity. The dispersity may influence flow characteristics of the fluid flowing through the at least one channel of the microfluidic device since the particles can have different flow characteristics due to dissimilar cross-sectional and/or vertical dimensions.

The dispersity may also influence blockage of the at least one channel. In some cases, the population of particles may be relatively monodisperse distribution. In particular, the dispersity of the particles described herein may have size distributions that have a coefficient of variation in their cross-sectional and/or vertical dimensions of less than 50%, less than 40%, less than 30%, less than 20%, and in some cases less than 15%, less than 10%, less than 5%, or less.

The dispersity may be determined by any suitable method. For example, high throughput measurements, e.g., measurements of 1000 or more particles, automated microscopy (e.g., using a Morphologi G3 system), dynamic imaging analysis (e.g., using a flow monitoring camera system), and light scattering (e.g., using a Mastersizer 3000 system), may be used.

The particles with a given cross-sectional dimension and/or vertical dimension may be produced using controlled preparation techniques, post preparation sorting and sizing techniques. For example, the given cross-sectional dimension and/or vertical dimension may be selected using size exclusion based separation techniques such as filtration or sieving techniques.

In some cases, nature of the particles may prevent use of size exclusion based separation techniques. For example, filtration techniques may be ineffective for the particles that are highly elastic or deformable since the particles may deform and pass through smaller openings than the given cross-sectional dimension and/or vertical dimension, resulting in dispersity. The particles that are deformable may also be more susceptible to blocking the channel.

In some cases, the population of particles may be subjected to alternate methods to separate the particles with a given cross-sectional dimension and/or vertical dimension. For example, the population of particles may include a first subset of particles with a first given cross-sectional dimension and/or vertical dimension along with a second subset of particles with a second given cross-sectional dimension and/or vertical dimension. Further, the first given cross-sectional dimension and/or vertical dimension may be smaller than the second given cross-sectional dimension and/or vertical dimension. The population of particles may be subjected to a flotation filtration technique where the fluid with the population of particles can be provided in a floatation chamber with an upward flow rate applied through the flotation chamber. The upward flow rate may be less than a gravitational acceleration vector of the second subset of the particles that may result in settling of the second subset of the particles while the first subset of the particles may float in the flotation chamber. The first subset of the particles can then be separated in the output reservoir. The particles may be separated on the basis of size and/or density.

In some cases, the particles with a given cross-sectional dimension and/or vertical dimension may be produced using size exclusion based separation techniques. For example, vector chromatography methods and systems can be used. In the vector chromatography systems, the channels or conduits with longer vertical dimensions can be provided for carrying the fluid with the particles. For example, the population of particles may include a first subset of particles with a first given cross-sectional dimension and/or vertical dimension along with a second subset of particles with a second given cross-sectional dimension and/or vertical dimension. Further, the first given cross-sectional dimension and/or vertical dimension may be smaller than the second given cross-sectional dimension and/or vertical dimension. The first subset of particles may traverse through the fluid faster compared to the second subset of particles and the first subset of particles may reach the output reservoir before the second subset of particles.

The particles may be of any suitable shape. Examples of particle shapes include, but are not limited to, spherical, non-spherical, oval, oblong, amorphous, circular, cylindrical, and variations thereof.

In an aspect, the present disclosure provide a system for filtering particles in a fluid may include a microfluidic device. The microfluidic device may further comprise a reservoir for holding the fluid comprising the particles, a channel in fluid communication with the reservoir and at least one filter feature in the channel. The at least one filter feature may comprise a field of a plurality of physical obstacles configured and arranged in the channel. The at least one filter feature may separate the particles in the fluid upon flow of the fluid from the reservoir through the channel.

For example, the at least one filter feature may retain the particles and permit the fluid to flow through, thereby separating the particles from the fluid. As another example, the at least one filter feature may separate the particles from contaminants (e.g., debris), to permit the fluid with particles to flow through with a decrease in an amount or concentration of the contaminants.

The channel may comprise a first end and a second end, wherein the first end is adjacent to the reservoir. A cross-section of the channel may decrease along a direction leading from the first end to the second end. The cross-section may be tapered. For example, the cross-section gradually decreases.

In addition to features of the microfluidic mentioned herein, the system may comprise a controller. The controller may be operatively coupled to the microfluidic device, wherein the controller subjects the fluid to flow from the reservoir to the channel. For example, the controller can be programmed to regulate flow options, e.g., the controller may instruct the microfluidic device to flow the fluid from the reservoir at a flow pressure and a flow rate. The controller can also be programmed to instruct the microfluidic device to release the fluid to the output reservoir. The controller can be programmed to direct the fluid from a reservoir to a filter feature. The controller can be programmed to regulate flow of the fluids in a first channel and a second channel. The fluids in the first channel and the second channel may be in fluid communication at an intersection.

Methods

In an aspect, the present disclosure provides methods for filtering particles in a fluid. A method for filtering a particle in a fluid may comprise activating a microfluidic device comprising (i) a reservoir for holding the fluid comprising the particles, (ii) a channel in fluid communication with the reservoir, and (iii) at least one filter feature in the channel. The at least one filter feature may comprise a field of a plurality of physical obstacles configured and arranged in the channel, wherein the channel comprises a first end and a second end. The first end is adjacent to the reservoir. A cross-section of the channel decreases along a direction leading from the first end to the second end. The fluid may be subjected to flow from the reservoir to the channel. Upon flow of the fluid from the reservoir through the channel, the at least one filter feature separates the particles in the fluid. The fluid may be subjected to flow with the aid of a pressure increase or decrease along a direction leading from the first end to the second end.

In some embodiments, the method may include collecting the particles in an output reservoir. In some embodiments, method may further include directing the particles collected in the output reservoir to further processing. In some embodiments, the method may include directing the particles collected in the output reservoir to further processing.

In some embodiments, the method may include directing the particles to partitions. The partitions may be droplets. The partitions may be wells.

In some embodiments, the particles may include contaminants. In some embodiments, the particles may include beads. In some embodiments, the particles may include cellular components. In some embodiments, the particles may include cells. In some embodiments, the particles may include barcodes coupled thereto. The barcodes may be nucleic acid molecules comprising nucleic acid sequences. The barcodes across at least a subset of the plurality of particles may be different.

Computer Control Systems

Figure 14:
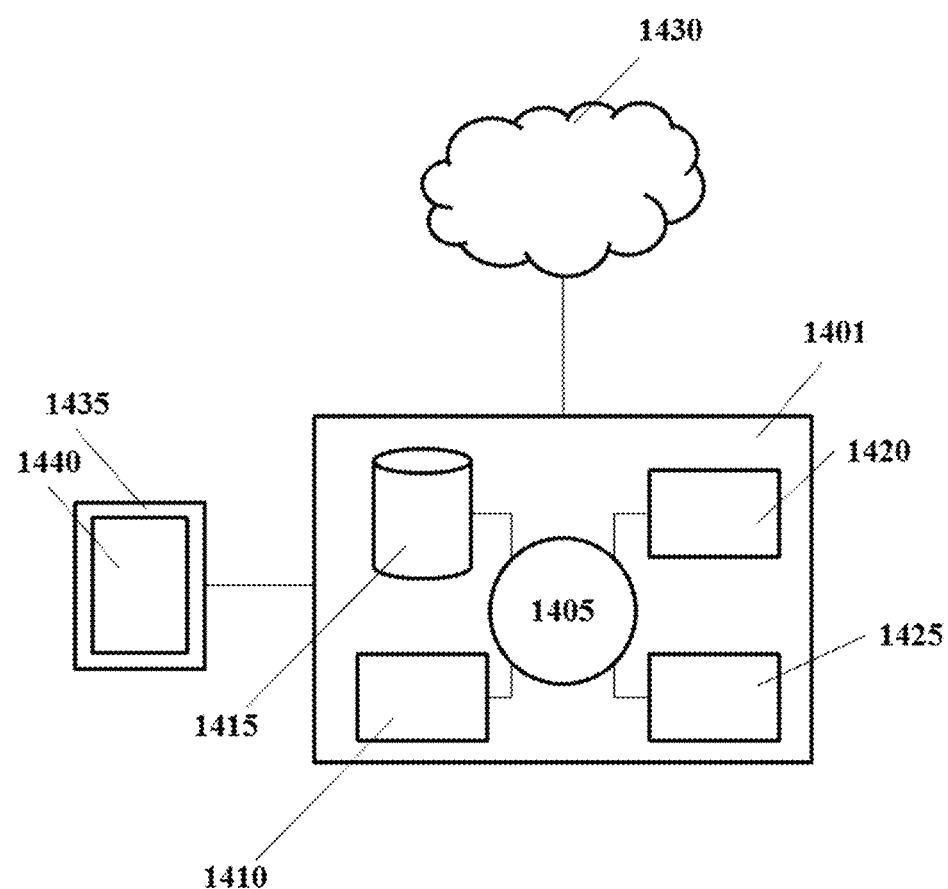
FIG. 14 shows an example computer control system that is programmed or otherwise configured to implement methods provided herein.

The present disclosure provides computer control systems that are programmed to implement methods of the disclosure. FIG. 14 shows a computer system 1401 that is programmed or otherwise configured to implement method of the disclosure including operation of a microfluidic system, activating a microfluidic device and subjecting a fluid to flow from a reservoir to a channel. The computer system 1401 can regulate various aspects of the apparatuses, systems and methods of the present disclosure, such as, for example, a flow rate of the fluid from the reservoir to a filter feature in a channel, a flow rate of the fluid from the channel to an output reservoir after filtration through eth filter feature, a fluid pressure of the fluid entering the filter feature, a fluid pressure of the fluid exiting the filter feature, a concentration of particles released in the output reservoir. The computer system 1401 can be an electronic device of a user or a computer system that is remotely located with respect to the electronic device. The electronic device can be a mobile electronic device.

The computer system 1401 includes a central processing unit (CPU, also "processor" and "computer processor" herein) 1405, which can be a single core or multi core processor, or a plurality of processors for parallel processing. The computer system 1401 also includes memory or memory location 1410 (e.g., random-access memory, read-only memory, flash memory), electronic storage unit 1415 (e.g., hard disk), communication interface 1420 (e.g., network adapter) for communicating with one or more other systems, and peripheral devices 1425, such as cache, other memory, data storage and/or electronic display adapters. The memory 1410, storage unit 1415, interface 1420 and peripheral devices 1425 are in communication with the CPU 1405 through a communication bus (solid lines), such as a motherboard. The storage unit 1415 can be a data storage unit (or data repository) for storing data. The computer system 1401 can be operatively coupled to a computer network ("network") 1430 with the aid of the communication interface 1420. The network 1430 can be the Internet, an internet and/or extranet, or an intranet and/or extranet that is in communication with the Internet. The network 1430 in some cases is a telecommunication and/or data network. The network 1430 can include one or more computer servers, which can enable distributed computing, such as cloud computing. The network 1430, in some cases with the aid of the computer system 1401, can implement a peer-to-peer network, which may enable devices coupled to the computer system 1401 to behave as a client or a server.

The CPU 1405 can execute a sequence of machine-readable instructions, which can be embodied in a program or software. The instructions may be stored in a memory location, such as the memory 1410. The instructions can be directed to the CPU 1405, which can subsequently program or otherwise configure the CPU 1405 to implement methods of the present disclosure. Examples of operations performed by the CPU 1405 can include fetch, decode, execute, and writeback.

The CPU 1405 can be part of a circuit, such as an integrated circuit. One or more other components of the system 1401 can be included in the circuit. In some cases, the circuit is an application specific integrated circuit (ASIC).

The storage unit 1415 can store files, such as drivers, libraries and saved programs. The storage unit 1415 can store user data, e.g., user preferences and user programs. The computer system 1401 in some cases can include one or more additional data storage units that are external to the computer system 1401, such as located on a remote server that is in communication with the computer system 1401 through an intranet or the Internet.

The computer system 1401 can communicate with one or more remote computer systems through the network 1430. For instance, the computer system 1401 can communicate with a remote computer system of a user (e.g., operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1401 via the network 1430.

Methods as described herein can be implemented by way of machine (e.g., computer processor) executable code stored on an electronic storage location of the computer system 1401, such as, for example, on the memory 1410 or electronic storage unit 1415. The machine executable or machine readable code can be provided in the form of software. During use, the code can be executed by the processor 1405. In some cases, the code can be retrieved from the storage unit 1415 and stored on the memory 1410 for ready access by the processor 1405. In some situations, the electronic storage unit 1415 can be precluded, and machine-executable instructions are stored on memory 1410.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1401 can include or be in communication with an electronic display 1435 that comprises a user interface (UI) 1440 for providing, for example, fluid control options (e.g., flow rate of the fluid, fluid pressure, concentration of particles, flow rate in the filter feature, flow rate in the output reservoir, etc.). Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1405. The algorithm can, for example, (i) filter a fluid with particles to sort into individual particles by separating aggregates using at least one filter feature, (ii) selectively filter a first subset of particles (e.g., debris) from a second subset of particles (gel beads) in a fluid, and/or (iii) sort individual gel beads into a plurality of droplets or an array of wells for further analyzing.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A microfluidic device for filtering particles in a fluid, comprising:
   a reservoir configured to hold the fluid comprising the particles;
   a first channel in fluid communication with the reservoir; and
   at least one filter feature in the channel, wherein the at least one filter feature comprises a field of a plurality of physical obstacles arranged in the channel, wherein the at least one filter feature separates the particles in the fluid upon flow of the fluid from the reservoir through the channel, wherein the at least one filter feature comprises at least one passage between the plurality of physical obstacles and through the filter feature with a cross-section that is at least 30 um, and wherein the channel comprises a first end and a second end, wherein the first end is directly connected to the reservoir and the first end is disposed between the reservoir and the second end and wherein the at least one filter feature is at least partially located in a tapered portion of the channel at the first end that decreases in cross-section along a direction leading from the first end to the second end or wherein the at least one filter feature is located in a portion of the channel comprising a contraction followed by an expansion, the filter feature comprises an upstream end and a downstream end, and wherein the expansion and contraction are between the upstream and downstream ends of the field of the plurality of physical obstacles of the at least one filter feature.

2. The microfluidic device of claim 1, wherein the reservoir, the first channel, and at least one filter feature are integrated in a chip.

3. The microfluidic device of claim 2, wherein the chip comprises a plurality of compartments fluidically connected to the reservoir.

4. The microfluidic device of claim 1, wherein the plurality of physical obstacles includes a plurality of cylinders each having a cross-sectional dimension and a vertical dimension arranged within the field.

5. The microfluidic device of claim 4, wherein respective cross-sectional dimensions and vertical dimensions of at least a subset of the plurality of cylinders are the same.

6. The microfluidic device of claim 4, wherein at least a subset of the plurality of cylinders have different cross-sectional dimensions and vertical dimensions.

7. The microfluidic device of claim 4, wherein the plurality of cylinders is arranged in a plurality of concentric rings, wherein the plurality of concentric rings comprises an inner ring and an outer ring, and wherein the inner ring is disposed between the outer ring and the reservoir, and wherein the at least one filter feature is at least partially located in a tapered portion of the channel at the first end that decreases in cross-section along a direction leading from the first end to the second end.

8. The microfluidic device of claim 7, wherein the inner ring comprises a first subset of the plurality of cylinders having larger cross-sectional dimensions and/or vertical dimensions than a second subset of the plurality of cylinders in the outer ring.

9. The microfluidic device of claim 4, wherein the plurality of cylinders is arranged in a serpentine configuration at the first end of the channel, wherein the serpentine configuration includes at least one convex portion comprising a subset of the plurality of cylinders, which convex portion is in fluid communication with the reservoir.

10. The microfluidic device of claim 1, wherein the direction is oriented along a direction of a gravitational acceleration vector.

11. The microfluidic device of claim 1, wherein the direction is oriented along a direction of a pressure increase or decrease along a direction leading from the first end to the second end.

12. The microfluidic device of claim 1, wherein the at least one filter feature comprises at least one passage with a cross-section that is greater than or equal to a diameter of one of the particles in the fluid.

13. The microfluidic device of claim 1, wherein the at least one filter feature comprises at least one passage with a cross-section that is less than a diameter of one of the particles in the fluid.

14. The microfluidic device of claim 1, wherein the particles are contaminants, beads, cells, or cellular components.

15. The microfluidic device of claim 14, wherein the particles comprise, or are enclosed in, a gel or a polymer matrix.

16. The microfluidic device of claim 14, wherein the particles comprise cellular components, and wherein the cellular components include one or more members selected from the group consisting of cell membrane, cell wall, organelles, macromolecular constituent, deoxyribonucleic acid (DNA), and ribonucleic acid (RNA).

17. The microfluidic device of claim 1, wherein the particles comprise a homogeneous population of particles or a heterogeneous population of particles.

18. The microfluidic device of claim 1, wherein the particles comprise nucleic acid barcodes coupled thereto.

19. The microfluidic device of claim 1, wherein the first channel comprises the contraction followed by the expansion, and the contraction comprises (a) at least one constriction between the upstream and downstream ends to reduce a concentration of air trapped in the filter feature or (b) at least two constrictions on opposite sides of the channel between the upstream and downstream ends to reduce a concentration of air trapped in the at least one filter feature.

20. The microfluidic device of claim 1, wherein the first channel comprises at least one passive valve and at least one rectifier and the at least one filter feature is disposed between the at least one passive valve and the at least one rectifier.

21. The microfluidic device of claim 1, wherein the at least one filter feature is at least partially located in the tapered portion of the first channel at the first end.

22. The microfluidic device of claim 1, wherein the at least one filter feature is located in the portion of the channel comprising the contraction followed by an expansion, wherein the expansion and contraction are between the upstream and downstream ends of the field of the plurality of physical obstacles of the at least one filter feature.

* * * * *